US007888345B2

(12) United States Patent
Hoyt et al.

(10) Patent No.: US 7,888,345 B2
(45) Date of Patent: Feb. 15, 2011

(54) BENZAEPINONES AS SODIUM CHANNEL BLOCKERS

(75) Inventors: Scott B. Hoyt, Hoboken, NJ (US); Clare London, Chatham, NJ (US); Dong Ok, Edison, NJ (US); William H. Parsons, Belle Meade, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 230 days.

(21) Appl. No.: 12/308,209

(22) PCT Filed: Jun. 5, 2007

(86) PCT No.: PCT/US2007/013202

§ 371 (c)(1), (2), (4) Date: Dec. 8, 2008

(87) PCT Pub. No.: WO2007/145922

PCT Pub. Date: Dec. 21, 2007

(65) Prior Publication Data

US 2009/0181946 A1 Jul. 16, 2009

Related U.S. Application Data

(60) Provisional application No. 60/812,402, filed on Jun. 9, 2006.

(51) Int. Cl.
*C07D 223/16* (2006.01)
*A61K 31/55* (2006.01)
*A61P 29/02* (2006.01)

(52) U.S. Cl. .................................. 514/212.07; 540/523

(58) Field of Classification Search ................. 540/523; 514/212.07
See application file for complete search history.

(56) References Cited

U.S. PATENT DOCUMENTS 5,310,737 A 5/1994 Fisher et al.

OTHER PUBLICATIONS

J. J. Clare et al., "Voltage-Gated Sodium Channels as Therapeutic Targets", 2000, vol. 5, pp. 506-520, Drug Discovery Today.

W. A. Catterall, "Structure and Function of Voltage-Gated Sodium and Calcium Channels", 1991, vol. 1, pp. 5-13, Current Opinion in Neurobiology.

G. T. Carter et al., "Advances in the Management of Neuropathic Pain", 2001, vol. 12, No. 2, pp. 447-459, Physcial Medicine and Rehabilitation Clinics of North America.

M. D. Baker et al., "Involvement of Na Channels in Pain Pathways", 2001, vol. 22, No. 1, pp. 27-31, Trends in Pharmacological Sciences.

J. Mao et al., "Systemic Lidocaine for Neuropathic Pain Relief ", 2000, vol. 87, pp. 7-17, Pain.

D. L. Tanelian et al., "Neuropathic Pian can be Relieved by Drugs that are Use-Dependent Sodium Channel Blockers: Lidocaine, Carbamazepine and Mexiletine", 1991, vol. 74, No. 5, pp. 949-951.

T. Anger et al., "Medicinal Chemistry of neuronal Voltage-Gated Sodium Channel Blockers", 2001, vol. 44, No. 2, pp. 115-137, J. of Medicinal Chemistry.

A. Devers et al., "Topical Lidocaine Patch Relieves a Variety of Neuropathic Pain Conditions: An Openlabel Study", 2000, vol. 16, No. 3, pp. 205-208, Clinical J. of Pain.

J. D. Armstrong et al., "An efficient Asymmetric Synthesis of (R)-3-Amino-2,3,4,5-Tetrahydro-1H-{1}-Benzaepin-2-one", 1994, vol. 35, pp. 3239-3242, Tetrahedron Letters.

R. M. Williams et al., "Asymmetric Synthesis of Monosubstituted and Alpha, Alpha-Disubstituted Alpha-Amino Acids via Diasteroselective Glycine Enolate Alkylations", 1991, vol. 113, pp. 9276-9286.

U. Schollkoff, "Enantioselective Synthesis of Non-Proteinogenic Amino Acids Via Metallated Bis-Lactim Ethers of 2,5-Diketopiperazines", 1983, vol. 39, pp. 2085-2091, Tetrahedron.

C. Y. Chang et al., "Synthesis of Optically Active Alpha-Aminobenzolactam Via an Oxidative-Cyclization Reaction", 2003, vol. 14, pp. 2081-2085, Tetrahedron: Asymmetry.

J. K. Stille, "The Palladium-Catalyzed Cross-Coupling Reactions of Organotin Reagents with Organic Electrophiles" 1986, vol. 25, pp. 508-524, Angewante Chemie Internationa Edition in English.

L. Jiang et al., "Copper-Catazlysed Coupling of Amides and Carbamates with Vinyl Halides", 2003, vol. 5, pp. 3667-3669, Organic Letters.

M. Takashi et al., "Synthesis of Fused Heterocyclic Compounds and their Inhibitory Activities for Squalence Synthase", 2002, vol. 10, pp. 385-400, Bioorganic & Medicinal Chemistry.

(Continued)

*Primary Examiner*—Bruck Kifle
(74) *Attorney, Agent, or Firm*—Sylvia A. Ayler; Gerard M. Devlin

(57) ABSTRACT

Benzazepinone compounds represented by Formula (I), or pharmaceutically acceptable salts thereof. Pharmaceutical compositions comprise an effective amount of the instant compounds, either alone, or in combination with one or more other therapeutically active compounds, and a pharmaceutically acceptable carrier. Methods of treating conditions associated with, or caused by, sodium channel activity, including, for example, acute pain, chronic pain, visceral pain, inflammatory pain, neuropathic pain, epilepsy, irritable bowel syndrome, urinary incontinence, pruritis, itchiness, allergic dermatitis, depression, anxiety, multiple sclerosis, and bipolar disorder, comprise administering an effective amount of the present compounds, either alone, or in combination with one or more other therapeutically active compounds. A method of administering local anesthesia comprises administering an effective amount of a compound of the instant invention, either alone, or in combination with one or more other therapeutically active compounds, and a pharmaceutically acceptable carrier.

21 Claims, No Drawings

OTHER PUBLICATIONS

K. Hino et al., "A Novel Class of Potential Central Nervous System Agents. 3-Phenyl-2-(1-Piperazinyl)-5H-1 Benzaepines.", 1988, vol. 31, pp. 107-117, J. of Medicinal Chemistry.

M. B. Van Niel et al., "CCKB Selective Receptor Ligands: NOvel 1,3,5-Trisubstituted Benzazepin-2-Ones", 1995, vol. 5, pp. 1421-1426, Bioorganic & Medicinal Chemistry Letters.

W. J. Middleton, "New Fluroinating Reagents. Dialkylaminosulfur Fluorides", 1975, vol. 40, pp. 574-578., J. of Organic Chemistry.

BENZAEPINONES AS SODIUM CHANNEL BLOCKERS

CROSS REFERENCE TO RELATED APPLICATIONS

This application is the National Stage of International Application No. PCT/US2007/013202 filed on Jun. 5, 2007, which claims the benefit under 35 U.S.C. 119(e) of U.S. Provisional Application No. 60/812,402 filed Jun. 9, 2006.

FIELD OF THE INVENTION

The present invention is directed to a series of benzazepinone compounds. In particular, this invention is directed to benzazepinones that are sodium channel blockers useful for the treatment of chronic and neuropathic pain. The compounds of the present invention are also useful for the treatment of other conditions, including pruritis, itchiness, allergic dermatitis, and disorders of the nervous system such as postherpetic neuralgia, diabetic neuropathy, epilepsy, manic depression, bipolar disorder, depression, anxiety and urinary incontinence.

BACKGROUND OF THE INVENTION

Voltage-gated ion channels allow electrically excitable cells to generate and propagate action potentials and therefore are crucial for nerve and muscle function. Sodium channels play a special role by mediating rapid depolarization, which constitutes the rising phase of the action potential and in turn activates voltage-gated calcium and potassium channels. Voltage-gated sodium channels represent a multigene family. Nine sodium channel subtypes have been cloned and functionally expressed to date. [Clare, J. J., Tate, S. N., Nobbs, M. & Romanos, M. A. Voltage-gated sodium channels as therapeutic targets. *Drug Discovery Today* 5, 506-520 (2000)]. They are differentially expressed throughout muscle and nerve tissues and show distinct biophysical properties. All voltage-gated sodium channels are characterized by a high degree of selectivity for sodium over other ions and by their voltage-dependent gating. [Catterall, W. A. Structure and function of voltage-gated sodium and calcium channels. *Current Opinion in Neurobiology* 1, 5-13 (1991)]. At negative or hyperpolarized membrane potentials, sodium channels are closed. Following membrane depolarization, sodium channels open rapidly and then inactivate. Sodium channels only conduct currents in the open state and, once inactivated, have to return to the resting state, favored by membrane hyperpolarization, before they can reopen. Different sodium channel subtypes vary in the voltage range over which they activate and inactivate as well as in their activation and inactivation kinetics.

Sodium channels are the target of a diverse array of pharmacological agents, including neurotoxins, antiarrhythmics, anticonvulsants and local anesthetics. [Clare, J. J., Tate, S. N., Nobbs, M. & Romanos, M. A. Voltage-gated sodium channels as therapeutic targets. *Drug Discovery Today* 5, 506-520 (2000)]. Several regions in the sodium channel secondary structure are involved in interactions with these blockers and most are highly conserved. Indeed, most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrigine, phenyloin and carbamazepine) and certain cardiac arrhythmias (e.g. lignocaine, tocainide and mexiletine).

It is well known that the voltage-gated $Na^+$ channels in nerves play a critical role in neuropathic pain. Injuries of the peripheral nervous system often result in neuropathic pain persisting long after the initial injury resolves. Examples of neuropathic pain include, but are not limited to, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. It has been shown in human patients as well as in animal models of neuropathic pain, that damage to primary afferent sensory neurons can lead to neuroma formation and spontaneous activity, as well as evoked activity in response to normally innocuous stimuli. [Carter, G. T. and B. S. Galer, *Advances in the management of neuropathic pain*. Physical Medicine and Rehabilitation Clinics of North America, 2001. 12 (2): p. 447-459]. The ectopic activity of normally silent sensory neurons is thought to contribute to the generation and maintenance of neuropathic pain. Neuropathic pain is generally assumed to be associated with an increase in sodium channel activity in the injured nerve. [Baker, M. D. and J. N. Wood, *Involvement of Na channels in pain pathways*. TRENDS in Pharmacological Sciences, 2001. 22 (1): p. 27-31].

Indeed, in rat models of peripheral nerve injury, ectopic activity in the injured nerve corresponds to the behavioral signs of pain. In these models, intravenous application of the sodium channel blocker and local anesthetic lidocaine can suppress the ectopic activity and reverse the tactile allodynia at concentrations that do not affect general behavior and motor function. [Mao, J. and L. L. Chen, *Systemic lidocaine for neuropathic pain relief*. Pain, 2000. 87: p. 7-17]. These effective concentrations were similar to concentrations shown to be clinically efficacious in humans. [Tanelian, D. L. and W. G. Brose, *Neuropathic pain can be relieved by drugs that are use-dependent sodium channel blockers: lidocaine, carbamazepine and mexiletine*. Anesthesiology, 1991. 74 (5): p. 949-951]. In a placebo-controlled study, continuous infusion of lidocaine caused reduced pain scores in patients with peripheral nerve injury, and in a separate study, intravenous lidocaine reduced pain intensity associated with postherpetic neuralgia (PHN). [Mao, J. and L. L. Chen, *Systemic lidocaine for neuropathic pain relief*. Pain, 2000. 87: p. 7-17. Anger, T., et al., *Medicinal chemistry of neuronal voltage-gated sodium channel blockers*. Journal of Medicinal Chemistry, 2001. 44 (2): p. 115-137]. Lidoderm®, lidocaine applied in the form of a dermal patch, is currently the only FDA approved treatment for PHN. [Devers, A. and B. S. Galer, *Topical lidocaine patch relieves a variety of neuropathic pain conditions: an open-label study*. Clinical Journal of Pain, 2000. 16 (3): p. 205-208].

In addition to neuropathic pain, sodium channel blockers have clinical uses in the treatment of epilepsy and cardiac arrhythmias. Recent evidence from animal models suggests that sodium channel blockers may also be useful for neuroprotection under ischaemic conditions caused by stroke or neural trauma and in patients with multiple sclerosis (MS). [Clare, J. J., et al. And Anger, T., et al].

SUMMARY OF THE INVENTION

The present invention is directed to benzazepinone compounds which are sodium channel blockers useful for the treatment of chronic and neuropathic pain. The compounds of the present invention are also useful for the treatment of other conditions, including urinary incontinence, pruritis, itchiness, allergic dermatitis, and disorders of the CNS such as anxiety, depression, epilepsy, manic depression and bipolar disorder. This invention also provides pharmaceutical compositions comprising a compound of the present invention, either alone, or in combination with one or more therapeutically active compounds, and a pharmaceutically acceptable carrier.

This invention further comprises methods for the treatment of acute pain, chronic pain, visceral pain, inflammatory pain, neuropathic pain and disorders of the CNS including, but not limited to, epilepsy, manic depression, depression, anxiety and bipolar disorder comprising administering the compounds and pharmaceutical compositions of the present invention.

DETAILED DESCRIPTION OF THE INVENTION

The present invention comprises compounds represented by formula I:

(I)

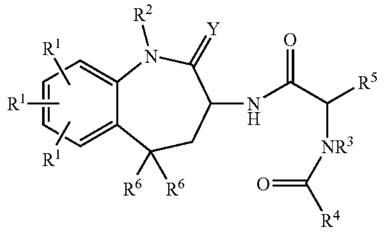

and pharmaceutically acceptable salts and individual stereoisomers thereof, wherein $R^1$ is selected from the group consisting of
- hydrogen,
- halogen,
- cyano,
- $C_{1-6}$ alkyl, unsubstituted or substituted with one to five halogens, and
- —O—$C_{1-6}$ alkyl, unsubstituted or substituted with one to five halogens;

Y is O or $H_2$;

$R^2$ is selected from the group consisting of
- hydrogen,
- $C_{1-6}$ alkyl, unsubstituted or substituted with one to six halogens,
- $C_{1-6}$ alkenyl,
- $C_{1-6}$ alkynyl,
- $C_{1-6}$ alkoxy-$C_{1-6}$ alkyl, unsubstituted or substituted with one to six halogens, and
- $C_{3-6}$ cycloalkyl-$C_{0-6}$alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens;

$R^3$ is selected from the group consisting of
- Hydrogen, and
- $C_{1-6}$ alkyl, unsubstituted or substituted with one to six halogens;

$R^4$ is selected from the group consisting of
- $C_{1-10}$ alkyl, unsubstituted or substituted with one to six halogens,
- —O—$C_{1-10}$ alkyl, unsubstituted or substituted with one to six halogens,

- $C_{3-10}$ cycloalkyl-$C_{0-6}$ alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens,
- $(CH_2)_n$-aryl, wherein aryl is unsubstituted or substituted with one to five substituents independently selected from halogen, cyano, $C_{1-6}$ alkyl and $C_{1-6}$ alkoxy, wherein alkyl and alkoxy are unsubstituted or substituted with one to six halogens, and
- $(CH_2)_n$-heteroaryl, wherein heteroaryl is unsubstituted or substituted with one to five substituents independently selected from halogen, $C_{1-6}$ alkyl and $C_{1-6}$ alkoxy, wherein alkyl and alkoxy are unsubstituted or substituted with one to six halogens;

$R^5$ is selected from the group consisting of
- $(CH_2)_n$-aryl, wherein aryl is unsubstituted or substituted with one to five substituents independently selected from hydroxy, halogen, cyano, $C_{1-6}$ alkyl and $C_{1-6}$ alkoxy, wherein alkyl and alkoxy are unsubstituted or substituted with one to six halogens, and
- $(CH_2)_n$-heteroaryl, wherein heteroaryl is unsubstituted or substituted with one to five substituents independently selected from halogen, $C_{1-6}$ alkyl and $C_{1-6}$ alkoxy, wherein alkyl and alkoxy are unsubstituted or substituted with one to six halogens;

$R^6$ is selected from the group consisting of
- Hydrogen, and
- halogen;

n is 0, 1 or 2.

Further embodiments of the present invention include compounds of Formula Ia (Ia)

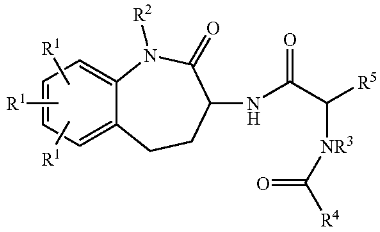

wherein $R^1$, $R^2$, $R^3$, $R^4$ and $R^5$ are as defined in Formula I, and pharmaceutically acceptable salts and individual stereoisomers thereof.

In a class of this embodiment of the present invention are compounds of Formula Ib, where the carbon atom marked with an * has the stereochemical configuration as depicted below:

(Ib)

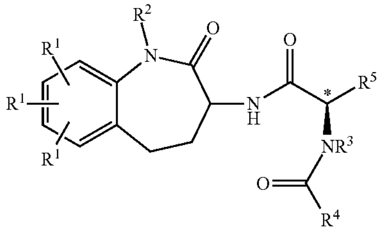

wherein $R^1$, $R^2$, $R^3$, $R^4$ and $R^5$ are as defined in Formula I, and pharmaceutically acceptable salts and individual stereoisomers thereof.

Additional embodiments of the present invention include compounds of Formula Ic (Ic)

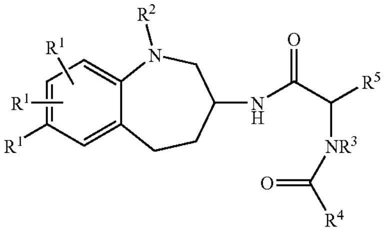

wherein $R^1$, $R^2$, $R^3$, $R^4$ and $R^5$ are as defined in Formula I, and pharmaceutically acceptable salts and individual stereoisomers thereof.

In a class of this embodiment of the present invention the carbon atoms marked with * and ** have the stereochemical configurations as depicted in Formula Id (Id)

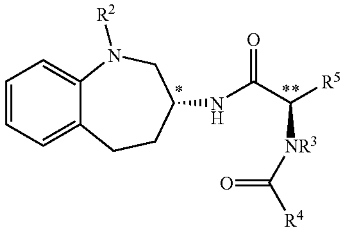

wherein $R^2$, $R^3$, $R^4$ and $R^5$ are as defined in Formula I, and pharmaceutically acceptable salts and individual stereoisomers thereof.

Additional embodiments of the present invention include compounds of Formula Ie (Ie)

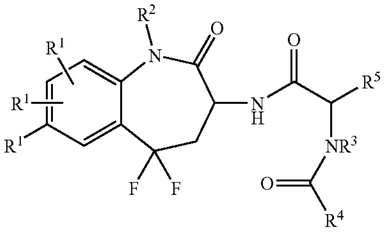

wherein $R^1$, $R^2$, $R^3$, $R^4$ and $R^5$ are as defined in Formula I, and pharmaceutically acceptable salts and individual stereoisomers thereof.

In a class of this embodiment of the present invention, the carbon atom marked with an * has the stereochemical configuration as depicted in Formula If (If)

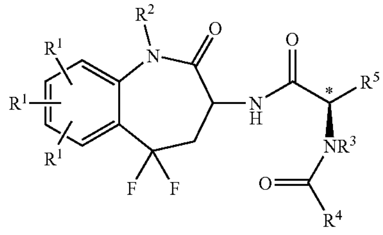

wherein $R^1$, $R^2$, $R^3$, $R^4$ and $R^5$ are as defined in Formula I, and pharmaceutically acceptable salts and individual stereoisomers thereof.

Additional embodiments of the present invention include compounds of Formula Ig (Ig)

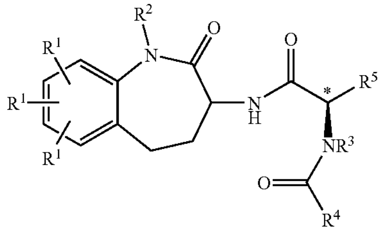

wherein $R^2$ is selected from the group consisting of:

$C_{1-6}$ alkyl, unsubstituted or substituted with one to six halogens, and $C_{3-6}$ cycloalkyl-$C_{0-6}$alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens, and $R^1$, $R^3$, $R^4$, and $R^5$ are as defined in Formula I, and pharmaceutically acceptable salts and individual stereoisomers thereof.

Additional embodiments of the present invention include compounds of Formula Ih

Ih

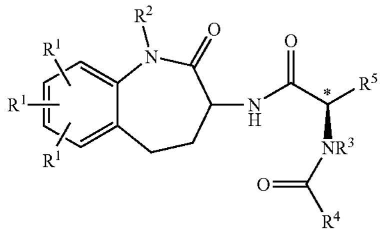

wherein $R^5$ is $(CH_2)_n$-aryl, wherein said aryl is unsubstituted or substituted with one to five substituents independently selected from hydroxy, halogen, cyano, $C_{1-6}$ alkyl and $C_{1-6}$ alkoxy, wherein alkyl and alkoxy are unsubstituted or substituted with one to six halogens, and $R^1$, $R^2$, $R^3$, and $R^4$ are as defined in Formula I, and pharmaceutically acceptable salts and individual stereoisomers thereof.

Additional embodiments of the present invention include compounds of Formula Ii

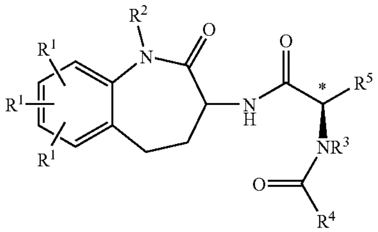

Ii wherein $R^4$ is —O—$C_{1-10}$ alkyl, unsubstituted or substituted with one to six halogens, or $(CH_2)_n$-aryl, wherein said aryl is unsubstituted or substituted with one to five substituents independently selected from halogen, cyano, $C_{1-6}$ alkyl and $C_{1-6}$ alkoxy, wherein alkyl and alkoxy are unsubstituted or substituted with one to six halogens, and $R^1$, $R^2$, $R^3$, and $R^5$ are as defined in Formula I, and pharmaceutically acceptable salts and individual stereoisomers thereof.

Illustrative, but nonlimiting, examples of compounds of the present invention that are useful as sodium channel blockers are the following:

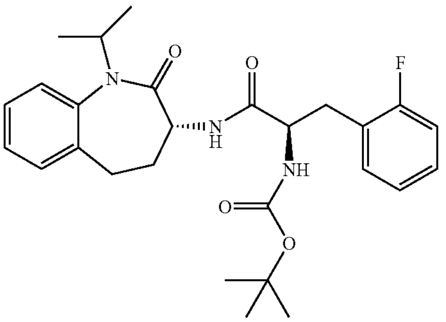

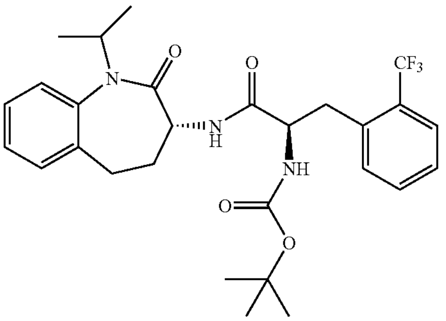

-continued

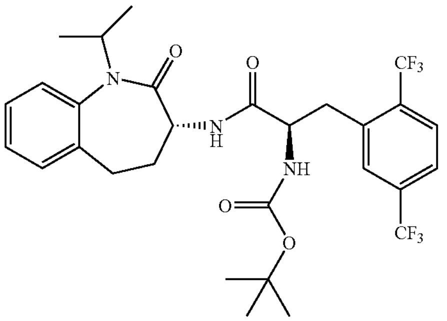

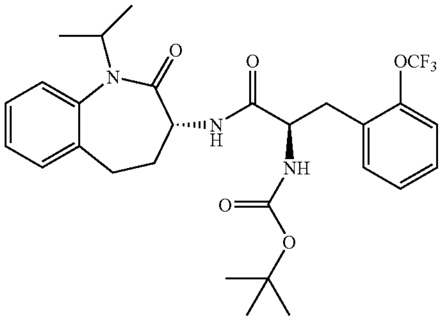

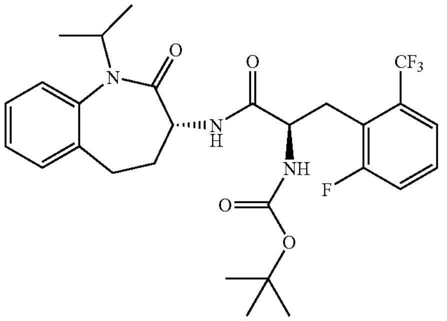

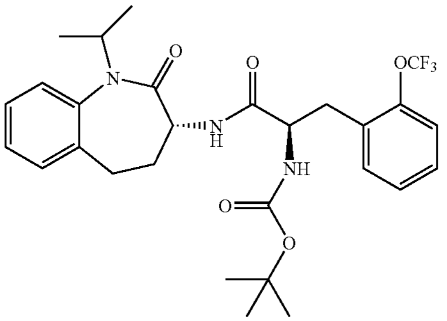

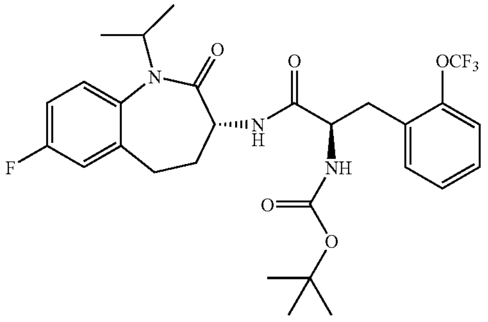

-continued
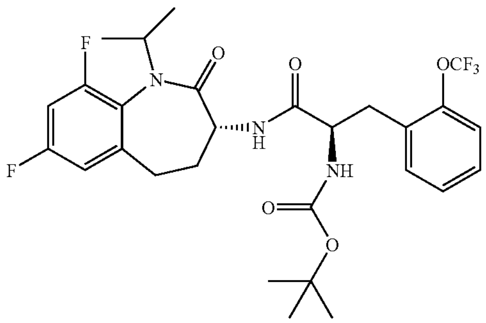
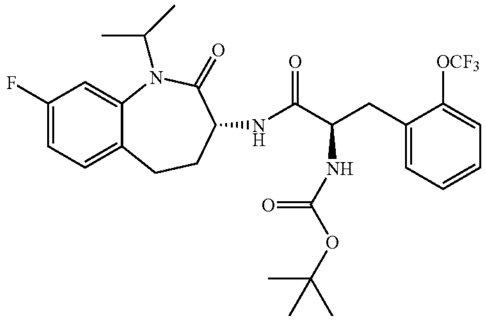
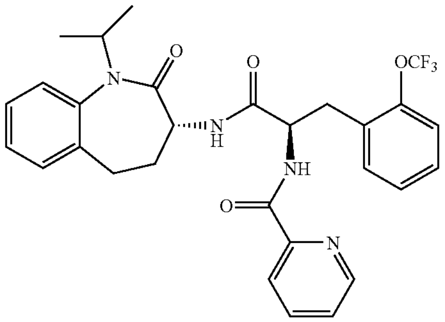
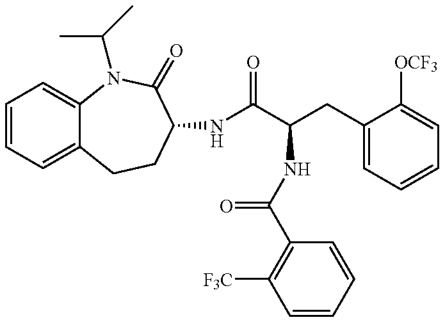
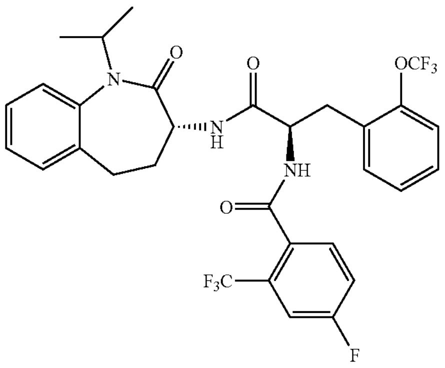
-continued
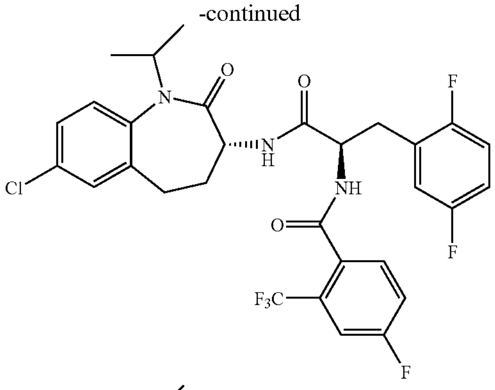
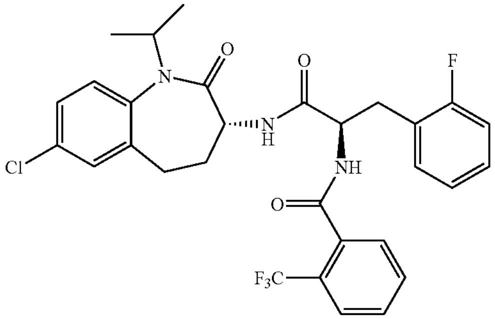
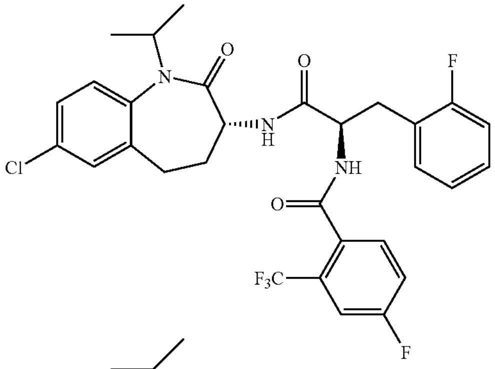
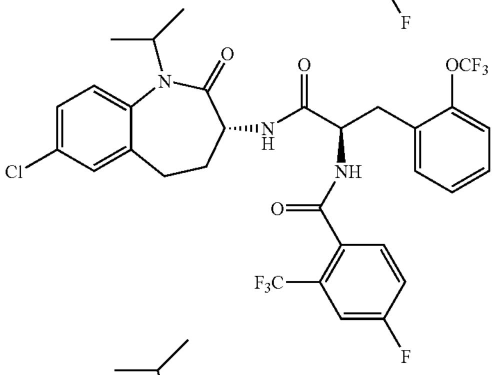
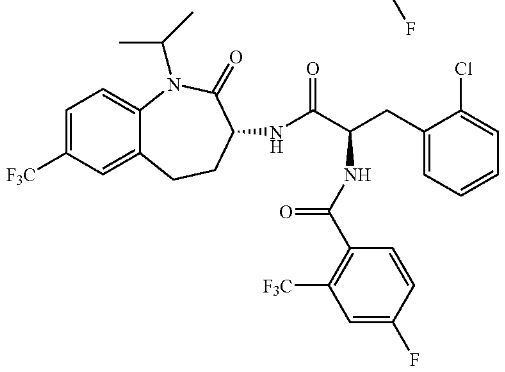

-continued
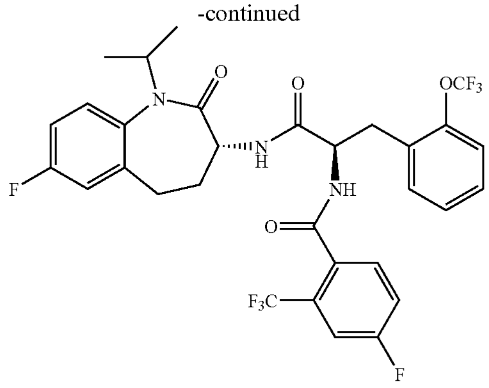
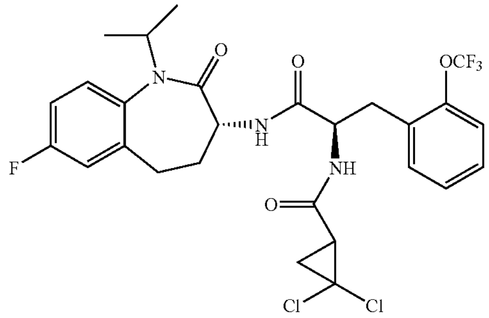
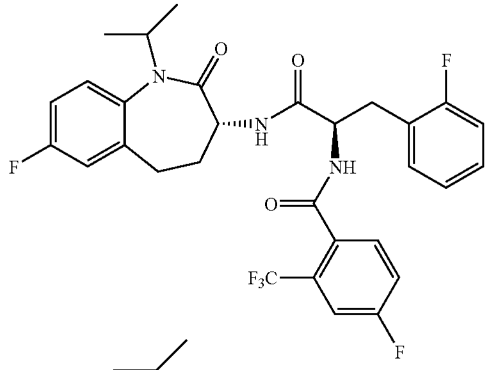
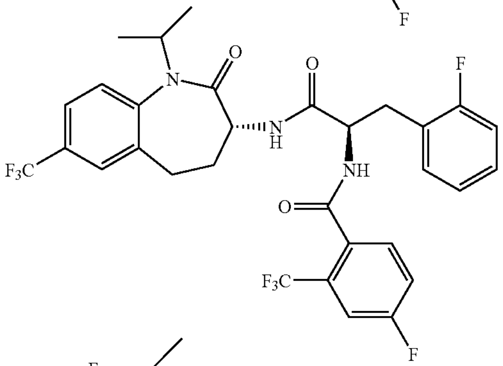
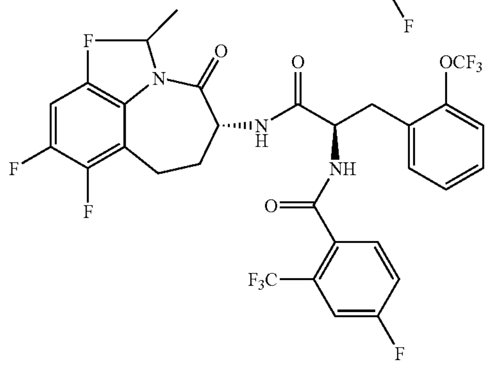
-continued
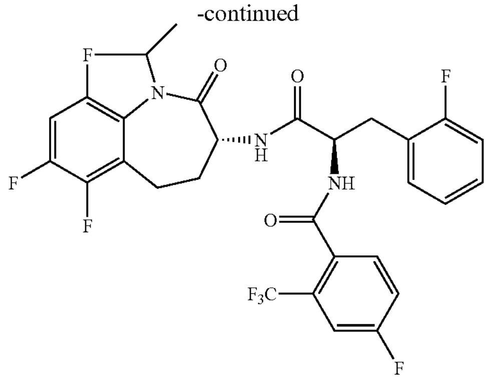
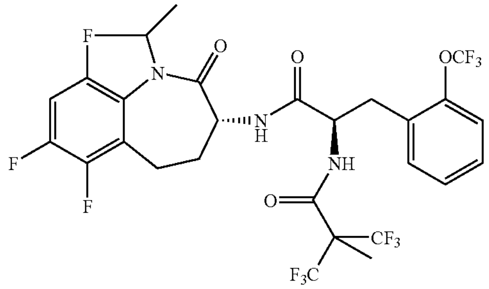
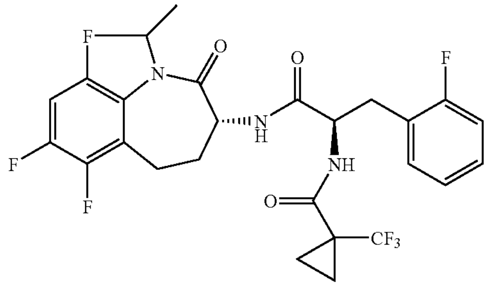
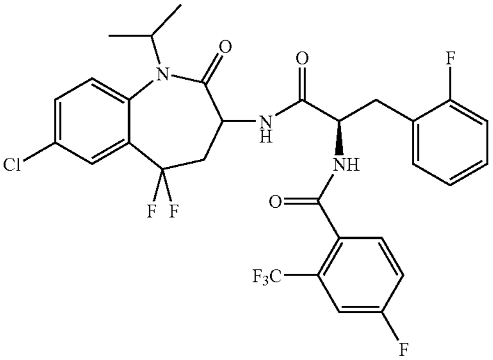
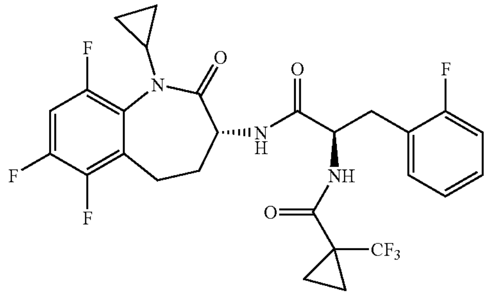
The term "alkyl" means carbon chains that have no double or triple bonds, and that may be linear or branched or combinations thereof. Thus, $C_1$-$C_6$ alkyl is defined to identify the group as having 1, 2, 3, 4, 5 or 6 carbons in an arrangement that is linear, branched, or a combination thereof. Examples of alkyl groups include methyl, ethyl, propyl, n-propyl, isopropyl, butyl, sec- and tert-butyl, pentyl, hexyl, heptyl and the like. The term "$C_0$-$C_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "alkene" means linear or branched structures and combinations thereof, of the indicated number of carbon atoms, having at least one carbon-to-carbon double bond, wherein hydrogen may be replaced by an additional carbon-to-carbon double bond. $C_2$-$C_6$ alkene, for example, includes ethylene, propylene, 1-methylethylene, butylene and the like.

The term "alkynyl" means linear or branched structures and combinations thereof, of the indicated number of carbon atoms, having at least one carbon-to-carbon triple bond. Thus $C_2$-$C_6$ alkynyl is defined to identify the group as having 2, 3, 4, 5 or 6 carbon in a linear or branched arrangement, such that $C_2$-$C_6$ alkynyl specifically includes 2-hexynyl and 2-pentynyl.

The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

"Aryl" means a mono or polycyclic aromatic ring system containing carbon ring atoms. Advantageously, the aryls are mono or bicyclic 6-10 membered aromatic systems. More advantageously, the aryls are phenyl and naphthyl.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms.

Examples of heterocycloalkyl include azetidinyl, pyrrolidinyl, piperidinyl, piperazinyl, morpholinyl, tetrahydrofuranyl, imidazolinyl, cyclic acetals, cyclic ketals, pyrrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl", as used herein except where noted, is intended to mean a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

"Halogen" means fluorine, chlorine, bromine and iodine. Advantageously, the halogen is fluorine or chlorine.

The term "mammal" "mammalian" or "mammals" includes humans, as well as animals, such as dogs, cats, horses, pigs and cattle.

It is to be understood that where one or more of the above recited structures or substructures recite multiple substituents having the same designation, each such substituent may be the same or different from each similarly designated substituent. For example, $R^1$ is recited three times in Formula I, and each $R^1$ in Formula I may independently be any of the substructures or variables defined under $R^1$. The invention is not limited to structures and substructures wherein each $R^1$ must be the same for a given structure. The same is true with respect to any variable appearing multiple times in a structure or substructure.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention contain one or more asymmetric centers and may thus occur as racemates, racemic mixtures, single enantiomers, diastereomeric mixtures, and individual diastereomers. In particular the compounds of the present invention have an asymmetric center at the sterogenic carbon atoms marked with an * and ** in formulae Ib, Id, and If. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodologies disclosed herein. Their absolute stereochemistry may be determined by X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as by chromatographic methods utilizing chiral stationary phases.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, and xiv) neurontin (gabapentin). The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention can also be utilized as local anesthetics. Compounds of this invention are useful for the treatment of irritable bowel syndrome and related disorders, as well as Crohn's disease and urinary incontinence. The instant compounds can also be used to treat pruritis, itchiness, and allergic dermatitis.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

In addition to primates, such as humans, a variety of other mammals can be treated according to the method of the present invention. For instance, mammals including, but not limited to, cows, sheep, goats, horses, dogs, cats guinea pigs, or other bovine, ovine, equine, canine, feline, rodent such as mouse, species can be treated. However, the method can also be practiced in other species, such as avian species (e.g., chickens).

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical anti-depressants, benzodiazepines, 5-$HT_{1A}$ agonists or antagonists, especially 5-$HT_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with sodium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I, Ia, Ib, Id or Ie. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose; diluents, granulating agents, lubricants, binders, and disintegrating agents can be used to form oral solid preparations such as powders, capsules and tablets. Because of their ease of administration, tablets and capsules can be advantageously employed when solid pharmaceutical carriers are used. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet advantageously contains from about 0.1 mg to about 500 mg of the active ingredient and each cachet or capsule advantageously containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion; and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The compounds and pharmaceutical compositions of this invention have been found to block sodium channels. Accordingly, an aspect of the invention is the treatment and prevention in mammals of conditions that are amenable to amelioration through blockage of neuronal sodium channels by administering an effective amount of a compound of this invention. Such conditions include, for example, acute pain, chronic pain, visceral pain, inflammatory pain and neuropathic pain. The instant compounds and compositions are useful for treating and preventing the above-recited conditions, including acute pain, chronic pain, visceral pain, inflammatory pain and neuropathic pain, in humans and non-human mammals such as dogs and cats. It is understood that the treatment of mammals other than humans refers to the treatment of clinical conditions in non-human mammals that correlate to the above-recited conditions.

Further, as described above, the instant compounds can be utilized in combination with one or more therapeutically active compounds. In particular, the inventive compounds can be advantageously used in combination with i) opiate agonists or antagonists, ii) calcium channel antagonists, iii) 5HT receptor agonists or antagonists, including 5-$HT_{1A}$ agonists or antagonists, and 5-$HT_{1A}$ partial agonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, xiv) norepinephrine reuptake inhibitors, xv) monoamine oxidase inhibitors (MAOIs), xvi) reversible inhibitors of monoamine oxidase (RIMAs), xvii) alpha-adrenoreceptor antagonists, xviii) atypical anti-depressants, xix) benzodiazepines, xx) corticotropin releasing factor (CRF) antagonists, xxi) gabapentin, and xxii) pregabalin.

The abbreviations used herein have the following meanings (abbreviations not shown here have their meanings as commonly used unless specifically stated otherwise): Ac (acetyl), Bn (benzyl), Boc (tertiary-butoxy carbonyl), CAMP (cyclic adenosine-3',5'-monophosphate), DAST ((diethylamino)sulfur trifluoride), DBU (1,8-diazabicyclo[5.4.0]undec-7-ene), DIBAL (diisobutylaluminum hydride), DMAP (4-(dimethylamino)pyridine), DMF (N,N-dimethylformamide), EDC (1-(3-dimethylaminopropyl)-3-ethylcarbodiimide hydrochloride), $Et_3N$ (triethylamine), GST (glutathione transferase), HOBt (1-hydroxybenzotriazole), LAH (lithium aluminum hydride), Ms (methanesulfonyl; mesyl; or $SO_2Me$), MsO (methanesulfonate or mesylate), NBS (N-bromosuccinimide), NCS (N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or $SO_2NH_2$), SPA (scintillation proximity assay), Tb (2- or 3-thienyl), TFA (trifluoroacetic acid), THF (Tetrahydrofuran), Thi (Thiophenediyl), TLC (thin layer chromatography), TMEDA (N,N,N',N'-tetramethylethylenediamine), TMSI (trimethylsilyl iodide), Tr or trityl (N-triphenylmethyl), $C_3H_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the general Schemes provided below as well as the procedures provided in the Examples. The following Schemes and Examples further describe, but do not limit, the scope of the invention.

Unless specifically stated otherwise, the experimental procedures were performed under the following conditions: All operations were carried out at room or ambient temperature; that is, at a temperature in the range of 18-25° C. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (N) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry, March,* 5th Ed., John Wiley and Sons, New York, N.Y., 2001; *Advanced Organic Chemistry*, Carey and Sundberg, Vol. A and B, 3rd Ed., Plenum Press, Inc., New York, N.Y., 1990; *Protective groups in Organic Synthesis*, Green and Wuts, 2nd Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2nd Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1H$ and $^{13}C$ NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, diethyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-butyllithium, phenyllithium, alkyl magnesium halides, organic bases such as trimethylamine, triethylamine, triisopropylamine, N,N-diisopropylethylamine, piperidine, N-methyl piperidine, morpholine, N-methyl morpholine, pyridine, collidines, lutidines, and 4-dimethylaminopyridine; and bicyclic amines such as DBU and DABCO.

As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

It is understood that the functional groups present in compounds described in the Schemes below can be further manipulated, when appropriate, using the standard functional group transformation techniques available to those skilled in the art, to provide desired compounds described in this invention.

It is also understood that compounds listed in the Schemes and Tables below that contain one or more stereocenters may be prepared as single enantiomers or diastereomers, or as mixtures containing two or more enantiomers or diastereomers in any proportion.

Other variations or modifications, which will be obvious to those skilled in the art, are within the scope and teachings of this invention. For instance, in some cases, the order of carrying out the foregoing reaction schemes and procedures can be varied to facilitate the reaction or to avoid unwanted reaction products. The following examples are provided so that the invention might be more fully understood. These examples are illustrative only and should not be construed as limiting the invention in any way.

Scheme 1

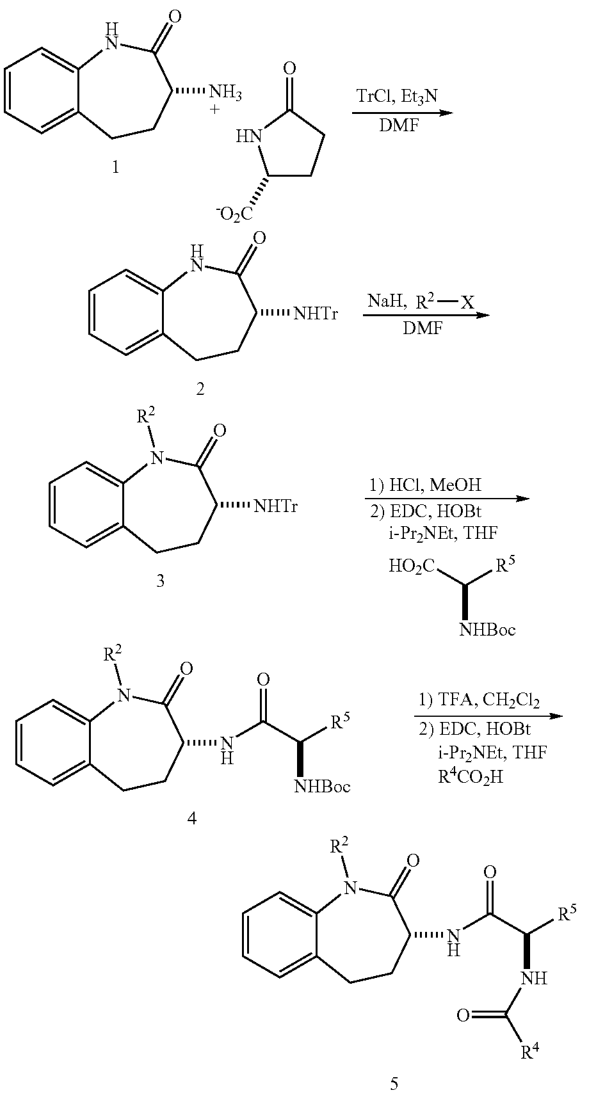

Scheme 1 summarizes one protocol for the preparation of compounds of formula Ia. The initial starting material, 3(R)-Amino-2,3,4,5-tetrahydro-1H-[1]-benzazepin-2-one D-pyroglutamic acid salt 1, can be prepared according to procedures described by Armstrong and coworkers [Armstrong, J. D., Eng, K. K., Keller, J. L., Purick, R. M., Hartner, F. W., Choi, W-B., Askin, D., Volante, R. P. An efficient asymmetric synthesis of (R)-3-amino-2,3,4,5-tetrahydro-1H-[1]-benzazepin-2-one. *Tetrahedron Letters* 35, 3239-3242 (1994)]. Amine salt 1 can be converted to its NA-triphenylmethyl (trityl) derivative by reaction with trityl chloride in the presence of a base such as triethylamine ($Et_3N$) in a solvent such as N,N-dimethylformamide (DMF), at temperatures ranging from room temperature to 120° C. Reaction of the N-trityl derivative 2 with a base such as sodium hydride in an aprotic solvent such as N,N-dimethylformamide (DMF) or tetrahydrofuran (THF) at room temperature or with gentle heating followed by addition of an electrophile $R^2$—X wherein X is a halide, tosylate, mesylate, or a similar leaving group then provides compound 3. The amine group of compound 3 can be deprotected on exposure to an acid such as HCl in a solvent such as methanol to give an intermediate amine hydrochloride salt. A solution of that intermediate salt in a solvent such as tetrahydrofuran can then be treated with an N-Boc protected amino acid in the presence of an activating agent such as 1-[3-(dimethylamino)propyl]-3-ethylcarbodiimide hydrochloride (EDC), an additive such as 1-hydroxybenzotriazole (HOBt) and a base such as diisopropylethylamine to give coupled product 4. The N-Boc protected amino acids used in this coupling reaction can either be obtained from commercial sources or synthesized via the method of Williams and coworkers [Williams, R. M., Myeong-Nyeo, I. Asymmetric synthesis of monosubstituted and alpha, alpha-disubstituted alpha-amino acids via diastereoselective glycine enolate alkylations. *Journal of the American Chemical Society* 113, 9276-9286 (1991)] or the method of Schollkopf [Schollkopf, U. Enantioselective synthesis of non-proteinogenic amino acids via metallated bis-lactim ethers of 2,5-diketopiperazines. *Tetrahedron* 39, 2085-2091 (1983), and references contained therein]. To further elaborate compounds of the present invention, the protecting group of 4 can be removed by reaction with an acid such as trifluoroacetic acid (TFA) in a solvent such as tetrahydrofuran or dichloromethane to give the corresponding amine. This amine could then be coupled with the appropriate commercially available carboxylic acid or acid chloride according to procedures already described to give compound 5. Note that 3(S)-amino-2,3,4,5-tetrahydro-1H-[1]-benzazepin-2-one, the enantiomer of the free base of 1, can be prepared according to the method of Chang and coworkers [Chang, C.-Y., Yang, T.-K. Synthesis of optically active α-aminobenzolactam via an oxidative-cyclization reaction. *Tetrahedron: Asymmetry* 14, 2081-2085 (2003)], while racemic 3-amino-2,3,4,5-tetrahydro-1H-[1]-benzazepin-2-one is commercially available. These materials may be substituted for 1 and then processed as noted above to yield analogs of 5 with S or R,S stereochemistry at the 3-amino stereocenter.

Scheme 2

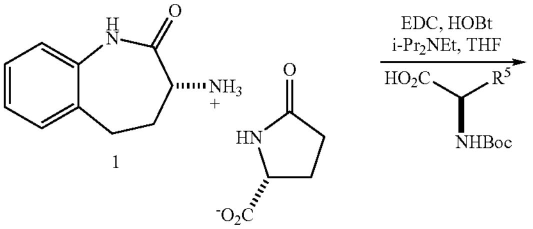

1

-continued

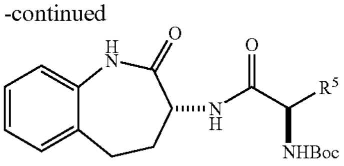

6

An alternate method for the preparation of compounds of formula Ia is shown in Scheme 2. In this approach, 3(R)-Amino-2,3,4,5-tetrahydro-1H-[1]-benzazepin-2-one D-pyroglutamic acid salt 1 can be coupled with an N-Boc protected amino acid in the presence of an activating agent such as 1-[3-(dimethylamino)propyl]-3-ethylcarbodiimide hydrochloride (EDC), an additive such as 1-hydroxybenzotriazole (HOBt) and a base such as diisopropylethylamine in a solvent such at tetrahydrofuran (THF) to give coupled product 6. The N-Boc protected amino acids used in this reaction can either be obtained from commercial sources or synthesized via the methods of Williams or Schollkopf noted above. Note that 3(S)-amino-2,3,4,5-tetrahydro-1H-[1]-benzazepin-2-one can be prepared according to the method of Chang and coworkers described in Scheme 1, and racemic 3-amino-2,3,4,5-tetrahydro-1H-[1]-benzazepin-2-one is commercially available as noted above. These materials may be substituted for 1 and then carried through the sequence of steps outlined in Scheme 2 to yield analogs of 6 with S or R,S stereochemistry at the 3-amino stereocenter.

Scheme 3

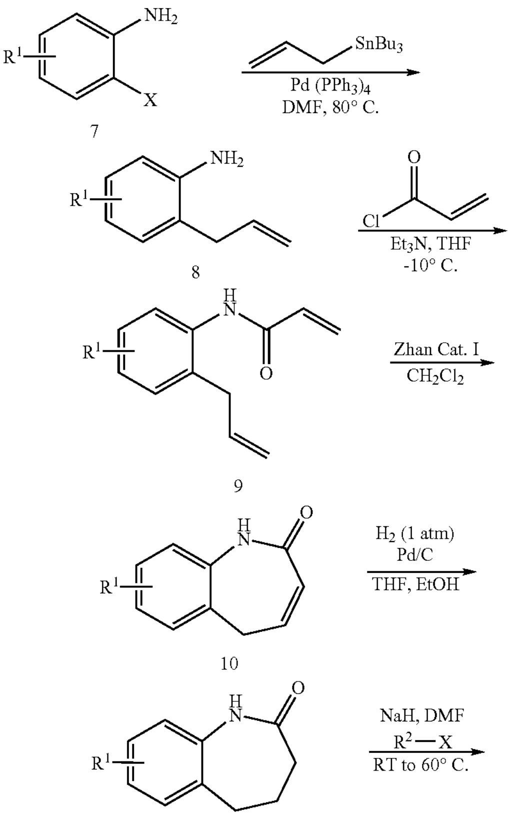

7

8

9

10

11

-continued

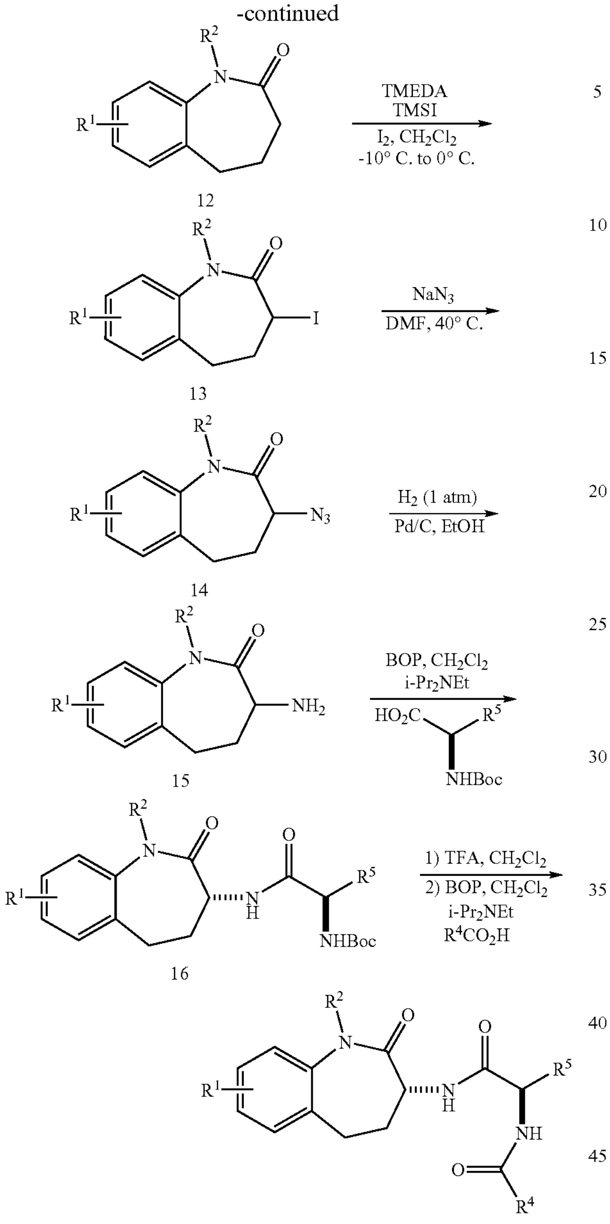

12

13

14

15

16

17

Scheme 3 describes another route to prepare compounds of formula Ia. In this approach, compounds such as 7, wherein X=bromine or iodine, can be heated in the presence of allyl-tributyl tin and a palladium catalyst such as $Pd(PPh_3)_4$ in a solvent such as N,N-dimethylformamide (DMF) to give coupled product 8. [Stille, J. K. The palladium-catalyzed cross-coupling reactions of organotin reagents with organic electrophiles [new synthetic methods (58)] *Angewandte Chemie International Edition in English* 25, 508-524, (1986)] Compound 8 can then be acylated with acryloyl chloride in the presence of a base such as triethylamine in a solvent such as tetrahydrofuran at low temperature to give compound 9. Exposure of 9 to a metathesis catalyst such as Zhan Catalyst I (available from Zannan Pharma, Shanghai, China, catalog #RC-301) in a solvent such as dichloromethane at room temperature afforded cyclized product 10. A solution of compound 10 in solvents such as ethanol and tetrahydrofuran (THF) can then be stirred in the presence of Pd/C catalyst under an atmosphere of hydrogen to give saturated product 11. Reaction of 11 with a base such as sodium hydride in an aprotic solvent such as N,N-dimethylformamide (DMF) or tetrahydrofuran (THF) at room temperature or with gentle heating followed by addition of an electrophile $R^2$—X wherein X is a halide, tosylate, mesylate, or a similar leaving group provides compound 12. Compound 12 can then be elaborated using a modified version of the process developed by Armstrong and coworkers [Armstrong, J. D., Eng, K. K., Keller, J. L., Purick, R. M., Hartner, F. W., Choi, W-B., Askin, D., Volante, R. P. An efficient asymmetric synthesis of (R)-3-amino-2,3,4,5-tetrahydro-1H-[1]-benzazepin-2-one. *Tetrahedron Letters* 35, 3239-3242 (1994)]. Thus, a cooled solution of 12 in a solvent such as dichloromethane can be treated sequentially with N,N,N',N'-tetramethylethylenediamine (TMEDA), iodotrimethylsilane (TMSI) and iodine to yield alpha-iodinated product 13. Mild heating of 13 in a solvent such as N,N-dimethylformamide (DMF) in the presence of sodium azide can then result in displacement of the iodide to give compound 14. A solution of 14 in a solvent such as ethanol can be stirred under an atmosphere of hydrogen in the presence of a catalyst such as Pd/C to give amine 15 which can then be coupled with an N-Boc protected amino acid in the presence of an activating agent such as benzotriazol-1-yloxytris(dimethylamino)phosphonium hexafluorophosphate (BOP) and a base such as diisopropylethylamine in a solvent such as dichloromethane to give coupled product 16. The N-Boc protecting group of 16 can be removed by reaction with an acid such as trifluoroacetic acid (TFA) in a solvent such as tetrahydrofuran or dichloromethane to give the corresponding amine. This amine can then be coupled with a commercially available carboxylic acid in the presence of an activating agent such as benzotriazol-1-yloxytris(dimethylamino)phosphonium hexafluorophosphate (BOP) and a base such as diisopropylethylamine in a solvent such as dichloromethane to give coupled product 17.

Scheme 4

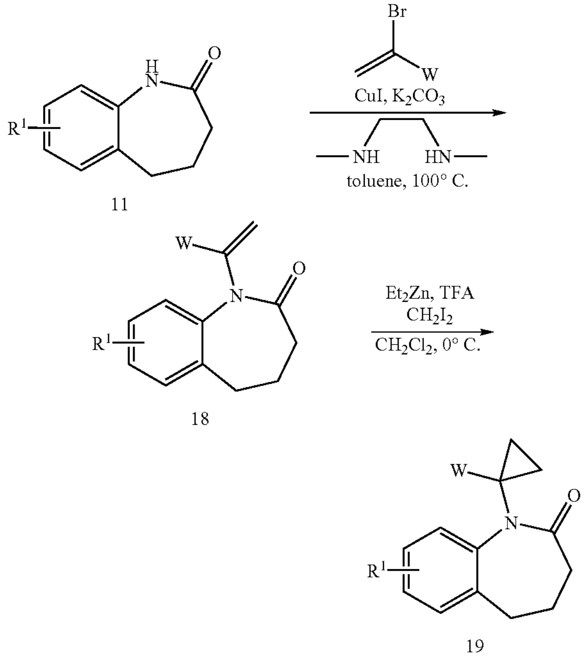

11

18

19

Compounds of formula Ia wherein $R^2$ is cyclopropyl (substituted or unsubstituted) can be prepared as shown in Scheme 4. The first step of this process involves coupling of intermediate 11 with a vinyl bromide according to procedures developed by Buchwald and coworkers [Jiang, L., Job, G. E., Klapars, A., Buchwald, S. L. Copper-catalyzed coupling of amides and carbamates with vinyl halides. *Organic Letters* 5, 3667-3669 (2003)]. Thus, heating of intermediate 11 and a vinyl bromide (W=H or alkyl) in the presence of catalytic amounts of copper iodide (CuI) and N,N'-dimethylethylenediamine and stoichiometric amounts of a base such as potassium carbonate provides coupled product 18. Treatment of 18 with the reagent formed from the combination of diethylzinc, trifluoroacetic acid and diiodomethane effects cyclopropanation to yield 19. Compound 19 can then be elaborated to structures of formula Ia via application of the sequence of steps shown in Scheme 3 for the conversion of compound 12 to compound 17.

Scheme 5

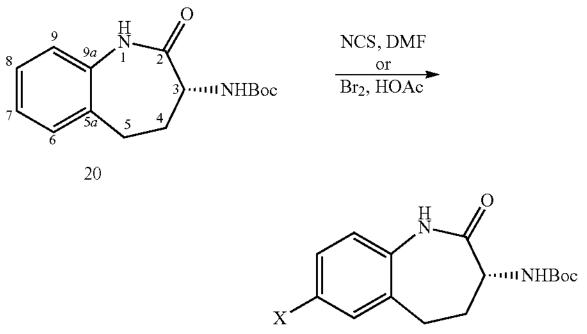

20

21 (X = Cl)
22 (X = Br)

3-Amino-1-benzazepinones containing a chlorine or bromine group at the 7 position can be conveniently prepared as outlined in Scheme 5. Initial compound 20 can be synthesized according to the method described by Armstrong and coworkers [Armstrong, J. D., Eng, K. K., Keller, J. L., Purick, R. M., Hartner, F. W., Choi, W-B., Askin, D., Volante, R. P. An efficient asymmetric synthesis of (R)-3-amino-2,3,4,5-tetrahydro-1H-[1]-benzazepin-2-one. *Tetrahedron Letters* 35, 3239-3242 (1994)]. Exposure of 20 to a chlorinating reagent such as N-chlorosuccinimide (NCS) in a solvent such as N,N-dimethylformamide (DMF) allows for chlorination at the 7 position as described by Takashi and coworkers [Takashi, M., Masakuni, K., Fujishima, A., Mabuchi, H., Tozawa, R., Nakamura, M., Sugiyama, Y., Yukimasa, H. Synthesis of fused heterocyclic compounds and their Inhibitory activities for squalene synthase. *Bioorganic & Medicinal Chemistry* 10, 385-400 (2002)] to give compound 21. Alternatively, treatment of 20 with a brominating reagent such as bromine in a solvent such as glacial acetic acid (HOAc) results in bromination at the 7 position as described by Hino and coworkers [Hino, K., Nagai, Y., Uno, H., Masuad, Y., Oka, M., Karasawa, T. A novel class of potential central nervous system agents. 3-Phenyl-2-(1-piperazinyl)-5H-1-benzazepines. *Journal of Medicinal Chemistry* 31, 107-117 (1988)] to yield compound 22. Compounds 21 and 22 can then be elaborated to structures of formula Ia via application of the sequence of steps shown in Scheme 1 for the conversion of compound 2 to compound 5.

Scheme 6

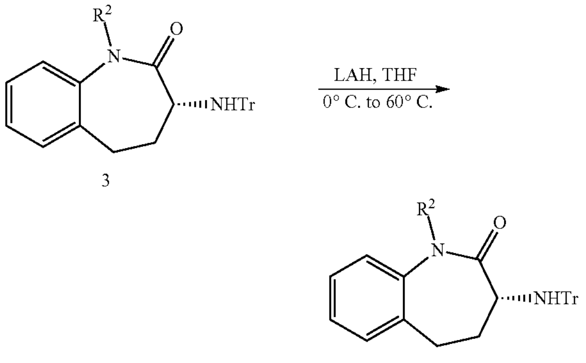

3

23

Compounds of formula Ic can be prepared as shown in Scheme 6. Treatment of compound 3 (from Scheme 1) with a reducing agent such as lithium aluminum hydride (LAH) in a solvent such as tetrahydrofuran (THF) with gradual warming from 0° C. to 60° C. results in reduction of the lactam to give 23. Compound 23 can then be elaborated to structures of formula Ic via application of the sequence of steps shown in Scheme 1 for the conversion of compound 3 to compound 5.

Scheme 7

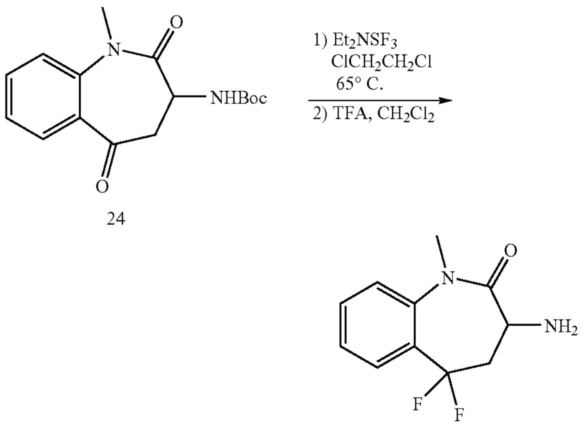

24

25

One method for the synthesis of compounds of formula Ie is outlined in Scheme 7. This route starts from N-Boc protected 3-amino-1-benzazepine-2,5-dione 24, which itself is prepared as described by van Niel and coworkers [van Niel, M. B., Freedman, S. B., Matassa, V. G., Patel, S., Pengilley, R. R., Smith, A. J. $CCK_B$ selective receptor ligands: novel 1,3,5-trisubstituted benzazepin-2-ones. *Bioorganic & Medicinal Chemistry Letters* 5, 1421-1426 (1995)]. Reaction of 24 with (diethylamino)sulfur trifluoride (DAST) in a solvent such as dichloroethane at elevated temperatures as described by Middleton [Middleton, W. J. New fluorinating reagents. Dialkylaminosulfur fluorides. *Journal of Organic Chemistry* 40, 574-578, (1975)] affords a difluorinated intermediate which can then be exposed to an acid such as trifluoroacetic acid (TFA) in a solvent such as dichloromethane to give compound 25. Compound 25 can then be elaborated to structures of formula Ie via application of the sequence of steps shown in Scheme 1 for the conversion of compound 3 to compound 5.

Scheme 8

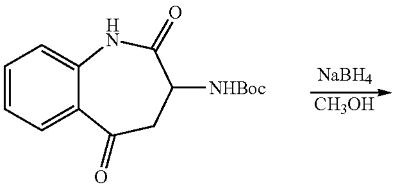

26

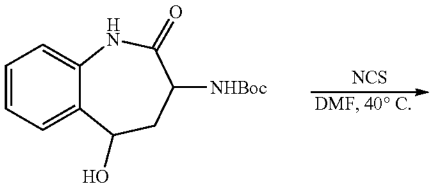

27

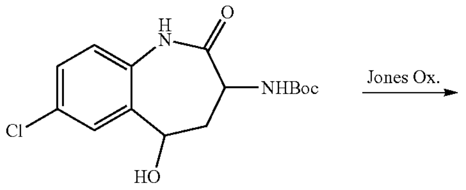

28

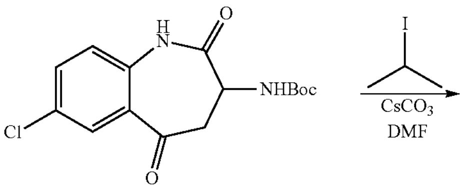

29

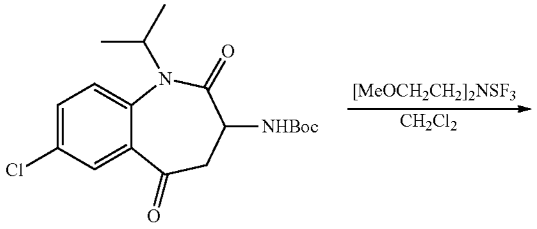

30

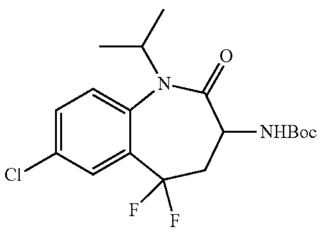

31

Another procedure for the synthesis of compounds of formula Ie is shown in Scheme 8. This route starts from compound 26, which can be prepared by the method of van Niel and coworkers [van Niel, M. B., Freedman, S. B., Matassa, V. G., Patel, S., Pengilley, R. R., Smith, A. J. $CCK_B$ selective receptor ligands: novel 1,3,5-trisubstituted benzazepin-2-ones. *Bioorganic & Medicinal Chemistry Letters* 5, 1421-1426 (1995)]. Ketone 26 can be treated with a reducing agent such as sodium borohydride ($NaBH_4$) in a solvent such as methanol to give alcohol 27. Exposure of 27 to a chlorinating reagent such as N-chlorosuccinimide (NCS) in a solvent such as N,N-dimethylformamide (DMF) at mildly elevated temperature results in regioselective chlorination of the phenyl ring, thereby yielding 28. Oxidation of alcohol 28 with a reagent such as Jones reagent provides ketone 29; treatment of 29 with a base such as cesium carbonate and an electrophile such as 2-iodopropane then allows for selective N-alkylation at the lactam nitrogen to give 30. Finally, exposure of 30 to a fluorinating reagent such as [bis-(2-methoxyethyl)-amino] sulfur trifluoride in a solvent such as dichloromethane affords difluorinated product 31. Compound 31 can then be elaborated to structures of formula Ie via application of the sequence of steps shown in Scheme 1 for the conversion of compound 3 to compound 5.

Example 1

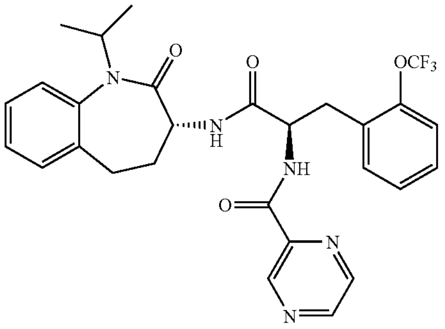

Pyrazine-2-carboxylic acid [(R)-1-((R)-1-isopropyl-2-oxo-2,3,4,5-tetrahydro-1H-1-benzazepin-3-ylcarbamoyl)-2-(2-trifluoromethoxy-phenyl)-ethyl]-amide

Step 1: Preparation of (2S,5R)-2-isopropyl-3,6-dimethoxy-5-(2-trifluoromethoxy-benzyl)-2,5-dihydro-pyrazine

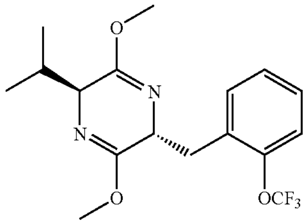

A solution of (2S)-(+)-2,5-dihydro-3,6-dimethoxy-2-isopropylpyrazine (7.2 g, 39.4 mmol) in tetrahydrofuran (50 mL) was cooled to −78° C. A solution of n-butyllithium in hexanes (2.5 M, 18.9 mL, 47.2 mmol) was added dropwise, and stirring was continued for 15 minutes. 2-Trifluoromethoxybenzyl bromide (10.0 g, 39.4 mmol) was added, and the resulting mixture was maintained at −78° C. for 30 minutes, then allowed to slowly warm to room temperature. The reaction was then diluted with saturated aqueous $NH_4Cl$ solution and extracted with ethyl acetate. The organic extracts were combined, dried over $MgSO_4$, filtered and concentrated in vacuo to give an oil that was purified via flash chromatography on silica gel (100% hexanes) to give the desired product.

$^1$H NMR ($CDCl_3$): δ 7.24 (m, 4H), 4.33 (m, 1H), 3.73 (s, 3H), 3.65 (s, 3H), 3.48 (dd, J=3.4, 3.4 Hz, 1H), 3.30 (dd, J=13.5, 4.6 Hz, 1H), 3.05 (dd, J=13.7, 6.7 Hz, 1H), 2.20 (m, 1H), 1.00 (d, J=6.8 Hz, 3H), 0.65 (d, J=6.8 Hz, 3H)

Step 2: Preparation of (R)-2-tert-butoxycarbonylamino-3-(2-trifluoromethoxy-phenyl)-propionic acid Methyl Ester

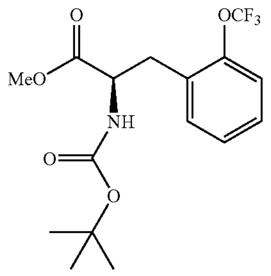

A mixture of the product from Step 1 (6.72 g, 18.8 mmol) in dichloromethane (1 mL), acetonitrile (10 mL) and trifluoroacetic acid (10 mL) was stirred at room temperature for one hour. The mixture was then concentrated in vacuo to give a solid which was used without further purification in the next reaction described below.

To a solution of the crude product described above in tetrahydrofuran (10 mL) were added $K_2CO_3$ (3.90 g, 28.2 mmol) and di-t-butyl dicarbonate (4.50 g, 20.6 mmol). The resulting mixture was stirred at room temperature for 2 hours. The mixture was then diluted with $H_2O$ and extracted twice with ethyl acetate. The organic extracts were combined, dried over $MgSO_4$, filtered and concentrated in vacuo to give a crude product that was purified via flash chromatography on silica gel (0% to 20% ethyl acetate/hexanes linear gradient) to give the desired product.

$^1$H NMR ($CDCl_3$): δ 7.26 (m, 4H), 5.04 (m, 1H), 4.61 (dd, J=14.0, 6.9 Hz, 1H), 3.79 (s, 3H), 3.23 (dd, J=14.0, 5.7 Hz, 1H), 3.11 (dd, J=14.0, 7.0 Hz, 1H), 1.41 (s, 9H)

Step 3: Preparation of (R)-2-tert-butoxycarbonylamino-3-(2-trifluoromethoxy-phenyl)-propionic acid

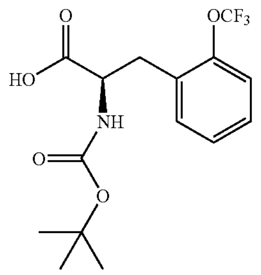

A mixture of the product from Step 2 (5.65 g, 15.6 mmol) in tetrahydrofuran (60 mL), methanol (20 mL) and aqueous 1 N lithium hydroxide solution (20 mL) was stirred at room temperature for 18 hours. The mixture was then poured into 0.5 N aqueous HCl solution and extracted with ethyl acetate. The organic extracts were combined, dried over $MgSO_4$, filtered and concentrated in vacuo to give the desired product.

$^1$H NMR ($CDCl_3$): δ 7.26 (m, 4H), 5.03 (m, 1H), 4.22 (m, 1H), 3.29 (m, 1H), 3.08 (m, 1H), 1.38 (s, 9H)

Step 4: Preparation of (R)-3-(trityl-amino)-1,3,4,5-tetrahydro-1-benzazepin-2-one

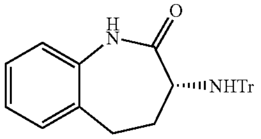

A round-bottom flask was fitted with a condenser, stirbar and septa. 3(R)-Amino-2,3,4,5-tetrahydro-1H-[1]-benzazepin-2-one D-pyroglutamic acid salt (10.0 g, 32.8 mmol), N,N-dimethylformamide (200 mL) and triethylamine (12 mL, 86.1 mmol) were added, giving a mixture which was heated to 120° C. To the resulting solution was added trityl chloride (9.04 g, 32.4 mmol). The reaction was then cooled to 60° C., maintained at 60° C. for 4 hours, and then allowed to slowly cool to room temperature. After 18 hours, the reaction mixture was diluted with diethyl ether (300 mL) and washed first with 400 mL 1:1 $H_2O$:saturated aqueous NaCl solution, then with 2×100 mL $H_2O$. The aqueous washes were combined and extracted with diethyl ether (100 mL). The organic extracts were combined, dried over $MgSO_4$, filtered and concentrated in vacuo to give an oil which that purified via flash chromatography on silica gel (25% ethyl acetate/hexanes) to give the desired product.

$^1$H NMR ($CDCl_3$): δ 7.44 (m, 6H), 7.14 (m, 12H), 6.78 (s, 1H), 6.64 (d, J=7.1 Hz, 1H), 3.32 (d, J=8 Hz, 1H), 3.23 (m, 1H), 2.73 (m, 1H), 2.54 (m, 2H), 2.20 (m, 1H)

MS: m/e 441.4 $(M+23)^+$

Step 5: Preparation of (R)-1-isopropyl-3-(trityl-amino)-1,3,4,5-tetrahydro-1-benzazepin-2-one

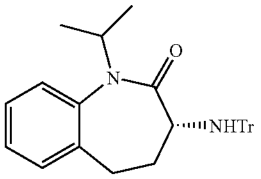

A 35 mL heavy-walled sealable tube was fitted with a stirbar and septa. The tritylated benzolactam from Step 4 (2.02 g, 4.83 mmol) and N,N-dimethylformamide (20 mL) were added, giving a solution that was cooled to 0° C. Sodium hydride (1.08 g, 60%/oil, 27.0 mmol) was added cautiously, giving a mixture that was stirred 5 minutes at 0° C., then removed from the cold bath and allowed to warm to room temperature. After 30 minutes, 2-iodopropane (1.0 mL, 10.0 mmol) was added, and the resulting mixture was stirred at room temperature for 18 hours. The rubber septa was then removed, the reaction vessel was sealed with a plastic screw-cap, placed in an oil bath and warmed to 60° C. After 4 hours, the reaction was cooled to room temperature, diluted with $H_2O$ (100 mL) and extracted three times with diethyl ether (100 mL, then 2×50 mL). The organic extracts were combined, washed with saturated aqueous NaCl solution (50 mL), dried over $MgSO_4$, filtered and concentrated in vacuo. The resulting oil was purified via flash chromatography on silica gel (0% to 25% ethyl acetate/hexanes linear gradient) to give the desired product.

$^1$H NMR ($CDCl_3$): δ 7.38 (m, 6H), 7.13 (m, 12H), 6.77 (d, J=7.4 Hz, 1H), 4.42 (dddd, J=6.9, 6.9, 6.9, 6.9 Hz, 1H), 3.46 (br s, 1H), 2.97 (m, 1H), 2.62 (ddd, J=13.2, 13.2, 8.2 Hz, 1H), 2.41 (m, 2H), 2.13 (ddd, J=11.9, 11.9, 7.5 Hz, 1H), 1.04 (d, J=6.8 Hz, 3H), 0.77 (d, J=7.1 Hz, 3H)

MS: m/e 483.5 $(M+23)^+$

Step 6: Preparation of [(R)-1-((R)-1-isopropyl-2-oxo-2,3,4,5-tetrahydro-1H-1-benzazepin-3-ylcarbamoyl)-2-(2-trifluoromethoxy-phenyl)-ethyl]-carbamic acid tert-butyl Ester

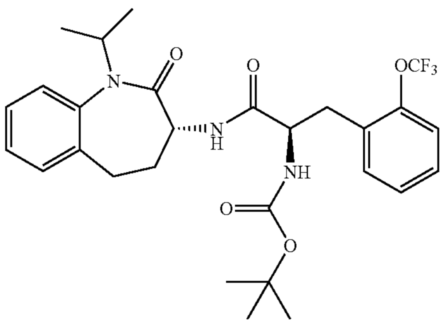

A round-bottom flask containing a stirbar was charged with the product from Step 5 (1.58 g, 3.43 mmol) and a solution of concentrated HCl (1 mL) in methanol (19 mL). The resulting solution was stirred for 4.5 hours at room temperature, then concentrated in vacuo to give a solid that was used without further purification in the next reaction described below.

A mixture of the crude product described above (1.01 g), N-(3-dimethylaminopropyl)-N'-ethylcarbodiimide hydrochloride (0.843 g, 4.39 mmol), 1-hydroxybenzotriazole (0.593 g, 4.39 mmol), diisopropylethylamine (1.90 mL, 11.0 mmol), the product from Step 3 (0.843 g, 2.42 mmol) and tetrahydrofuran (15 mL) was stirred for 18 hours at room temperature. The reaction was then diluted with $H_2O$ and extracted with ethyl acetate. The organic extracts were concentrated in vacuo and purified via flash chromatography on silica gel (0% to 50% ethyl acetate/hexanes linear gradient) to give the desired product.

$^1$H NMR ($CDCl_3$): δ 7.27 (m, 7H), 7.05 (br s, 1H), 5.04 (m, 1H), 4.72 (dddd, J=6.9, 6.9, 6.9, 6.9 Hz, 1H), 4.38 (m, 1H), 4.24 (m, 1H), 3.15 (dd, J=14.2, 5.7 Hz, 1H), 3.00 (m, 1H), 2.82 (m, 1H), 2.57 (m, 2H), 1.78 (m, 1H), 1.45 (d, J=6.9 Hz, 3H), 1.37 (s, 9H), 1.10 (d, J=7.1 Hz, 3H)

MS: m/e 550.0 $(M+1)^+$

Step 7: Preparation of pyrazine-2-carboxylic acid [(R)-1-((R)-1-isopropyl-2-oxo-2,3,4,5-tetrahydro-1H-1-benzazepin-3-ylcarbamoyl)-2-(2-trifluoromethoxy-phenyl)-ethyl]-amide

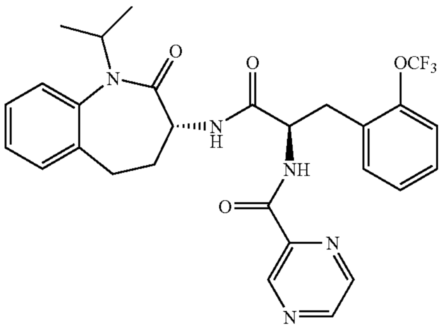

A solution of the product from Step 6 (0.69 g, 1.3 mmol) in dichloromethane (35 mL) and trifluoroacetic acid (15 mL) was stirred for 18 hours at room temperature. The reaction was then concentrated in vacuo, neutralized with saturated aqueous $NaHCO_3$ solution and extracted with ethyl acetate. The organic extracts were combined and concentrated in vacuo to give a crude product that was used without further purification in the next reaction described below.

A mixture of the crude product described above (0.050 g, 0.11 mmol), N-(3-dimethylaminopropyl)-N'-ethylcarbodiimide hydrochloride (0.042 g, 0.22 mmol), 1-hydroxybenzotriazole (0.030 g, 0.22 mmol), diisopropylethylamine (0.10 mL, 0.56 mmol) 2-pyrazinecarboxylic acid (0.017 g, 0.13 mmol) and tetrahydrofuran (2.0 mL) was stirred at room temperature for 18 hours. The reaction was then diluted with $H_2O$ and extracted with ethyl acetate. The organic extracts were concentrated in vacuo and purified via preparative thin layer chromatography on silica (50% ethyl acetate/hexanes) to give the desired product.

$^1$H NMR ($CDCl_3$): δ 9.33 (s, 1H), 8.73 (s, 1H), 8.51 (s, 1H), 8.32 (d, J=8.2 Hz, 1H), 7.21 (m, 6H), 6.96 (d, J=6.4 Hz, 1H), 4.85 (dd, J=8, 7 Hz, 1H), 4.72 (dddd, J=7 Hz, 1H), 4.22 (m, 1H), 3.23 (m, 2H), 2.79 (m, 1H), 2.55 (m, 2H), 1.77 (m, 1H), 1.41 (d, J=6.9 Hz, 3H), 1.07 (d, J=7.0 Hz, 3H)

MS: m/e 556.0 $(M+1)^+$

Example 2

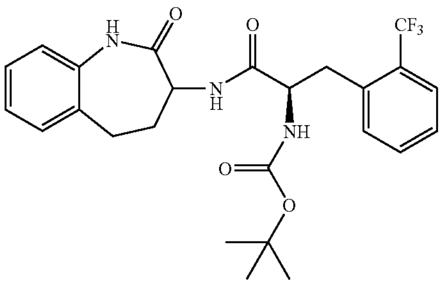

[(R)=1-(2-Oxo-2,3,4,5-tetrahydro-1H-benzo[b]azepin-3-ylcarbamoyl)-2-(2-trifluoromethyl-phenyl)-ethyl]-carbamic acid tert-butyl Ester Step 1: Preparation of [(R)-1-(2-Oxo-2,3,4,5-tetrahydro-1H-benzo[b]azepin-3-ylcarbamoyl)-2-(2-trifluoromethyl-phenyl)-ethyl]-carbamic acid tert-butyl Ester

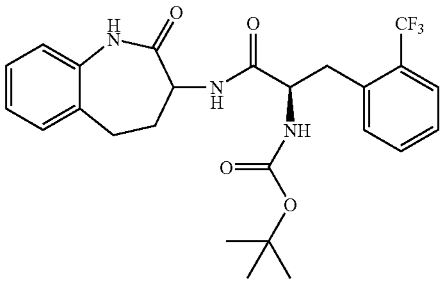

To a solution of racemic 3-amino-2,3,4,5-tetrahydro-1H-[1]-benzazepin-2-one (0.100 g, 0.57 mmol) in dichloromethane (5.0 mL) were added N-(3-dimethylaminopropyl)-N'-ethylcarbodiimide hydrochloride (0.218 g, 1.13 mmol), 1-hydroxybenzotriazole (0.153 g, 1.13 mmol), diisopropylethylamine (0.20 mL, 1.13 mmol) and N-Boc-D-2-trifluoromethyl phenylalanine (0.189 g, 0.57 mmol). The resulting mixture was stirred at room temperature for 18 hours, then diluted with $H_2O$ and extracted with ethyl acetate. The organic extracts were combined, dried over $MgSO_4$, filtered and concentrated in vacuo to give an oil that was purified via prepatory thin-layer chromatography on silica gel (50% ethyl acetate/hexanes) to give the desired product.

$^1$H NMR ($CDCl_3$): δ 7.63 (m, 1H), 7.32 (m, 6H), 6.97 (m, 1H), 5.04 (m, 1H), 4.61 (m, 1H), 4.44 (m, 2H), 3.28 (dd, J=4.6, 4.6 Hz, 1H), 2.85 (m, 4H), 1.96 (m, 1H), 1.76 (m, 1H), 1.34 (s, 9H)

MS: m/e 392.0 $(M+1\text{-}Boc)^+$

Examples listed below in TABLE 1 were prepared according to the procedures given above for the preparation of EXAMPLES 1 and 2 using the appropriate commercially available starting materials. The carbon atoms marked with an * have the stereochemical configurations as depicted in the table below.

TABLE 1

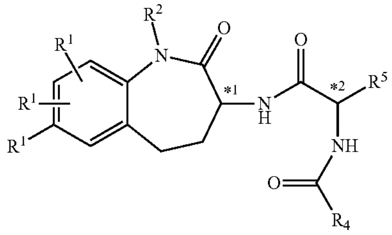

| Example # | $R^1$ | $R^2$ | *1, *2 | $R^4$ | $R^5$ | (m/e) (M + H) |
|---|---|---|---|---|---|---|
| 3 | H | $CH_3$ | R, R | OtBu | 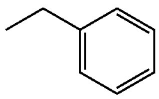 | 438.2 |
| 4 | H | $CH_3$ | RS, R | OtBu | 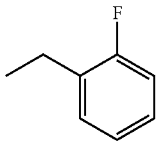 | 456.3 |
| 5 | H | $CH_3$ | R, R | OtBu | 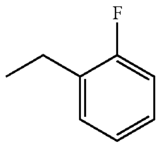 | 456.2 |
| 6 | H | cyclopropyl-methyl | R, R | OtBu | 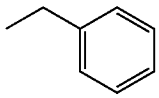 | 478.2 |
| 7 | H | cyclopropyl-methyl | R, R | OtBu | 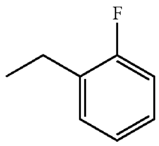 | 496.2 |

TABLE 1-continued
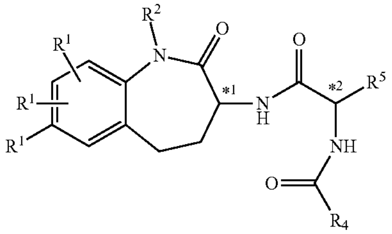
| Example # | $R^1$ | $R^2$ | *1, *2 | $R^4$ | $R^5$ | (m/e) (M + H) |
|---|---|---|---|---|---|---|
| 8 | H | $CF_3CH_2$— | R, R | OtBu | 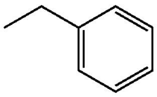 | 506.1 |
| 9 | H | $CF_3CH_2$— | R, R | OtBu | 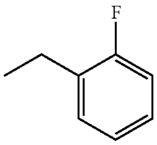 | 524.0 |
| 10 | H | $CF_3CH_2$— | R, R | OtBu | 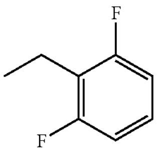 | 564.2 M + Na |
| 11 | H | n-propyl | R, R | OtBu | 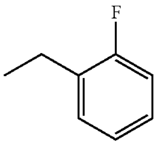 | 384.5 M − Boc + H |
| 12 | H | i-propyl | R, R | OtBu | 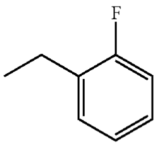 | 506.5 M + Na |
| 13 | H | allyl | R, R | OtBu | 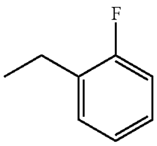 | 504.4 M + Na |
| 14 | H | —$CH_2CONH_2$ | R, R | OtBu | 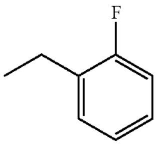 | 499.4 |
| 15 | H | i-propyl | R, R | OtBu | 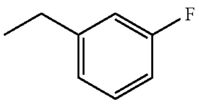 | 506.5 M + Na |
| 16 | H | i-propyl | R, R | OtBu | 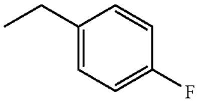 | 506.5 M + Na |

TABLE 1-continued
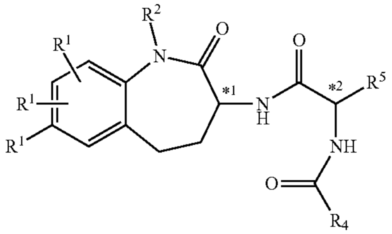
| Example # | $R^1$ | $R^2$ | *1, *2 | $R^4$ | $R^5$ | (m/e) (M + H) |
|---|---|---|---|---|---|---|
| 17 | H | i-propyl | R, R | OtBu | 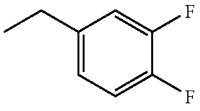 | 524.5 M + Na |
| 18 | H | i-propyl | R, R | OtBu | 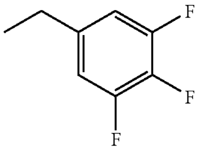 | 542.5 M + Na |
| 19 | H | i-propyl | R, R | OtBu | 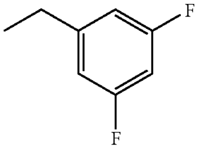 | 502.1 |
| 20 | H | i-propyl | R, R | OtBu | 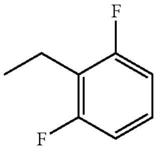 | 524.5 M + Na |
| 21 | H | i-propyl | R, R | OtBu | 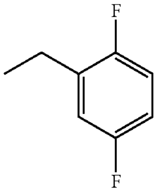 | 524.5 M + Na |
| 22 | H | i-propyl | R, R | OtBu | 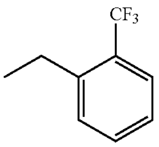 | 556.5 M + Na |
| 23 | H | i-propyl | R, R | OtBu | 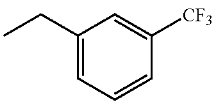 | 556.5 M + Na |
| 24 | H | i-propyl | R, R | OtBu | 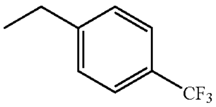 | 556.0 M + Na |

TABLE 1-continued
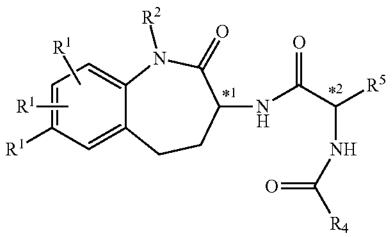
| Example # | $R^1$ | $R^2$ | *1, *2 | $R^4$ | $R^5$ | (m/e) (M + H) |
|---|---|---|---|---|---|---|
| 25 | H | i-propyl | R, R | OtBu | 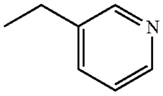 | 467.0 |
| 26 | H | i-propyl | R, R | OtBu | 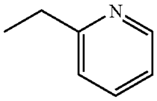 | 467.5 |
| 27 | H | i-propyl | R, R | OtBu | 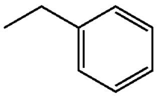 | 488.5 M + Na |
| 28 | H | i-propyl | R, R | OtBu | 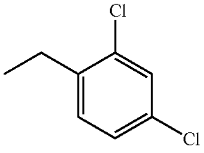 | 534.4 |
| 29 | H | i-propyl | R, R | OtBu | 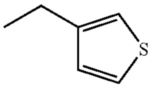 | 494.4 M + Na |
| 30 | H | i-propyl | R, R | OtBu | 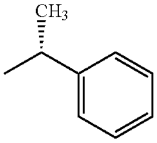 | 480.4 |
| 31 | H | i-propyl | R, R | OtBu | 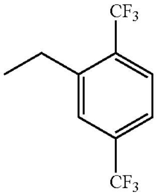 | 624.5 M + Na |
| 32 | H | i-propyl | R, R | OtBu | 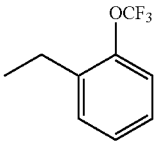 | 550.3 |
| 33 | H | i-propyl | R, R | OtBu | 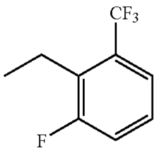 | 452.4 M − Boc + H |

TABLE 1-continued
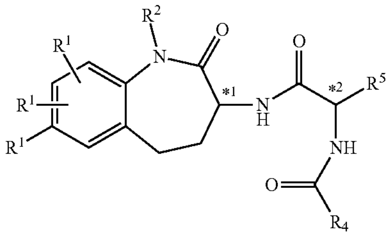
| Example # | $R^1$ | $R^2$ | *1, *2 | $R^4$ | $R^5$ | (m/e) (M + H) |
|---|---|---|---|---|---|---|
| 34 | H | i-propyl | R, R | OtBu | 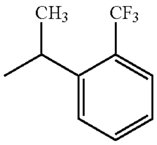 | 448.5 M − Boc + H |
| 35 | H | i-propyl | R, R | OtBu | 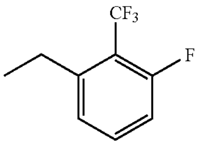 | 452.3 M − Boc + H |
| 36 | H | i-propyl | R, R | OtBu | 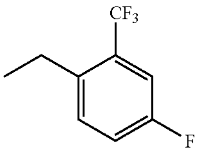 | 452.3 M − Boc + H |
| 37 | H | i-propyl | R, R | OtBu | 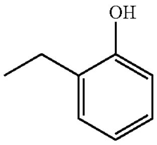 | 482.2 |
| 38 | H | i-propyl | R, R | OtBu | 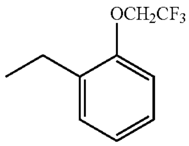 | 464.4 M − Boc + H |
| 39 | H | i-propyl | R, R | -t-butyl | 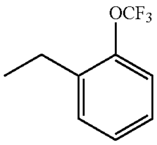 | 534.2 |
| 40 | H | $CF_3CH_2$— | R, R | -t-butyl | 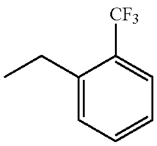 | 574.3 |
| 41 | H | H | R, R | OtBu | 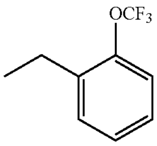 | 494.3 |

TABLE 1-continued
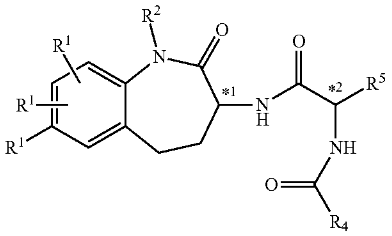
| Example # | $R^1$ | $R^2$ | *1, *2 | $R^4$ | $R^5$ | (m/e) (M + H) |
|---|---|---|---|---|---|---|
| 42 | H | H | S, R | OtBu | 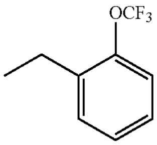 | 508.2 |
| 43 | H | i-propyl | S, R | OtBu | 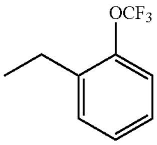 | 550.4 |
| 44 | H | i-propyl | R, R | 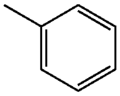 | 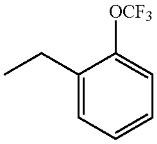 | 554.4 |
| 45 | H | i-propyl | R, R | 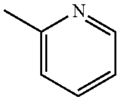 | 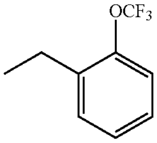 | 555.4 |
| 46 | H | i-propyl | R, R | 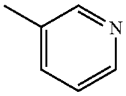 | 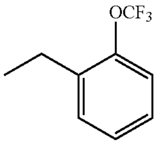 | 555.2 |
| 47 | H | i-propyl | R, R | 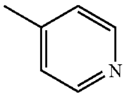 | 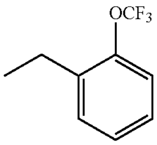 | 555.2 |
| 48 | H | i-propyl | R, R | 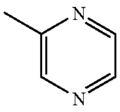 | 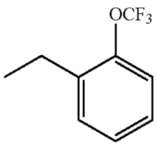 | 556.4 |
| 49 | H | i-propyl | R, R | 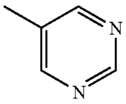 | 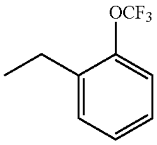 | 556.2 |

TABLE 1-continued
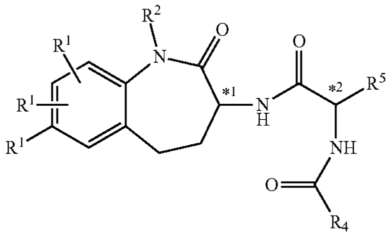
| Example # | $R^1$ | $R^2$ | *1, *2 | $R^4$ | $R^5$ | (m/e) (M + H) |
|---|---|---|---|---|---|---|
| 50 | H | i-propyl | R, R | 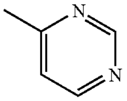 | 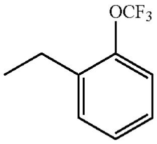 | 556.2 |
| 51 | H | i-propyl | R, R | 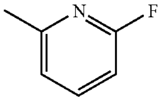 | 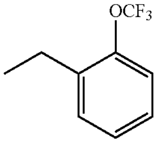 | 573.4 |
| 52 | H | i-propyl | R, R | 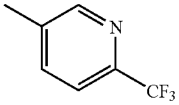 | 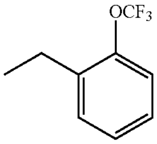 | 623.4 |
| 53 | H | i-propyl | R, R | 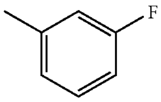 | 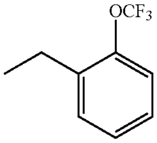 | 572.3 |
| 54 | H | i-propyl | R, R | 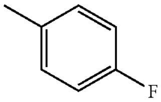 | 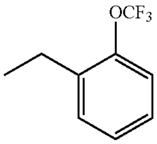 | 572.4 |
| 55 | H | i-propyl | R, R | 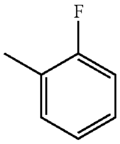 | 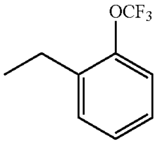 | 572.3 |
| 56 | H | i-propyl | R, R | 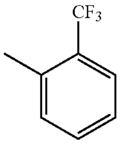 | 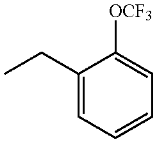 | 622.3 |
| 57 | H | i-propyl | R, R | 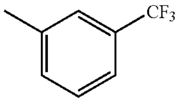 | 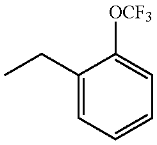 | 622.3 |

TABLE 1-continued
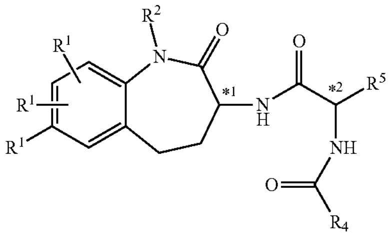
| Example # | $R^1$ | $R^2$ | *1, *2 | $R^4$ | $R^5$ | (m/e) (M + H) |
|---|---|---|---|---|---|---|
| 58 | H | i-propyl | R, R | 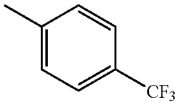 | 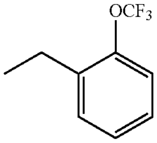 | 622.3 |
| 59 | H | i-propyl | R, R | 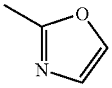 | 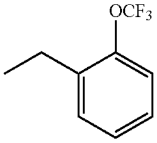 | 545.3 |
| 60 | H | i-propyl | R, R | 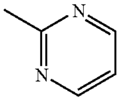 | 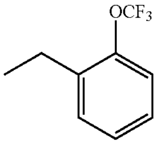 | 556.4 |
| 61 | H | i-propyl | R, R | 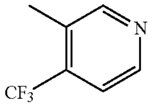 | 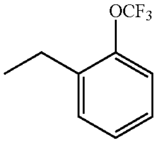 | 623.5 |
| 62 | H | i-propyl | R, R | 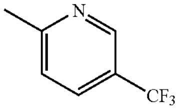 | 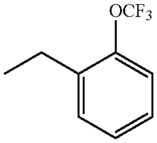 | 623.5 |
| 63 | H | i-propyl | R, R | 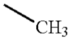 | 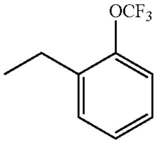 | 492.5 |
| 64 | H | i-propyl | R, R | 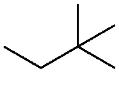 | 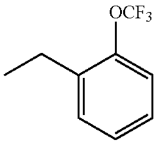 | 548.5 |
| 65 | H | i-propyl | R, R | 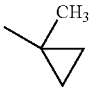 | 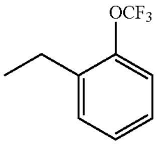 | 532.5 |

TABLE 1-continued
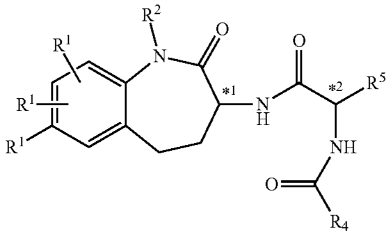
| Example # | $R^1$ | $R^2$ | *1, *2 | $R^4$ | $R^5$ | (m/e) (M + H) |
|---|---|---|---|---|---|---|
| 66 | H | i-propyl | R, R | 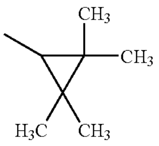 | 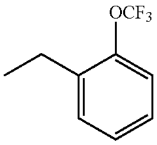 | 574.7 |
| 67 | H | i-propyl | R, R | 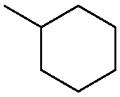 | 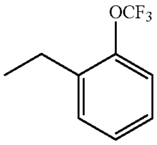 | 560.6 |
| 68 | H | i-propyl | R, R | 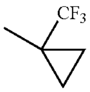 | 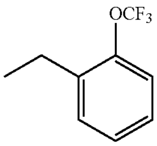 | 586.3 |
| 69 | H | i-propyl | R, R | 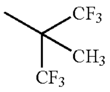 | 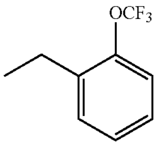 | 642.3 |
| 70 | H | i-propyl | R, R | 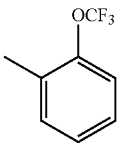 | 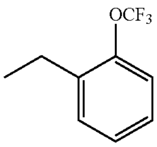 | 638.6 |
| 71 | H | i-propyl | R, R | 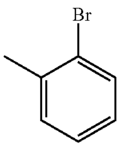 | 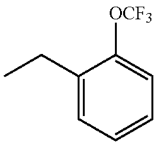 | 634.5 |
| 72 | H | i-propyl | R, R | 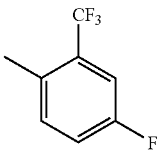 | 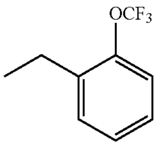 | 640.6 |

Examples 73 and 74

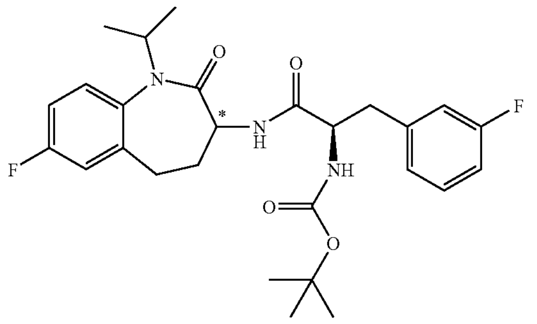

Diastereomeric Mixture

Diastereomer 1: [(R)-1-((R)-7-Fluoro-1-isopropyl-2-oxo-2,3,4,5-tetrahydro-1H-1-benzazepin-3-ylcarbamoyl)-2-(3-fluoro-phenyl)-ethyl]-carbamic acid tert-butyl Ester and Diastereomer 2: [(R)-1-((S)-7-fluoro-1-isopropyl-2-oxo-2,3,4,5-tetrahydro-1H-1-benzazepin-3-ylcarbamoyl)-2-(3-fluoro-phenyl)-ethyl]-carbamic acid tert-butyl Ester Step 1: Preparation of 2-allyl-4-fluoro-phenylamine

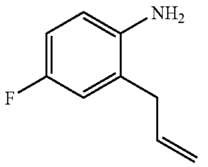

A round-bottom flask was fitted with a condenser, stirbar and septa and flushed with nitrogen. 2-bromo-4-fluoro aniline (9.70 g, 40.9 mmol), N,N-dimethylformamide (100 mL), allyltributyltin (15.0 mL, 48.9 mmol) and $Pd(PPh_3)_4$ (1.50 g, 1.30 mmol) were added, giving a mixture that was warmed to 80° C. After 17 hours, the reaction was cooled to room temperature, diluted with ethyl acetate (300 mL) and washed with 1:1 $H_2O$:saturated aqueous NaCl solution (2×150 mL). The aqueous washes were combined and extracted with ethyl acetate (50 mL). The organic extracts were then combined, dried over $MgSO_4$, filtered and concentrated in vacuo to give an oil that was purified via flash chromatography on silica gel (0% to 35% ethyl acetate/hexanes linear gradient) to give the desired product.

$^1H$ NMR ($CDCl_3$): δ 6.78 (m, 2H), 6.61 (dd, J=8.4, 5.0 Hz, 1H), 5.93 (dddd, J=16.4, 10.0, 6.1, 6.1 Hz, 1H), 5.12 (m, 2H), 3.55 (br s, 2H), 3.27 (d, J=6.0 Hz, 2H)

MS: m/e 152.2 $(M+1)^+$

Step 2: Preparation of N-(2-allyl-4-fluoro-phenyl)-acrylamide

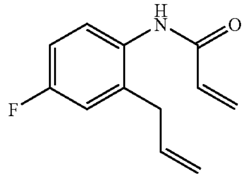

A round-bottom flask containing the product from Step 1 (10.6 g, 70.1 mmol) was fitted with a stirbar and septa. Tetrahydrofuran (200 mL) and triethylamine (15.0 mL, 108 mmol) were added, giving a solution that was cooled to −10° C. Acryloyl chloride (6.0 mL, 73.6 mmol) was then added, and the resulting mixture was allowed to gradually warm to room temperature. After 16 hours, the reaction was concentrated to remove most of the tetrahydrofuran, then diluted with ethyl acetate (200 mL) and washed with 1:1 $H_2O$:saturated aqueous NaCl solution (2×100 mL). The organic extracts were dried over $MgSO_4$, filtered and concentrated in vacuo to give an oil which was purified via flash chromatography on silica gel (15% to 40% ethyl acetate/hexanes linear gradient) to give the desired product.

$^1H$ NMR ($CDCl_3$): δ 7.80 (dd, J=8.3, 5.5 Hz, 1H), 7.34 (br s, 1H), 6.93 (m, 2H), 6.37 (d, J=17.0 Hz, 1H), 6.20 (dd, J=16.9, 10.3 Hz, 1H), 5.94 (m, 1H), 5.75 (d, J=10.3 Hz, 1H), 5.20 (d, J=9.8 Hz, 1H), 5.10 (d, J=17.2 Hz, 1H), 3.35 (d, J=6.2 Hz, 2H)

MS: m/e 206.1 $(M+1)^+$

Step 3: Preparation of 7-fluoro-1,5-dihydro-1-benzazepin-2-one

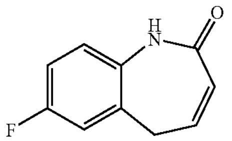

A round-bottom flask containing the product from Step 2 (4.51 g, 21.9 mmol) was fitted with a stirbar and septa. Dichloromethane (800 mL) and Zhan catalyst I (0.735 g, 1.11 mmol) were added, and the resulting solution was stirred for 18 hours at room temperature. The reaction was then concentrated in vacuo and recrystallized from dichloromethane to give the desired product.

$^1H$ NMR ($CDCl_3$): δ 9.58 (s, 1H), 7.11 (dd, J=8.7, 5.0 Hz, 1H), 6.92 (ddd, J=8.5, 8.5, 3.0 Hz, 1H), 6.86 (dd, J=8.5, 2.8 Hz, 1H), 6.61 (ddd, J=11, 6.9, 6.9 Hz, 1H), 5.97 (dd, J=10.9, 1.3 Hz, 1H), 3.34 (d, J=6.9 Hz, 2H)

MS: m/e 178.2 $(M+1)^+$

Step 4: Preparation of 7-fluoro-1-isopropyl-1,3,4,5-tetrahydro-1-benzazepin-2-one

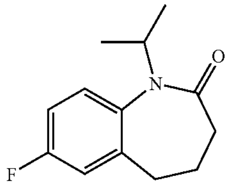

A round-bottom flask containing the product of Step 3 (2.61 g, 14.7 mmol) was fitted with a stirbar and septa. Tetrahydrofuran (30 mL), ethanol (30 mL) and 10% Pd/C (0.488 g) were added. The reaction vessel was flushed with $H_2$, then placed under a balloon of $H_2$ and stirred at room temperature for 18 hours. The reaction mixture was then filtered through celite and concentrated in vacuo to give a solid that was used without further purification in the next step described below.

A round-bottom flask containing the crude hydrogenation product (2.02 g, 11.3 mmol) described above was fitted with a condenser, stirbar and septa. N,N-Dimethylformamide (30 mL) and sodium hydride (0.896 g, 60%/oil, 22.4 mmol) were added, in that order, giving a mixture which was stirred for 30 minutes at room temperature. 2-Iodopropane (2.2 mL, 22.0 mmol) was then added, and the reaction was warmed to 60° C. After 18 hours, the reaction was poured into 100 mL 1:1 $H_2O$:saturated aqueous NaCl solution and extracted with ethyl acetate (3×50 mL). The organic extracts were combined, dried over $MgSO_4$, filtered and concentrated in vacuo to give an oil that was purified via flash chromatography on silica gel (10% to 60% ethyl acetate/hexanes linear gradient) to give the desired product.

$^1$H NMR ($CDCl_3$): δ 7.15 (dd, J=8.7, 5.1 Hz, 1H), 6.91 (m, 2H), 4.80 (dddd, J=13.7, 13.7, 6.8, 6.8 Hz, 1H), 2.76 (ddd, J=13.0, 13.0, 7.6 Hz, 1H), 2.55 (dd, J=13.5, 6.8 Hz, 1H), 2.23 (m, 3H), 1.88 (dddd, J=14.2, 14.2, 7.8, 7.8 Hz, 1H), 1.41 (d, J=6.7 Hz, 3H), 1.03 (d, J=6.8 Hz, 3H)

MS: m/e 222.2 $(M+1)^+$

Step 5: Preparation of 7-fluoro-3-iodo-1-isopropyl-1,3,4,5-tetrahydro-1-benzazepin-2-one

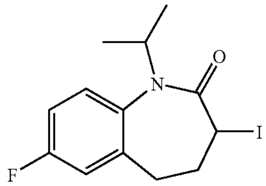

An oven-dried round-bottom flask containing the product of Step 4 (1.92 g, 8.68 mmol) was fitted with a stirbar and septa and flushed with nitrogen. Dichloromethane (50 mL) and N,N',N'-tetramethylethylenediamine (5.80 mL, 38.4 mmol) were added, giving a solution that was cooled to −10° C. Iodotrimethylsilane (4.80 mL, 35.3 mmol) was added, and stirring was continued at −10° C. for 30 minutes. Iodine (4.71 g, 18.6 mmol) was then added, and the reaction was warmed to 0° C. After stirring 2 hours at 0° C., the reaction was diluted with dichloromethane (100 mL) and washed with 10% aqueous sodium sulfite solution (2×50 mL). The organic layer was then dried over $MgSO_4$, filtered and concentrated in vacuo to give an oil that was purified via flash chromatography on silica gel (0% to 30% ethyl acetate/hexanes linear gradient) to give the desired product.

$^1$H NMR ($CDCl_3$): 7.18 (dd, J=8.7, 5.1 Hz, 1H), 7.00 (ddd, J=8.3, 8.3, 3.0 Hz, 1H), 6.92 (dd, J=8.4, 2.7 Hz, 1H), 4.74 (dddd, J=14.0, 14.0, 7.1, 7.1 Hz, 1H), 4.45 (m, 1H), 2.88 (m, 1H), 2.75 (m, 1H), 2.49 (m, 2H), 1.41 (d, J=6.7 Hz, 3H), 1.07 (d, J=6.9 Hz, 3H)

MS: m/e 348.0 $(M+1)^+$

Step 6: Preparation of 3-azido-7-fluoro-1-isopropyl-1,3,4,5-tetrahydro-1-benzazepin-2-one

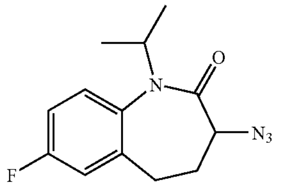

A round-bottom flask containing the product of Step 5 (2.11 g, 6.08 mmol) was fitted with a stirbar and septa. N,N-Dimethylformamide (25 mL) was added, giving a solution to which sodium azide (0.652 g, 10.0 mmol) was added. The resulting mixture was warmed to 40° C. and stirred for 3 days. The reaction was then cooled to room temperature, diluted with 100 mL 1:1 $H_2O$:saturated aqueous NaCl solution and extracted with ethyl acetate (3×50 mL). The organic extracts were combined, dried over $MgSO_4$, filtered and concentrated in vacuo to give an oil that was purified via flash chromatography on silica gel (0% to 30% ethyl acetate/hexanes linear gradient) to give the desired product.

$^1$H NMR ($CDCl_3$): 7.17 (dd, J=8.7, 5.1 Hz, 1H), 6.99 (ddd, J=8.2, 8.2, 2.9 Hz, 1H), 6.94 (dd, J=8.4, 2.9 Hz, 1H), 4.79 (m, 1H), 3.51 (dd, J=11.2, 8.3 Hz, 1H), 2.85 (ddd, J=13.3, 13.3, 8.7 Hz, 1H), 2.62 (ddd, J=13.7, 6.2, 1.8 Hz, 1H), 2.29 (m, 2H), 1.45 (d, J=6.9 Hz, 3H), 1.09 (d, J=7.1 Hz, 3H)

MS: m/e 285.1 $(M+23)^+$

Step 7: Preparation of [(R)-1-((R)-7-fluoro-1-isopropyl-2-oxo-2,3,4,5-tetrahydro-1H-1-benzazepin-3-ylcarbamoyl)-2-(3-fluoro-phenyl)-ethyl]-carbamic acid tert-butyl ester (diastereomer 1); and [(R)-1-((S)-7-fluoro-1-isopropyl-2-oxo-2,3,4,5-tetrahydro-1H-1-benzazepin-3-ylcarbamoyl)-2-(3-fluoro-phenyl)-ethyl]-carbamic acid tert-butyl ester (diastereomer 2)

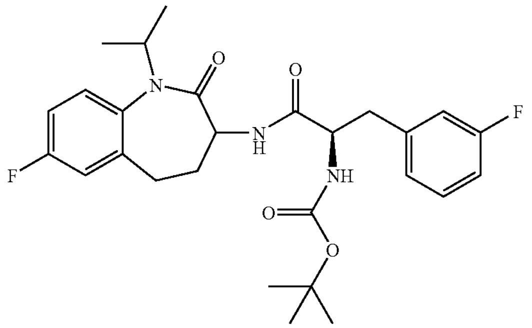

A round-bottom flask containing the product of Step 6 (1.22 g, 4.65 mmol) was fitted with a stirbar and septa and charged with ethanol (20 mL) and 10% Pd/C (0.316 g). The reaction vessel was flushed with $H_2$, then placed under a balloon of $H_2$ and stirred at room temperature for 3 days. The reaction mixture was then filtered through celite and concentrated in vacuo to give an oil that was used without further purification in the next step described below.

A round-bottom flask containing the crude hydrogenation product (0.23 g, 0.98 mmol) described above was fitted with a stirbar and septa. Dichloromethane (3 mL), diisopropylethylamine (0.54 mL, 3.1 mmol), N-Boc-D-3-fluorophenylalanine (0.400 g, 1.42 mmol) and benzotriazol-1-yloxytris(dimethylamino)phosphonium hexafluorophosphate (0.820 g, 1.85 mmol) were added, in that order, giving a solution that was stirred for 23 hours at room temperature. The reaction was then purified via flash chromatography on silica gel (15% to 60% ethyl acetate/hexanes linear gradient) to give the desired product as a mixture of 2 diastereomers. This mixture was further purified via HPLC (Chiralcel OD column, 15% 2-propanol/heptane) to give a faster-eluting diastereomer (d1) and a slower-eluting diastereomer (d2).

d1 $^1H$ NMR ($CDCl_3$): 7.24 (m, 2H), 7.17 (dd, J=8.7, 5.0 Hz, 1H), 6.92 (m, 5H), 4.94 (m, 1H), 4.71 (dddd, J=6.9, 6.9, 6.9, 6.9 Hz, 1H), 4.33 (m, 1H), 4.19 (m, 1H), 3.05 (m, 1H), 2.97 (dd, J=13.8, 6.5 Hz, 1H), 2.78 (m, 1H), 2.56 (m, 2H), 1.74 (ddd, J=11.7, 11.7, 8.7 Hz, 1H), 1.42 (m, 12H), 1.07 (d, J=6.9 Hz, 3H)

d1 MS: m/e 524.2 $(M+23)^+$ d2 $^1H$ NMR ($CDCl_3$): 7.25 (m, 1H), 7.15 (dd, J=8.7, 5.1 Hz, 1H), 6.95 (m, 4H), 6.86 (d, J=9.6 Hz, 1H), 6.79 (br s, 1H), 4.99 (m, 1H), 4.73 (dddd; J=6.9, 6.9, 6.9, 6.9 Hz, 1H), 4.33 (m, 1H), 4.25 (ddd, J=10.8, 7.6, 7.6 Hz, 1H), 3.00 (m, 2H), 2.75 (ddd, J=12.8, 12.8, 8.4 Hz, 1H), 2.48 (m, 2H), 1.61 (ddd, J=11.6, 11.6, 8.0 Hz, 1H), 1.41 (m, 12H), 1.05 (d, J=7.1 Hz, 3H)

d2 MS: m/e 524.2 $(M+23)^+$

Intermediate 19 from Scheme 4

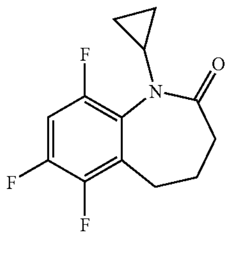

1-Cyclopropyl-6,7,9-trifluoro-1,3,4,5-tetrahydro-benzo[b]azepin-2-one

Step 1: Preparation of 6,7,9-trifluoro-1-vinyl-1,3,4,5-tetrahydro-benzo[b]azepin-2-one

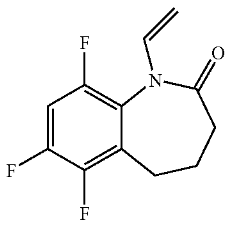

A heavy-walled sealable 100 mL tube containing copper (I) iodide (0.088 g, 0.46 mmol), potassium carbonate (1.57 g, 11.4 mmol) and 6,7,9-trifluoro-1,5-dihydro-benzo[b]azepin-2-one (1.02 g, 4.74 mmol, prepared from commercially available 2-bromo-3,4,6-trifluoroaniline via application of Steps 1-3 of the procedure used for the synthesis of Examples 73 and 74) was fitted with a stirbar and septa and flushed with nitrogen. Toluene (5.0 mL), N,N'-dimethylethylene diamine (0.10 mL, 0.93 mmol) and vinyl bromide (10.0 mL, 1.0 M solution in tetrahydrofuran (THF), 10.0 mmol) were then added, in that order. The septa was removed, the reaction vessel was sealed tightly with a teflon screwcap and then placed in a pre-heated 110° C. oil bath. After 24 hours, the reaction was cooled to room temperature, poured into 1:1 $H_2O$:saturated aqueous NaCl solution (50 mL) and extracted with methylene chloride (3×30 mL). The organic extracts were combined, dried over $MgSO_4$, filtered and concentrated in vacuo to give an oil that was purified via flash chromatography on silica gel (0% to 30% ethyl acetate/hexanes linear gradient) to give the desired product.

$^1H$ NMR ($CDCl_3$): 7.45 (dd, J=16.0, 8.9 Hz, 1H), 6.95 (ddd, J=9.9, 9.9, 7.1 Hz, 1H), 4.55 (dd, J=9.1, 1.3 Hz, 1H), 4.20 (ddd, J=16.0, 3.2, 1.4 Hz, 1H), 3.19 (dd, J=13.7, 6.6 Hz, 1H), 2.33 (m, 4H), 1.96 (m, 1H)

MS: m/e 242.11 $(M+H)^+$

Step 2: Preparation of 1-cyclopropyl-6,7,9-trifluoro-1,3,4,5-tetrahydro-benzo[b]azepin-2-one

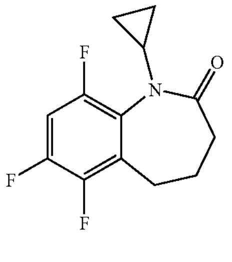

An oven-dried 250 mL round-bottom flask was fitted with a stirbar and septa and flushed with nitrogen. Diethyl zinc (12.0 mL, 1.0 M/hexanes, 12.0 mmol) was added and cooled to 0° C. Trifluoroacetic acid (0.90 mL, 11.7 mmol) was added in a careful, dropwise manner over 5 minutes, and the reaction was then stirred for 15 minutes. Methylene chloride (10 mL) and diiodomethane (1.20 mL, 14.9 mmol) were then added, and the reaction was stirred for an additional 20 minutes. A solution of the product of Step 1 (1.01 g, 4.19 mmol) in methylene chloride (20 mL) was then added, and the reaction was stirred overnight with gradual warming to room temperature. After 25 hours, the reaction was poured into saturated aqueous $NH_4Cl$ solution (50 mL) and extracted with methylene chloride (3×50 mL). The organic extracts were combined, dried over $MgSO_4$, filtered and concentrated in vacuo to give an oil that was purified via flash chromatography on silica gel (0% to 20% ethyl acetate/hexanes linear gradient) to give the desired product.

$^1$H NMR ($CDCl_3$): 6.92 (ddd, J=10.1, 10.1, 7.1 Hz, 1H), 3.11 (m, 2H), 2.26 (m, 4H), 1.92 (m, 1H), 1.09 (m, 1H), 0.67 (m, 2H), 0.90 (m, 1H)

MS: m/e 256.29 $(M+H)^+$

Intermediate 21 from Scheme 5

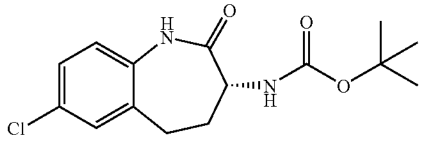

((R)-7-Chloro-2-oxo-2,3,4,5-tetrahydro-1H-1-benzazepin-3-yl)-carbamic acid tert-butyl Ester Step 1: Preparation of ((R)-7-chloro-2-oxo-2,3,4,5-tetrahydro-1H-1-benzazepin-3-yl)-carbamic acid tert-butyl Ester

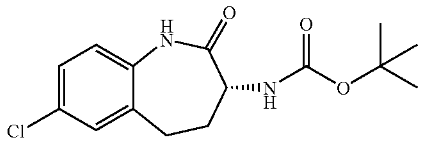

A round-bottom flask containing ((R)-2-oxo-2,3,4,5-tetrahydro-1H-benzo[b]azepin-3-yl)-carbamic acid tert-butyl ester (3.09 g, 11.2 mmol) was fitted with a stirbar and septa and flushed with nitrogen. N,N-Dimethylformamide (30 mL) was added, giving a solution that was cooled to 0° C. N-Chlorosuccinimide (2.20 g, 16.5 mmol) was then added, and stirring was continued for 24 hours. The reaction was then poured into ethyl acetate (200 mL) and washed with 1:1 $H_2O$:saturated aqueous NaCl solution (2×100 mL). The organic layer was dried over $MgSO_4$, filtered and concentrated in vacuo to give a solid that was purified via flash chromatography on silica gel (5% to 30% ethyl acetate/hexanes linear gradient) to give the desired product.

$^1$H NMR ($CDCl_3$): 8.23 (s, 1H), 7.20 (m, 2H), 6.93 (d, J=8.2 Hz, 1H), 5.46 (d, J=7.5 Hz, 1H), 4.26 (m, 1H), 2.90 (m, 1H), 2.64 (m, 2H), 2.00 (m, 1H), 1.40 (s, 9H)

MS: m/e 333.1 $(M+23)^+$

Intermediate 22 from Scheme 5

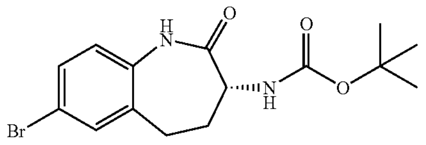

((R)-7-Bromo-2-oxo-2,3,4,5-tetrahydro-1H-1-benzazepin-3-yl)-carbamic acid tert-butyl Ester Step 1: Preparation of ((R)-7-bromo-2-oxo-2,3,4,5-tetrahydro-1H-1-benzazepin-3-yl)-carbamic acid tert-butyl Ester

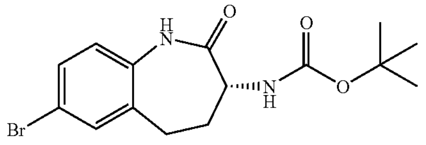

A round-bottom flask containing ((R)-2-oxo-2,3,4,5-tetrahydro-1H-benzo[b]azepin-3-yl)-carbamic acid tert-butyl ester (0.338 g, 1.20 mmol) was fitted with a stirbar and septa. Acetic acid (glacial, 5 mL) and bromine (0.37 g, 2.3 mmol) were added, in that order, giving a solution that was stirred at room temperature for 1.5 hours. The reaction was then poured into ethyl acetate (50 mL) and washed with saturated aqueous $NaHCO_3$ solution (2×50 mL). The organic layer was dried over $MgSO_4$, filtered and concentrated in vacuo to give an oil that was purified via flash chromatography on silica gel (10% to 50% ethyl acetate/hexanes linear gradient) to give the desired product.

$^1$H NMR ($CDCl_3$): 8.01 (s, 1H), 7.35 (m, 2H), 6.87 (d, J=8.5 Hz, 1H), 5.43 (d, J=7.5 Hz, 1H), 4.25 (m, 1H), 2.90 (m, 1H), 2.64 (m, 2H), 1.99 (m, 1H), 1.41 (s, 9H)

MS: m/e 379.1 $(M+23+2)^+$

Examples in TABLE 2 were prepared according to procedures described for EXAMPLES 73 and 74 in combination with the procedures described for the preparation of EXAMPLE 1, or by procedures described for the preparation of INTERMEDIATE 19 in combination with the procedures described for the preparation of EXAMPLES 73, 74 and 1, or by procedures described for the preparation of INTERMEDIATES 21 or 22 in combination with the procedures described for the preparation of EXAMPLE 1. The carbon atom marked with an * has the stereochemical configurations as depicted in the table below.

TABLE 2
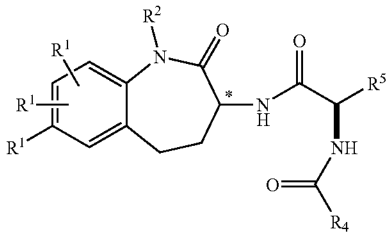
| Example # | $R^1$ | $R^2$ | * | $R^4$ | $R^5$ | (m/e) (M + H) |
|---|---|---|---|---|---|---|
| 75 | 7-CF3 | i-propyl | RS | OtBu | 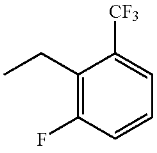 | 620.4 |
| 76 | 7,9-di-F | i-propyl | R | OtBu | 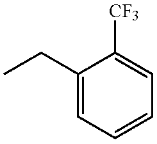 | 570.4 |
| 77 | 7,9-di-F | i-propyl | S | OtBu | 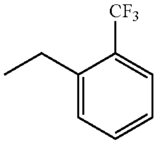 | 570.4 |
| 78 | 7,9-di-F | i-propyl | RS | OtBu | 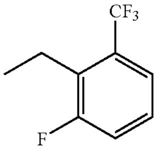 | 588.3 |
| 79 | 7,9-di-F | i-propyl | R | OtBu | 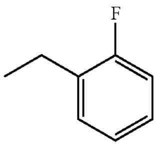 | 520.3 |
| 80 | 7,9-di-F | i-propyl | S | OtBu | 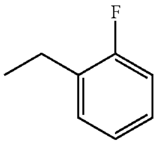 | 520.4 |
| 80 | 7,9-di-F | i-propyl | R | OtBu | 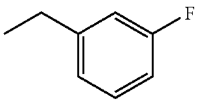 | 520.3 |
| 80 | 7,9-di-F | i-propyl | S | OtBu | 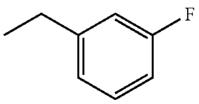 | 520.4 |

TABLE 2-continued
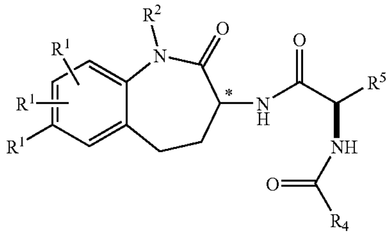
| Example # | $R^1$ | $R^2$ | * | $R^4$ | $R^5$ | (m/e) (M + H) |
|---|---|---|---|---|---|---|
| 81 | 7,9-di-F | i-propyl | R | OtBu | 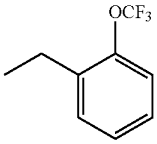 | 608.4 M + Na |
| 82 | 7,9-di-F | i-propyl | S | OtBu | 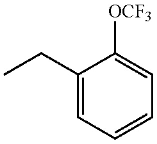 | 608.4 M + Na |
| 83 | 7-F | i-propyl | R | OtBu | 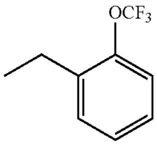 | 590.4 M + Na |
| 84 | 7-F | i-propyl | S | OtBu | 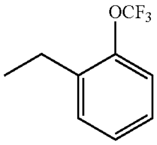 | 590.3 M + Na |
| 85 | 7-F | i-propyl | R | OtBu | 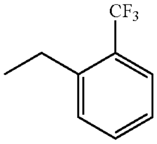 | 552.5 |
| 86 | 7-F | i-propyl | S | OtBu | 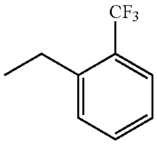 | 552.5 |
| 87 | 7-F | i-propyl | R | OtBu | 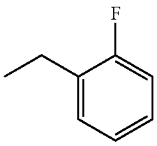 | 502.5 |
| 88 | 7-F | i-propyl | S | OtBu | 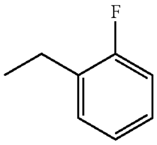 | 502.5 |

TABLE 2-continued
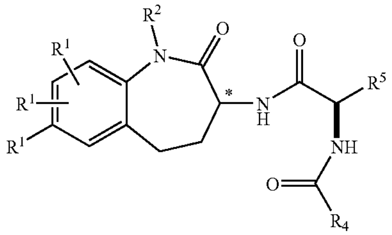
| Example # | $R^1$ | $R^2$ | * | $R^4$ | $R^5$ | (m/e) (M + H) |
|---|---|---|---|---|---|---|
| 89 | 8-F | i-propyl | R | OtBu | 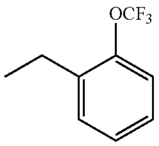 | 590.3 M + Na |
| 90 | 8-F | i-propyl | S | OtBu | 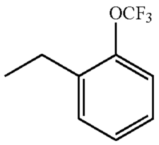 | 590.3 M + Na |
| 91 | 8-F | i-propyl | R | OtBu | 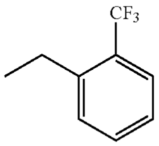 | 574.4 M + Na |
| 92 | 8-F | i-propyl | S | OtBu | 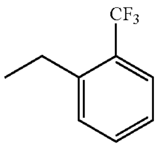 | 574.4 M + Na |
| 93 | 9-F | i-propyl | R | OtBu | 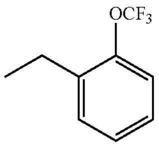 | 590.4 M + Na |
| 94 | 9-F | i-propyl | S | OtBu | 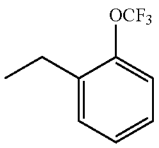 | 590.4 M + Na |
| 95 | 9-F | i-propyl | R | OtBu | 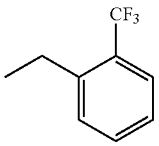 | 574.4 M + Na |
| 96 | 9-F | i-propyl | S | OtBu | 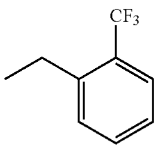 | 574.4 M + Na |

TABLE 2-continued
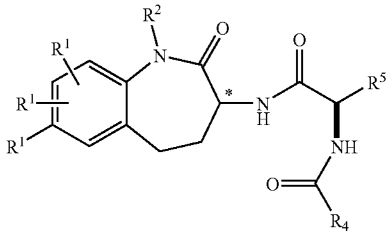
| Example # | $R^1$ | $R^2$ | * | $R^4$ | $R^5$ | (m/e) (M + H) |
|---|---|---|---|---|---|---|
| 97 | 8-$CF_3$ | i-propyl | R | OtBu | 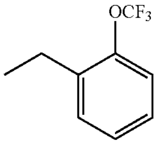 | 618.4 |
| 99 | 8-$CF_3$ | i-propyl | R | OtBu | 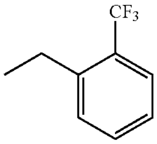 | 602.5 |
| 100 | 8-$CF_3$ | i-propyl | S | OtBu | 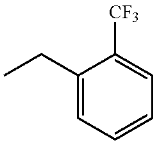 | 602.5 |
| 101 | 7-Br | i-propyl | R | OtBu | 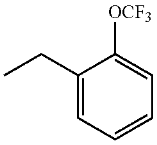 | 630.2 |
| 102 | 7,9-di-F | i-propyl | R | 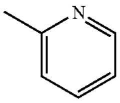 | 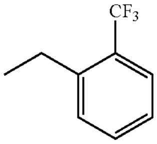 | 575.5 |
| 103 | 7,9-di-F | i-propyl | S | 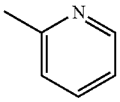 | 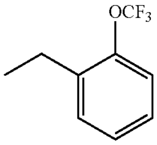 | 591.5 |
| 104 | 7-F | i-propyl | R | 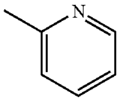 | 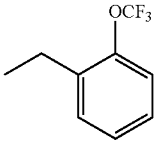 | 573.5 |
| 105 | 7-F | i-propyl | S | 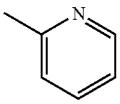 | 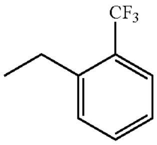 | 557.5 |

TABLE 2-continued
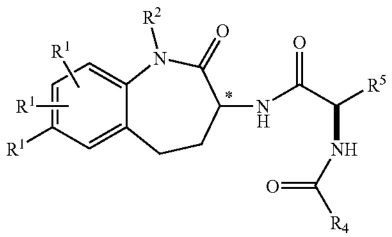
| Example # | $R^1$ | $R^2$ | * | $R^4$ | $R^5$ | (m/e) (M + H) |
|---|---|---|---|---|---|---|
| 106 | 7-Cl | i-propyl | R | OtBu | 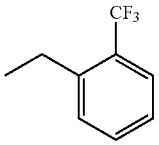 | 568.6 |
| 107 | 7-Cl | i-propyl | S | OtBu | 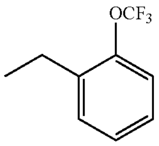 | 584.6 |
| 108 | 8-Cl | i-propyl | R | OtBu | 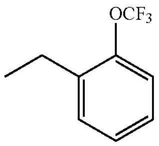 | 584.6 |
| 109 | 8-Cl | i-propyl | S | OtBu | 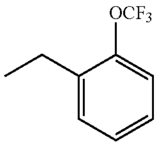 | 584.5 |
| 110 | 8-F | i-propyl | R | 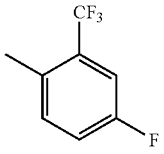 | 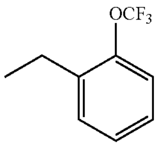 | 658.6 |
| 111 | 7-Cl | i-propyl | R | OtBu | 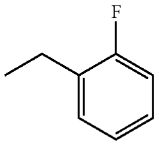 | 540.2 M + Na |
| 112 | 7-Cl | i-propyl | R | OtBu | 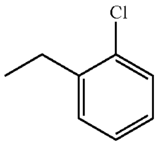 | 556.2 M + Na |
| 113 | 7-Cl | i-propyl | R | OtBu | 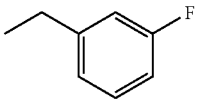 | 540.2 M + Na |

TABLE 2-continued
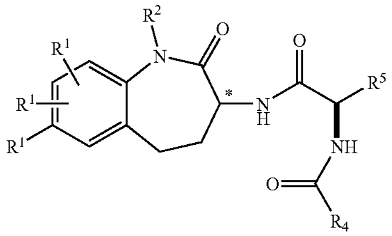
| Example # | $R^1$ | $R^2$ | * | $R^4$ | $R^5$ | (m/e) (M + H) |
|---|---|---|---|---|---|---|
| 114 | 7-Cl | i-propyl | R | 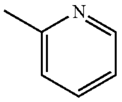 | 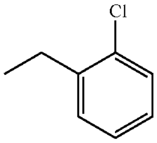 | 539.2 |
| 115 | 7-Cl | i-propyl | R | 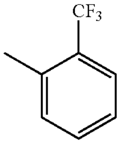 | 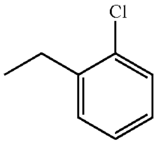 | 606.2 |
| 116 | 7-Cl | i-propyl | R | 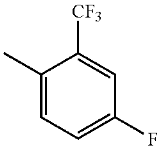 | 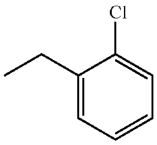 | 624.2 |
| 117 | 7-Cl | i-propyl | R | 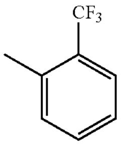 | 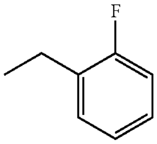 | 590.2 |
| 118 | 7-Cl | i-propyl | R | 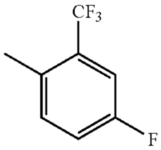 | 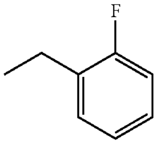 | 608.2 |
| 119 | 7-Cl | i-propyl | R | 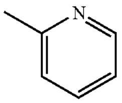 | 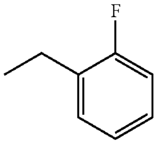 | 523.2 |
| 120 | 7-Cl | i-propyl | R | 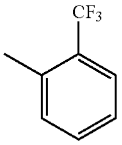 | 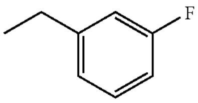 | 590.2 |
| 121 | 7-Cl | i-propyl | R | 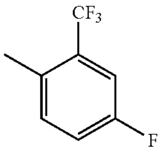 | 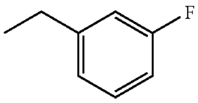 | 608.2 |

TABLE 2-continued
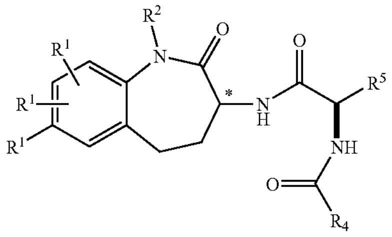
| Example # | $R^1$ | $R^2$ | * | $R^4$ | $R^5$ | (m/e) (M + H) |
|---|---|---|---|---|---|---|
| 122 | 7-Cl | i-propyl | R | 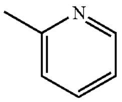 | 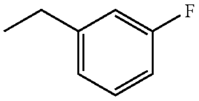 | 523.2 |
| 123 | 7-Cl | i-propyl | R | 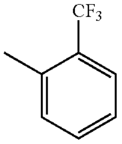 | 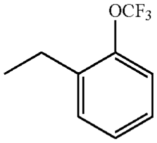 | 656.3 |
| 124 | 7-Cl | i-propyl | R | 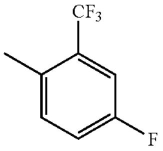 | 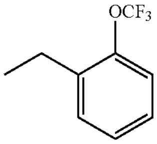 | 674.3 |
| 125 | 7-Cl | i-propyl | R | 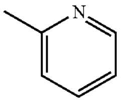 | 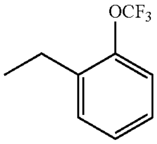 | 589.3 |
| 126 | 7-$CF_3$ | i-propyl | R | OtBu | 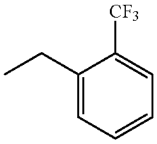 | 502.5 |
| 127 | 7-$CF_3$ | i-propyl | S | OtBu | 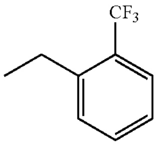 | 502.5 |
| 128 | 7-$CF_3$ | i-propyl | R | OtBu | 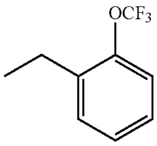 | 518.3 M – Boc + H |
| 129 | 7-$CF_3$ | i-propyl | S | OtBu | 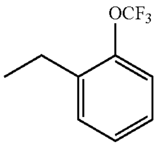 | 518.3 M – Boc + H |

TABLE 2-continued
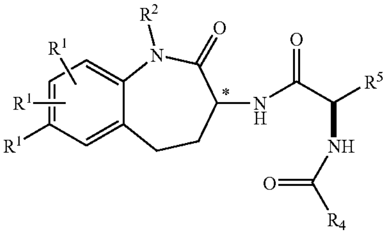
| Example # | $R^1$ | $R^2$ | * | $R^4$ | $R^5$ | (m/e) (M + H) |
|---|---|---|---|---|---|---|
| 130 | 7-$CF_3$ | i-propyl | R | OtBu | 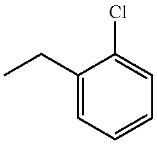 | 468.2 M − Boc + H |
| 131 | 7-$CF_3$ | i-propyl | S | OtBu | 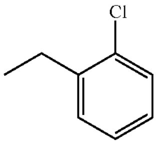 | 468.2 M − Boc + H |
| 132 | 7-$CF_3$ | i-propyl | R | OtBu | 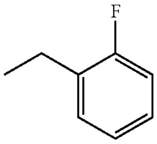 | 452.5 M − Boc + H |
| 133 | 7-$CF_3$ | i-propyl | S | OtBu | 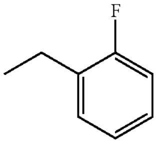 | 574.3 M + Na |
| 134 | 7-$CF_3$ | i-propyl | R | 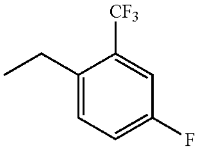 | 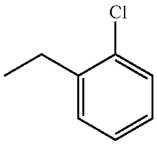 | 658.3 |
| 135 | 7-$CF_3$ | i-propyl | R | 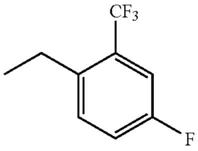 | 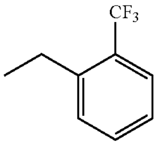 | 692.3 |
| 136 | 7-$CF_3$ | i-propyl | R | 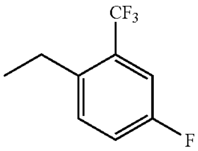 | 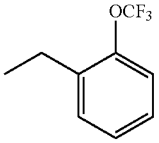 | 708.3 |
| 137 | 7-$CF_3$ | i-propyl | R | OtBu | 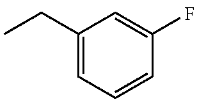 | 452.2 M − Boc + H |

TABLE 2-continued
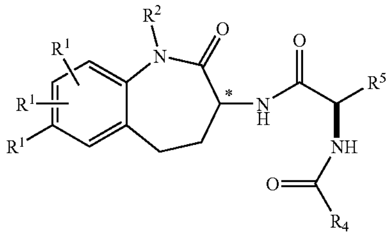
| Example # | $R^1$ | $R^2$ | * | $R^4$ | $R^5$ | (m/e) (M + H) |
|---|---|---|---|---|---|---|
| 138 | 7-F | i-propyl | R | 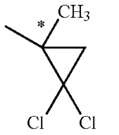 isomer 1 | 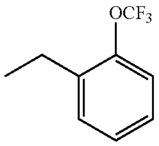 | 618.1 |
| 139 | 7-F | i-propyl | R | 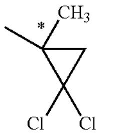 isomer 2 | 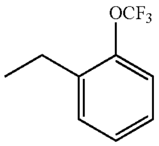 | 618.2 |
| 140 | 7-F | i-propyl | R | 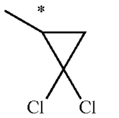 isomer 1 | 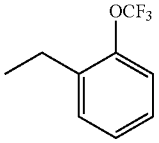 | 604.1 |
| 141 | 7-F | i-propyl | R | 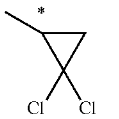 isomer 2 | 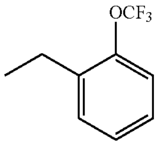 | 604.1 |
| 142 | 7-F | i-propyl | R | 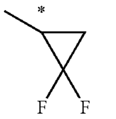 isomer 1 | 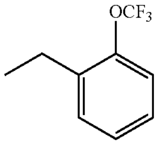 | 572.1 |
| 143 | 7-F | i-propyl | R | 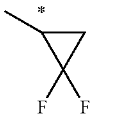 isomer 2 | 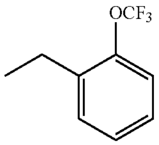 | 572.1 |
| 144 | 7-F | i-propyl | R | 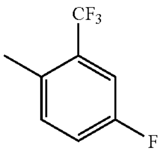 | 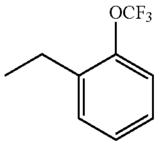 | 658.1 |
| 145 | 7-F | i-propyl | R | 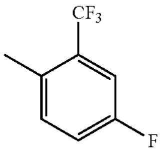 | 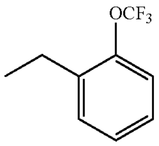 | 624.1 |

TABLE 2-continued
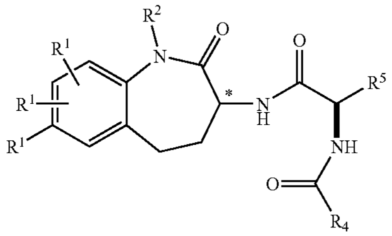
| Example # | $R^1$ | $R^2$ | * | $R^4$ | $R^5$ | (m/e) (M + H) |
|---|---|---|---|---|---|---|
| 146 | 7-F | i-propyl | R | 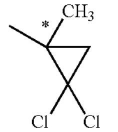 stereoisomeric mixture | 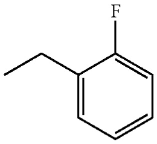 | 552.1 |
| 147 | 7-F | i-propyl | R | 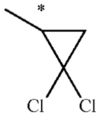 isomer 1 | 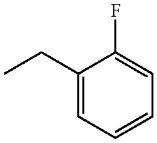 | 538.1 |
| 148 | 7-F | i-propyl | R | 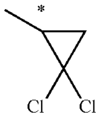 isomer 2 | 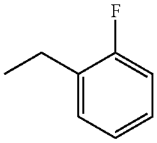 | 538.1 |
| 149 | 7-F | i-propyl | R | 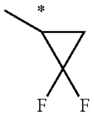 isomer 1 | 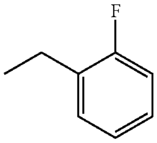 | 506.1 |
| 150 | 7-F | i-propyl | R | 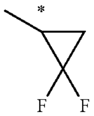 isomer 2 | 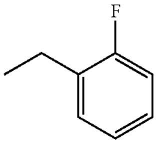 | 506.1 |
| 151 | 7-F | i-propyl | R | 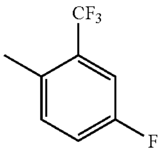 | 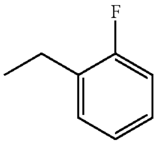 | 592.2 |
| 152 | 7-F | i-propyl | R | 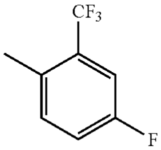 | 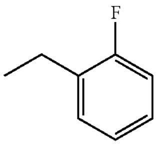 | 558.2 |
| 153 | 7-F | i-propyl | R | 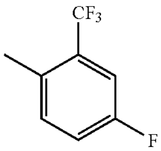 | 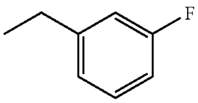 | 592.2 |

TABLE 2-continued
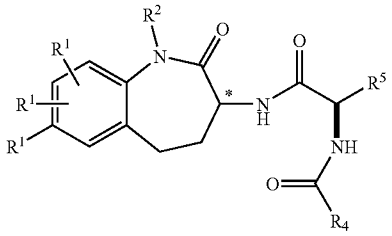
| Example # | $R^1$ | $R^2$ | * | $R^4$ | $R^5$ | (m/e) (M + H) |
|---|---|---|---|---|---|---|
| 154 | 7-F | i-propyl | R | 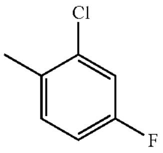 | 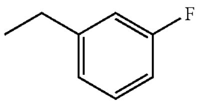 | 558.2 |
| 155 | 7-$CF_3$ | i-propyl | R | 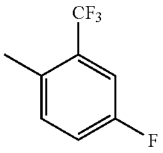 | 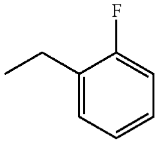 | 642.2 |
| 156 | 7-$CF_3$ | i-propyl | S | 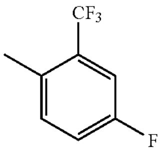 | 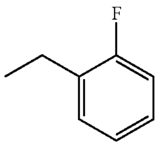 | 642.2 |
| 157 | 7-$OCF_3$ | i-propyl | R | 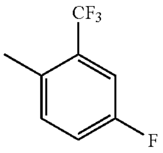 | 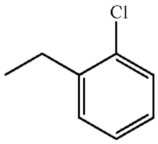 | 674.7 |
| 158 | 7-$OCF_3$ | i-propyl | S | 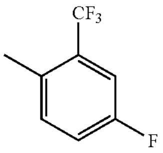 | 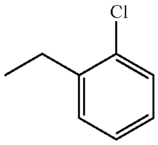 | 674.1 |
| 159 | 7-$OCF_3$ | i-propyl | R | OtBu | 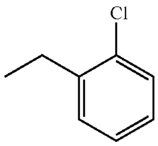 | 484.1 M − Boc + H |
| 160 | 7-$OCF_3$ | i-propyl | S | OtBu | 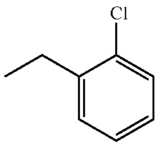 | 484.0 M − Boc + H |

TABLE 2-continued
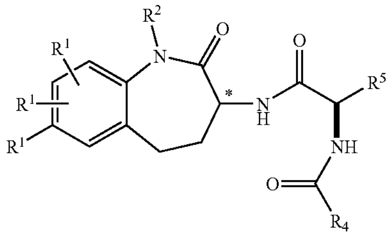
| Example # | $R^1$ | $R^2$ | * | $R^4$ | $R^5$ | (m/e) (M + H) |
|---|---|---|---|---|---|---|
| 161 | 7-$CF_3$ | i-propyl | R | 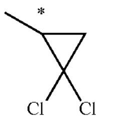 stereoisomeric mixture | 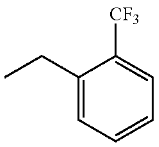 | 638.0 |
| 162 | 7-$CF_3$ | i-propyl | S | 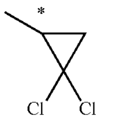 stereoisomeric mixture | 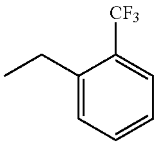 | 638.0 |
| 163 | 7-$OCF_3$ | i-propyl | R | OtBu | 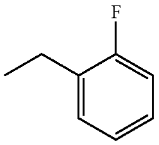 | 468.2 M − Boc + H |
| 164 | 7-$OCF_3$ | i-propyl | S | OtBu | 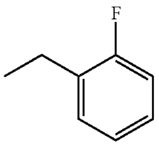 | 468.2 M − Boc + H |
| 165 | 7-$CF_3$ | i-propyl | R | 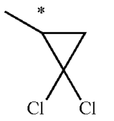 stereoisomeric mixture | 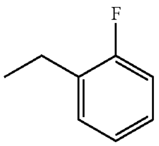 | 588.1 |
| 166 | 7-$CF_3$ | i-propyl | S | 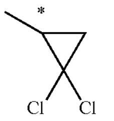 stereoisomeric mixture | 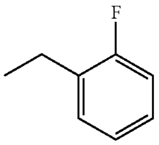 | 588.2 |
| 167 | 7-$CF_3$ | i-propyl | R | 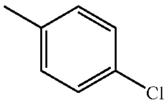 | 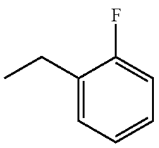 | 590.1 |
| 168 | 7-$CF_3$ | i-propyl | S | 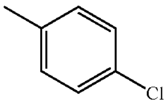 | 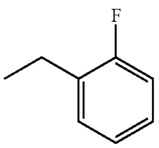 | 590.1 |

TABLE 2-continued
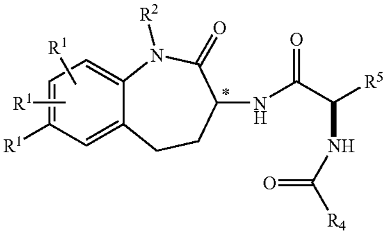
| Example # | $R^1$ | $R^2$ | * | $R^4$ | $R^5$ | (m/e) (M + H) |
|---|---|---|---|---|---|---|
| 169 | 7-$OCF_3$ | i-propyl | R | 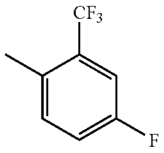 | 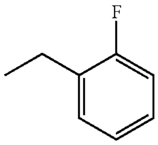 | 658.2 |
| 170 | 7-$OCF_3$ | i-propyl | S | 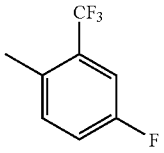 | 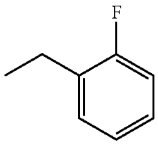 | 658.2 |
| 171 | 7-$CF_3$ | i-propyl | R | 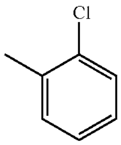 | 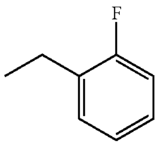 | 590.1 |
| 172 | 7-$CF_3$ | i-propyl | S | 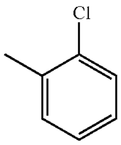 | 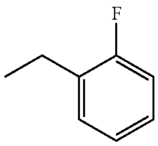 | 590.2 |
| 173 | 6,7,9-tri-F | i-propyl | R | OtBu | 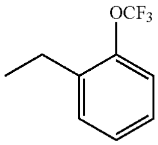 | 626.2 M + Na |
| 174 | 6,7,9-tri-F | i-propyl | S | OtBu | 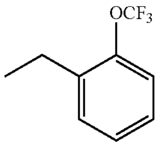 | 626.2 M + Na |
| 175 | 6,7,9-tri-F | i-propyl | R | OtBu | 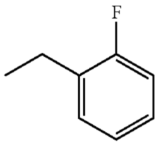 | 560.2 M + Na |
| 176 | 6,7,9-tri-F | i-propyl | S | OtBu | 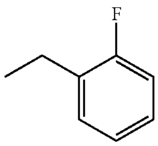 | 560.2 M + Na |

TABLE 2-continued
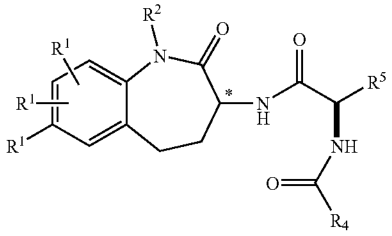
| Example # | $R^1$ | $R^2$ | * | $R^4$ | $R^5$ | (m/e) (M + H) |
|---|---|---|---|---|---|---|
| 177 | 6,7,9-tri-F | i-propyl | R | OtBu | 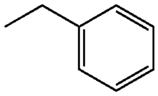 | 542.2 M + Na |
| 178 | 6,7,9-tri-F | i-propyl | S | OtBu | 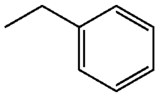 | 542.2 M + Na |
| 179 | 6,7,9-tri-F | i-propyl | R | 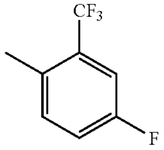 | 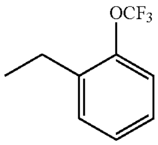 | 694.1 |
| 180 | 6,7,9-tri-F | i-propyl | R | 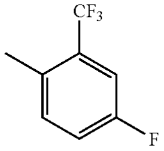 | 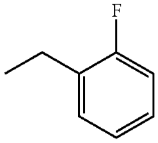 | 628.1 |
| 181 | 6,7,9-tri-F | i-propyl | R | 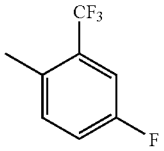 | 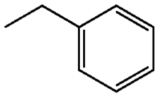 | 610.1 |
| 182 | 6,7,9-tri-F | i-propyl | R | 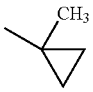 | 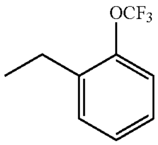 | 586.2 |
| 183 | 6,7,9-tri-F | i-propyl | R | 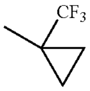 | 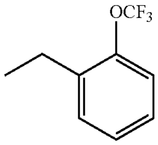 | 640.2 |
| 184 | 6,7,9-tri-F | i-propyl | R | 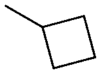 | 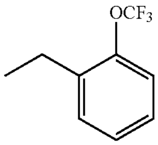 | 586.2 |

TABLE 2-continued
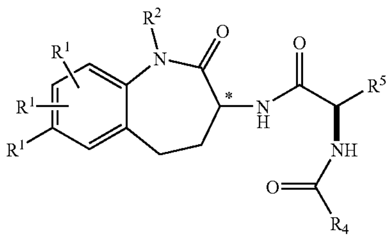
| Example # | $R^1$ | $R^2$ | * | $R^4$ | $R^5$ | (m/e) (M + H) |
|---|---|---|---|---|---|---|
| 185 | 6,7,9-tri-F | i-propyl | R | 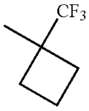 | 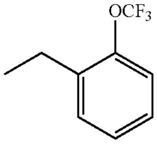 | 654.2 |
| 186 | 6,7,9-tri-F | i-propyl | R | 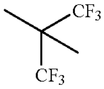 | 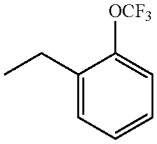 | 696.2 |
| 187 | 6,7,9-tri-F | i-propyl | R | 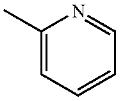 | 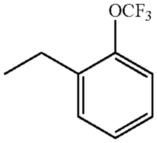 | 609.2 |
| 188 | 6,7,9-tri-F | i-propyl | R | 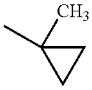 | 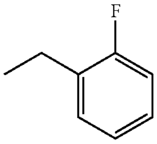 | 520.2 |
| 189 | 6,7,9-tri-F | i-propyl | R | 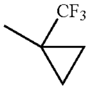 | 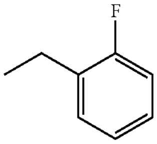 | 574.2 |
| 190 | 6,7,9-tri-F | i-propyl | R | 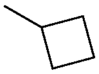 | 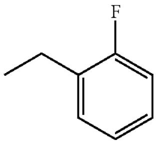 | 520.2 |
| 191 | 6,7,9-tri-F | i-propyl | R | 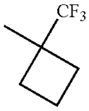 | 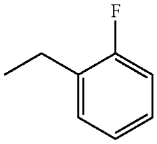 | 588.2 |
| 192 | 6,7,9-tri-F | i-propyl | R | 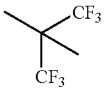 | 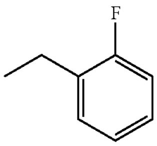 | 630.1 |

TABLE 2-continued
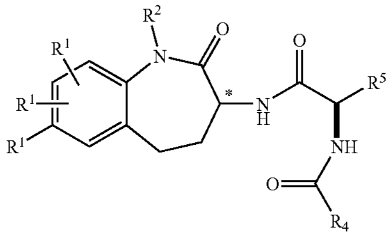
| Example # | $R^1$ | $R^2$ | * | $R^4$ | $R^5$ | (m/e) (M + H) |
|---|---|---|---|---|---|---|
| 193 | 6,7,9-tri-F | i-propyl | R | 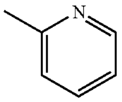 | 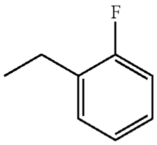 | 543.2 |
| 194 | 6,7,9-tri-F | i-propyl | S | 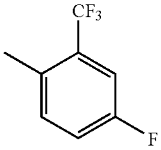 | 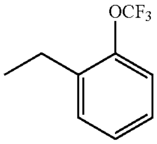 | 694.1 |
| 195 | 6,7,9-tri-F | i-propyl | S | 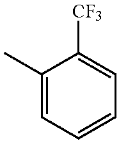 | 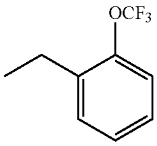 | 676.1 |
| 196 | 6,7,9-tri-F | i-propyl | S | 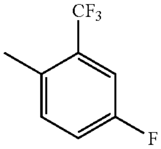 | 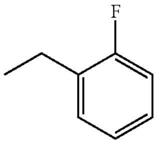 | 628.1 |
| 197 | 6,7,9-tri-F | i-propyl | S | 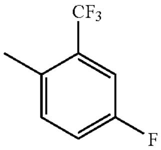 | 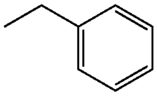 | 610.1 |
| 198 | 6,7,9-tri-F | i-propyl | R | 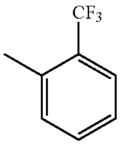 | 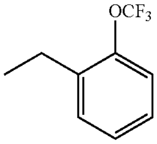 | 676.1 |
| 199 | 6,7,9-tri-F | i-propyl | R | 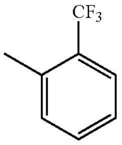 | 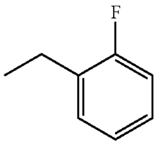 | 610.1 |
| 200 | 7,9-di-F | i-propyl | R | 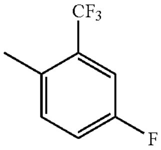 | 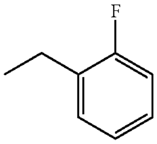 | 610.1 |

TABLE 2-continued
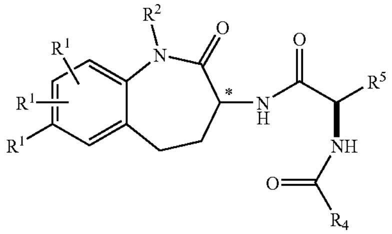
| Example # | $R^1$ | $R^2$ | * | $R^4$ | $R^5$ | (m/e) (M + H) |
|---|---|---|---|---|---|---|
| 201 | 7,9-di-F | i-propyl | R | 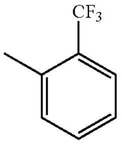 | 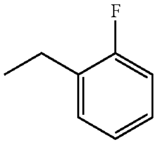 | 592.1 |
| 202 | 7,9-di-F | i-propyl | R | 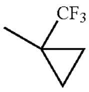 | 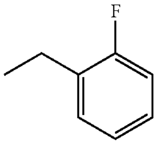 | 556.1 |
| 203 | 7,9-di-F | i-propyl | R | 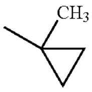 | 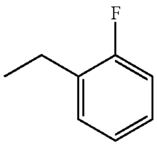 | 502.1 |
| 204 | 7,9-di-F | i-propyl | R | 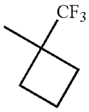 | 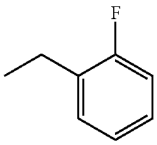 | 569.1 |
| 205 | 7,9-di-F | i-propyl | R | 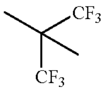 | 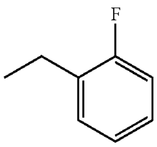 | 612.1 |
| 206 | 7-$OCF_3$ | i-propyl | R | 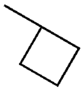 | 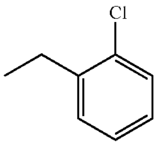 | 566.5 |
| 207 | 7,9-di-F | i-propyl | R | 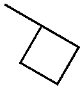 | 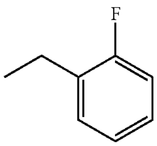 | 502.7 |
| 208 | 7-Cl | i-propyl | R | 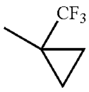 | 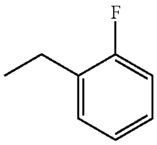 | 554.1 |

TABLE 2-continued
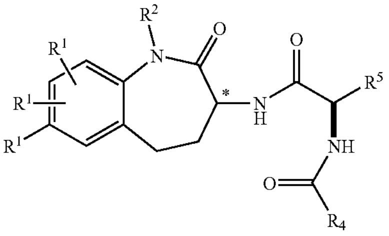
| Example # | $R^1$ | $R^2$ | * | $R^4$ | $R^5$ | (m/e) (M + H) |
|---|---|---|---|---|---|---|
| 209 | 7-Cl | i-propyl | R | 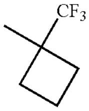 | 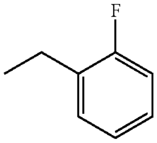 | 568.2 |
| 210 | 7-Cl | i-propyl | R | 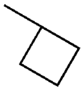 | 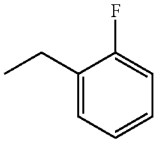 | 500.2 |
| 211 | 7-Cl | i-propyl | R | 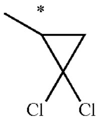 stereoisomeric mixture | 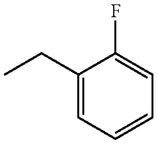 | 556.0 |
| 212 | 7-$CF_3$ | i-propyl | S | 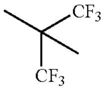 | 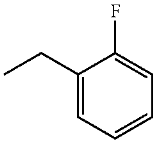 | 644.2 |
| 213 | 7-$OCF_3$ | i-propyl | R | 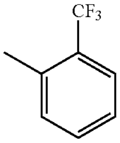 | 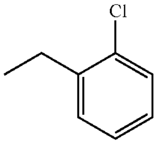 | 656.1 |
| 214 | 7-$CF_3$ | i-propyl | R | 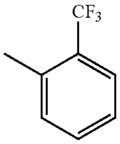 | 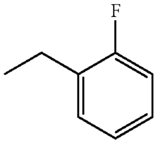 | 624.5 |
| 215 | 7-$CF_3$ | i-propyl | R | OtBu | 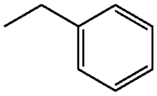 | 534.6 |
| 216 | 7-$CF_3$ | i-propyl | S | OtBu | 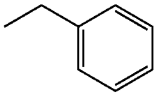 | 534.6 |

TABLE 2-continued
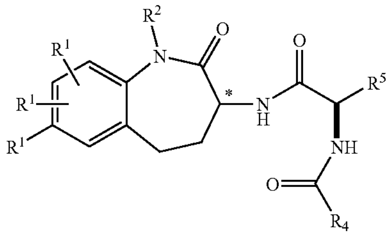
| Example # | $R^1$ | $R^2$ | * | $R^4$ | $R^5$ | (m/e) (M + H) |
|---|---|---|---|---|---|---|
| 217 | 7-$OCF_3$ | i-propyl | R | 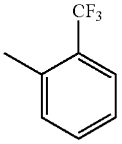 | 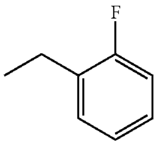 | 640.2 |
| 218 | 7-$OCF_3$ | i-propyl | S | 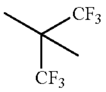 | 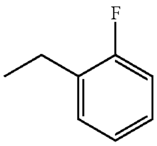 | 660.6 |
| 219 | 7-$OCF_3$ | i-propyl | R | 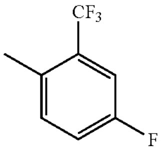 | 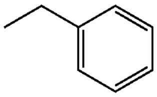 | 640.0 |
| 220 | 7-$OCF_3$ | i-propyl | R | OtBu | 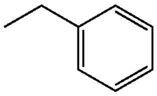 | 550.6 |
| 221 | 7,9-di-Cl | i-propyl | R | 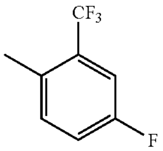 | 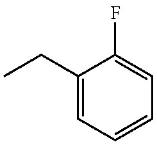 | 642.1 |
| 222 | 7-Cl, 9-F | i-propyl | R | OtBu | 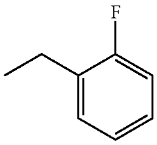 | 536.2 |
| 223 | 7-Cl, 9-F | i-propyl | R | 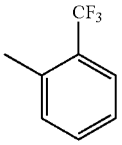 | 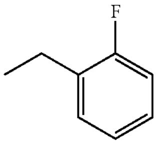 | 608.6 |
| 224 | 7-Cl, 9-F | i-propyl | R | 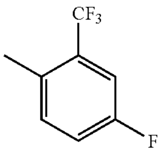 | 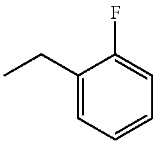 | 626.6 |

TABLE 2-continued
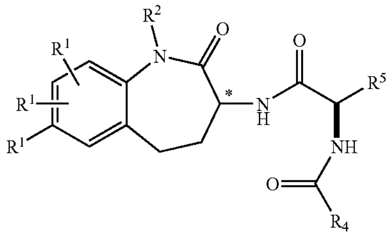
| Example # | $R^1$ | $R^2$ | * | $R^4$ | $R^5$ | (m/e) (M + H) |
|---|---|---|---|---|---|---|
| 225 | 7-Cl, 9-F | i-propyl | R | 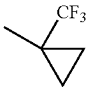 | 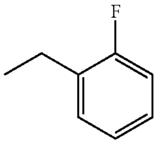 | 572.2 |
| 226 | 7-Cl | i-propyl | R | 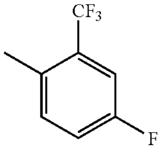 | 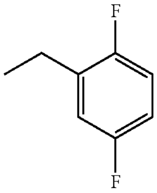 | 626.3 |
| 227 | 7-Cl, 9-F | i-propyl | R | 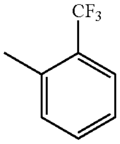 | 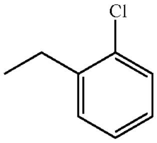 | 624.1 |
| 228 | 7-Cl, 9-F | i-propyl | R | 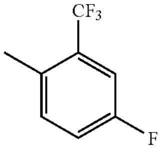 | 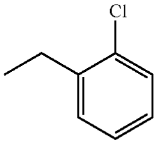 | 642.1 |
| 229 | 7-Cl, 9-F | i-propyl | R | 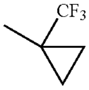 | 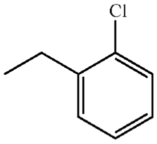 | 588.1 |
| 230 | 7-Cl, 9-F | i-propyl | R | 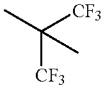 | 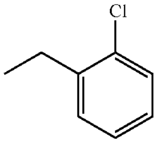 | 644.1 |
| 231 | 6,7,9-tri-F | 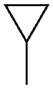 | R | 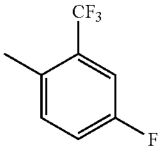 | 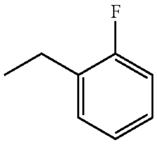 | 626.2 |
| 232 | 6,7,9-tri-F | 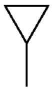 | R | 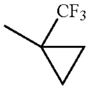 | 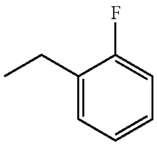 | 572.2 |

TABLE 2-continued
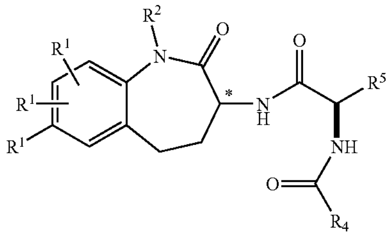
| Example # | $R^1$ | $R^2$ | * | $R^4$ | $R^5$ | (m/e) (M + H) |
|---|---|---|---|---|---|---|
| 233 | 6,7,9-tri-F | 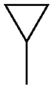 | R | 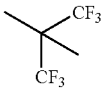 | 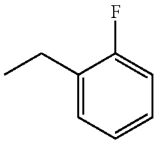 | 628.2 |
| 234 | 6,7,9-tri-F | 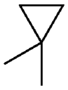 | R | 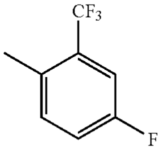 | 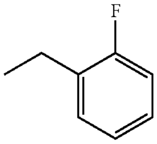 | 640.2 |
| 235 | 6,7,9-tri-F | 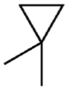 | R | 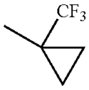 | 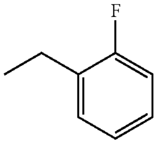 | 586.2 |
| 236 | 6,7,9-tri-F | 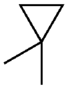 | R | 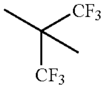 | 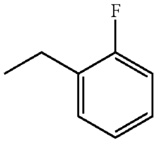 | 642.2 |
| 237 | 6,7,9-tri-F | 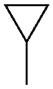 | R | 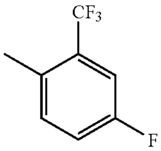 | 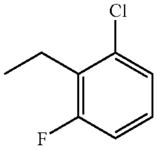 | 660.0 |
| 238 | 6,7,9-tri-F | 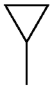 | R | 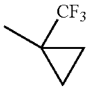 | 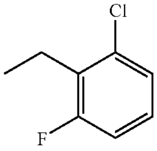 | 606.4 |
| 239 | 6,7,9-tri-F | 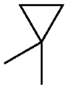 | R | 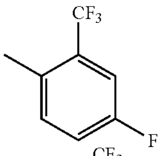 | 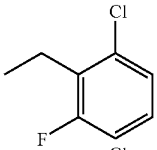 | 674.0 |
| 240 | 6,7,9-tri-F | 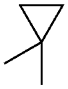 | R | 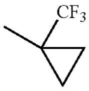 | 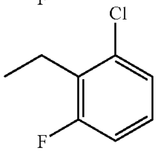 | 620.1 |

Intermediate 23 from Scheme 6

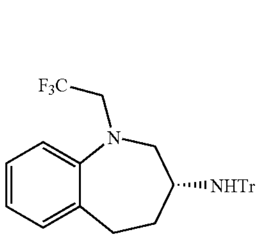

[(R)-1-(2,2,2-Trifluoro-ethyl)-2,3,4,5-tetrahydro-1H-1-benzazepin-3-yl]-trityl-amine Step 1: Preparation of (R)-1-(2,2,2-trifluoro-ethyl)-3-(trityl-amino)-1,3,4,5-tetrahydro-1-benzazepin-2-one

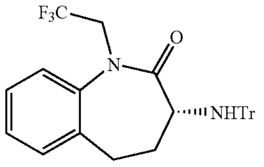

A round-bottom flask containing the product of Step 4 for the preparation of Example 1 (2.00 g, 4.80 mmol) was fitted with a stirbar and septa and flushed with nitrogen. Tetrahydrofuran (20 mL) was added, giving a solution that was cooled to 0° C. Sodium hydride (0.781 g, 60%/oil, 19.5 mmol) was added, and the reaction was stirred for 30 minutes. Trifluoromethanesulfonic acid-2,2,2-trifluoroethyl ester (2.26 g, 9.74 mmol) was then added, and stirring was continued with gradual warming to room temperature. After 18 hours, the reaction mixture was poured into ethyl acetate (75 mL) and washed first with 1:1 $H_2O$:saturated aqueous $NaHCO_3$ solution (2×30 mL), then with saturated aqueous NaCl solution (20 mL). The aqueous wash layers were combined and extracted with ethyl acetate (30 mL). The ethyl acetate layers were then combined, dried over $MgSO_4$, filtered and concentrated in vacuo to give an oil that was purified via flash chromatography on silica gel (5% to 15% ethyl acetate/hexanes linear gradient) to give the desired product.

$^1H$ NMR ($CDCl_3$): 7.39 (m, 6H), 7.30 (m, 1H), 7.16 (m, 11H), 6.81 (d, J=8.0 Hz, 1H), 4.35 (dddd, J=15.3, 9.1, 9.1, 9.1 Hz, 1H), 3.43 (dddd, J=16.9, 8.4, 8.4, 8.4 Hz, 1H), 3.26 (br s, 1H), 3.14 (br s, 1H), 2.67 (m, 1H), 2.50 (m, 2H), 2.19 (ddd, J=11.2, 11.2, 7.1 Hz, 1H)

MS: m/e 523.5 $(M+23)^+$

Step 2: Preparation of [(R)-1-(2,2,2-trifluoro-ethyl)-2,3,4,5-tetrahydro-1H-1-benzazepin-3-yl]-trityl-amine

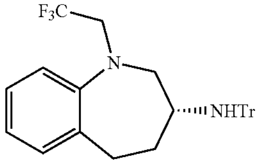

A round-bottom flask containing the product of Step 1 (1.94 g, 3.88 mmol) was fitted with a condenser, stirbar and septa and flushed with nitrogen. Tetrahydrofuran (40 mL) was added, giving a solution that was cooled to 0° C. Lithium aluminum hydride (0.77 g, 20 mmol) was added, and the reaction was then removed from the cooling bath and allowed to warm to room temperature. After one hour, the reaction was warmed to 60° C., then stirred an additional 17 hours. The reaction mixture was then cooled to room temperature and quenched via the sequential additions of $H_2O$ (0.77 mL), 10% aqueous sodium hydroxide solution (0.77 mL), and $H_2O$ (3×0.77 mL). The resulting mixture was stirred 10 minutes, diluted with ethyl acetate (100 mL), filtered through celite and concentrated in vacuo to give the desired product.

$^1H$ NMR ($CDCl_3$): 7.60 (m, 6H), 7.23 (m, 9H), 7.07 (m, 2H), 6.88 (m, 2H), 3.69 (m, 1H), 3.50 (br s, 2H), 2.87 (m, 2H), 2.67 (dd, J=14.2, 3.0 Hz, 1H), 2.55 (dd, J=13.0, 10.3 Hz, 1H), 2.32 (m, 1H), 1.52 (m, 1H), 1.27 (m, 1H)

MS: m/e 487.5 $(M+1)^+$

Examples in TABLE 3 were prepared according to the procedures described for the preparation of INTERMEDIATE 23 from Scheme 6 in combination with the procedures described for the preparation of EXAMPLE 1.

TABLE 3

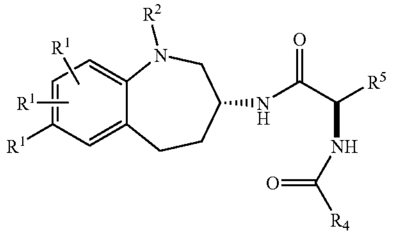

| Example # | $R^1$ | $R^2$ | $R^4$ | $R^5$ | (m/e) (M + H) |
|---|---|---|---|---|---|
| 241 | H | Me | OtBu | 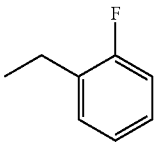 | 442.2 |
| 242 | H | $CH_2CF_3$ | OtBu | 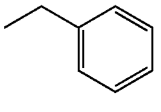 | 514.4 M + Na |
| 243 | H | $CH_2CF_3$ | OtBu | 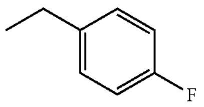 | 532.4 M + Na |
| 244 | H | $CH_2CF_3$ | OtBu | 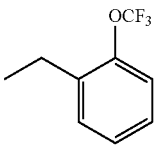 | 476.4 M − Boc + H |
| 245 | H | H | OtBu | 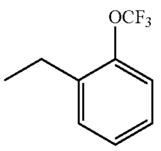 | 494.3 |

TABLE 3-continued

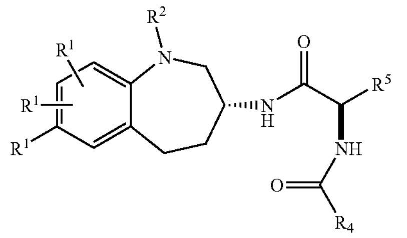

| Example # | $R^1$ | $R^2$ | $R^4$ | $R^5$ | (m/e) (M + H) |
|---|---|---|---|---|---|
| 246 | H | $CH_2CF_3$ | OtBu | 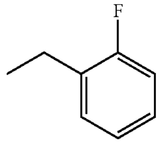 | 410.1 M − Boc + H |

Examples 247 and 248

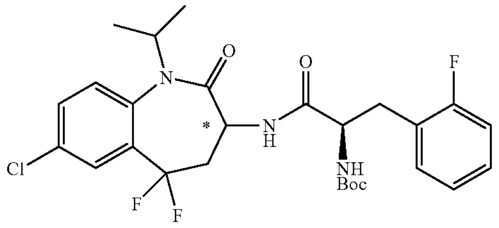

Diastereomeric Mixture

Diastereomer 1: [(R)-1-((R)-7-Chloro-5,5-difluoro-1-isopropyl-2-oxo-2,3,4,5-tetrahydro-1H-1-benzazepin-3-ylcarbamoyl)-2-(2-fluoro-phenyl)-ethyl]-carbamic acid tert-butyl Ester; And Diastereomer 2 [(R)-1-((S)-7-chloro-5,5-difluoro-1-isopropyl-2-oxo-2,3,4,5-tetrahydro-1H-1-benzazepin-3-ylcarbamoyl)-2-(2-fluoro-phenyl)-ethyl]-carbamic acid tert-butyl Ester Step 1: Preparation of (7-chloro-5-hydroxy-2-oxo-2,3,4,5-tetrahydro-1H-1-benzazepin-3-yl)-carbamic acid tert-butyl Ester

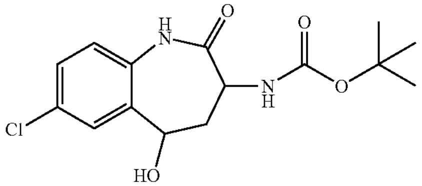

To a solution of (2,5-dioxo-2,3,4,5-tetrahydro-1H-1-benzazepin-3-yl)-carbamic acid t-butyl ester (intermediate 26 from Scheme 8, 1.0 g, 3.4 mmol) in methanol (10 mL) was added sodium borohydride (0.227 g, 6.02 mmol) in small portions over 5 min at room temperature. After 1 hour, the reaction mixture was concentrated and diluted with ethyl acetate. The ethyl acetate layer was washed sequentially with $H_2O$ and then brine, dried over $MgSO_4$, and concentrated to give the desired alcohol which was used without further purification in the next reaction described below.

A solution of the crude alcohol described above (1.0 g) and N-chlorosuccinimide (0.914 g, 6.84 mmol) in N,N-dimethylformamide (10 mL) was heated at 40° C. for 5 hours. The mixture was diluted with ethyl acetate, washed sequentially with water and then brine, dried over $MgSO_4$, and concentrated to dryness. The residue was purified by flash chromatography on silica gel (20-30% ethyl acetate/hexanes linear gradient) to provide the desired product.

$^1H$ NMR ($CDCl_3$): δ 7.65 (m, 1H), 7.31 (m, 2H), 7.00 (m, 1H), 5.47 (m, 1H), 5.15 (m, 1H), 4.22 (m, 1H), 2.62 (m, 1H), 2.41 (m, 1H), 1.40 (s, 9H)

MS: m/e 226.3 $(M\text{-}Boc)^+$

Step 2: Preparation of (7-chloro-1-isopropyl-2,5-dioxo-2,3,4,5-tetrahydro-1H-1-benzazepin-3-yl)-carbamic acid tert-butyl Ester

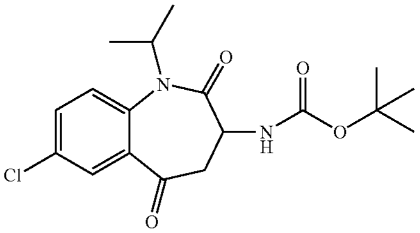

To a solution of the product from Step 1 (0.91 g, 2.8 mmol) in acetone (10 mL) was added Jones reagent (an excess). After 3 hours, the mixture was quenched with 2-propanol, and solid was filtered off. The filtrate was concentrated and dissolved in ethyl acetate. The ethyl acetate layer was washed sequentially with water and brine, dried over $MgSO_4$ and concentrated in vacuo to give a crude ketone product that was used without further purification in the next reaction described below.

To a solution of the crude ketone described above (750 mg, 2.31 mmol) in DMF at 0° C. was added cesium carbonate (326 mg, 1.12 mmol). After 30 minutes, 2-iodopropane was added. After an additional 1 hour, the mixture was diluted with water and extracted with ethyl acetate. The combined ethyl acetate layers were washed sequentially with water and brine, dried over $MgSO_4$, and concentrated to dryness. The residue was purified by flash chromatography on silica gel (20 to 30% ethyl acetate/hexanes linear gradient) to give the desired product.

$^1H$ NMR ($CDCl_3$) δ 7.51 (m, 2H), 7.25 (d, J=8.5 Hz, 1H), 5.76 (d, J=7.0 Hz, 1H), 4.80 (m, 1H), 4.59 (septet, J=7.0 Hz, 1H), 3.27 (m, 1H), 2.83 (m, 1H), 1.48 (d, J=7.0 Hz, 3H), 1.44 (s, 9H), 1.14 (d, J=7.0 Hz, 3H)

MS: m/e 267.1 $(M-1)^+$

Step 3: Preparation of (7-chloro-5,5-difluoro-1-isopropyl-2-oxo-2,3,4,5-tetrahydro-1H-1-benzazepin-3-yl)-carbamic acid tert-butyl Ester

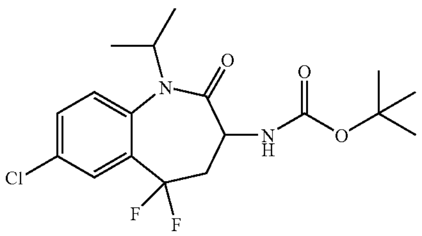

To a solution of the product from Step 2 (300 mg, 0.82 mmol) in dichloromethane (5 mL) was added [bis(2-methoxyethyl)-amino]sulfur trifluoride (726 mg, 3.28 mmol). After 24 hours, the resulting solution was diluted with ethyl acetate, washed sequentially with water and brine, dried over $MgSO_4$, and concentrated to dryness. The residue was purified by flash chromatography on silica gel (30% ethyl acetate/hexanes) to give desired product.

$^1$H NMR ($CDCl_3$) δ 7.60 (m, 1H), 7.47 (m, 10H), 7.24 (m, 1H), 5.7 (m, 1H), 4.62 (septet, J=7.0 Hz, 1H), 3.03 (m, 1H), 2.55 (m, 1H), 1.45 (d, J=7.0 Hz, 3H), 1.44 (s, 9H), 1.15 (d, J=7.0 Hz, 3H)

MS: m/e 289.1 $(M-Boc)^+$

Step 4: Preparation of [(R)-1-((R)-7-chloro-5,5-difluoro-1-isopropyl-2-oxo-2,3,4,5-tetrahydro-1H-1-benzazepin-3-ylcarbamoyl)-2-(2-fluoro-phenyl)-ethyl]-carbamic acid tert-butyl ester (diastereomer 1); and [(R)-1-((S)-7-chloro-5,5-difluoro-1-isopropyl-2-oxo-2,3,4,5-tetrahydro-1H-1-benzazepin-3-ylcarbamoyl)-2-(2-fluoro-phenyl)-ethyl]-carbamic acid tert-butyl ester (diastereomer 2)

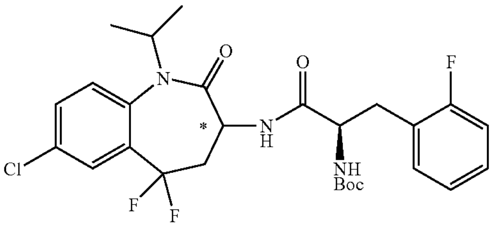

To a solution of the product from Step 3 (183 mg, 0.470 mmol) in methanol was added hydrochloric acid. After 5 hours, the resulting mixture was concentrated to dryness to give a crude amine hydrochloride salt which was used without further purification in the next step described below.

To a suspension of the crude amine hydrochloride salt described above (120 mg, 0.370 mmol) in dichloromethane (6 mL) were added diisopropylethylamine (0.35 mL, 1.9 mmol), N-Boc-D-2-fluorophenylalanine (105 mg, 0.371 mmol), 1-hydroxybenzotriazole (65 mg, 0.48 mmol) and benzotriazol-1-yloxytris(dimethylamino)phosphonium hexafluorophosphate (213 mg, 0.481 mmol). After 1 hour, the mixture was diluted with ethyl acetate, washed sequentially with water and brine, dried over $MgSO_4$ and concentrated in vacuo to give a residue that was purified by flash chromatography on silica gel (30% ethyl acetate/hexanes) to give the desired product as a mixture of two diastereomers. This mixture was further purified via HPLC (Chiralcel AD column, 15% 2-propanol/heptane) to give a faster-eluting diastereomer (d1) and a slower-eluting diastereomer (d2).

d1 $^1$H NMR ($CDCl_3$) δ 7.64 (m, 2H), 7.47 (d, J=8.5 Hz, 1H), 7.24 (m, 2H), 7.09-7.01 (m, 2H), 4.53 (septet, J=7.0 Hz, 1H), 4.36 (m, 2H), 3.20 (dd, J=10.0, 5.0 Hz, 1H), 2.85 (m, 2H), 2.6 (m, 1H), 1.46 (d, J=7.0 Hz, 3H), 1.35 (s, 9H), 1.13 (d, J=7.0 Hz, 3H)

d1 MS m/e 454.1 $(M-Boc)^+$ d2 $^1$H NMR ($CDCl_3$) δ 7.62 (m, 2H), 7.47 (d, J=8.5 Hz, 1H), 7.23 (m, 2H), 7.09-7.02 (m, 2H), 4.55 (septet, J=7.0 Hz, 1H), 4.36 (m, 2H), 3.13 (m, 1H), 3.20 (m, 1H), 2.90-2.64 (m, 2H), 2.43 (m, 1H), 1.46 (d, J=7.0 Hz, 3H), 1.35 (s, 9H), 1.13 (d, J=7.0 Hz, 3H)

d2 MS m/e 454.1 $(M-Boc)^+$

Intermediate 25 from Scheme 7

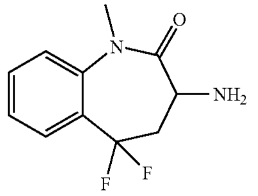

3-Amino-5,5-difluoro-1-methyl-1,3,4,5-tetrahydro-1-benzazepin-2-one

Step 1: Preparation of 3-amino-5,5-difluoro-1-methyl-1,3,4,5-tetrahydro-1-benzazepin-2-one

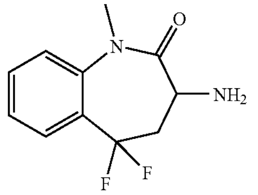

A round-bottom flask containing known compound 24 from Scheme 7 (0.990 g, 3.26 mmol) was fitted with a condenser, stirbar and septa and flushed with nitrogen. 1,2-Dichloroethane (10 mL) and (diethylamino)sulfur trifluoride (2.20 mL, 16.3 mmol) were added, and the reaction was then warmed to 65° C. After 36 hours, the reaction mixture was cooled to room temperature, poured into saturated aqueous $NaHCO_3$ solution and extracted several times with dichloromethane. The organic extracts were combined, dried over $MgSO_4$, filtered and concentrated in vacuo to give a residue that was purified via flash chromatography on silica gel (0% to 50% ethyl acetate/hexanes linear gradient) to give the desired difluorinated product which was used in the next reaction described below.

A round-bottom flask containing the difluorinated product described above (0.770 g, 2.36 mmol) was fitted with a stirbar and septa. A 3:7 mixture of trifluoroacetic acid:dichloromethane was added, giving a solution which was stirred at room temperature for 18 hours. The reaction was then concentrated in vacuo to yield the desired deprotected product.

MS: m/e 227.2 $(M+1)^+$

Examples in TABLE 4 were prepared according to the procedures described for the preparation of EXAMPLES 247 and 248 in combination with the procedures described for the preparation of EXAMPLE 1, or by procedures described for the preparation of INTERMEDIATE 25 from Scheme 7 in combination with the procedures described for the preparation of EXAMPLE 1. The carbon atoms marked with an * have the stereochemical configurations as depicted in the table below.

TABLE 4

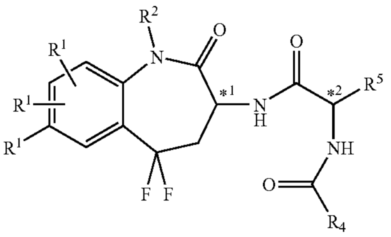

| Example # | $R^1$ | $R^2$ | *1, *2 | $R^4$ | $R^5$ | (m/e) (M + H) |
|---|---|---|---|---|---|---|
| 249 | H | $CH_3$ | RS,R | OtBu | 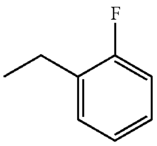 | 392.2 M − Boc + H |
| 250 | H | i-propyl | RS,R | OtBu | 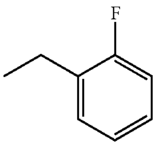 | 420.2 M − Boc + H |
| 251 | H | i-propyl | RS,R | OtBu | 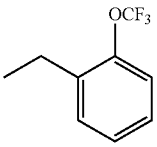 | 486.4 M − Boc + H |
| 252 | 7-Cl | i-propyl | R,R | OtBu | 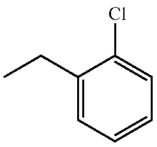 | 470.0 M − Boc + H |
| 253 | 7-Cl | i-propyl | S,R | OtBu | 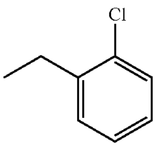 | 470.0 M − Boc + H |
| 254 | 7-Cl | i-propyl | S,R | 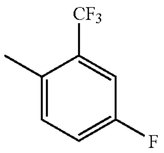 | 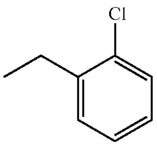 | 660.1 M − Boc + H |
| 255 | 7-Cl | i-propyl | R,R | 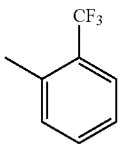 | 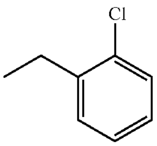 | 642.1 M − Boc + H |

TABLE 4-continued

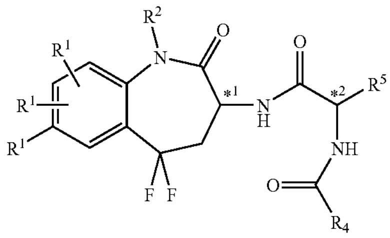

| Example # | $R^1$ | $R^2$ | *1, *2 | $R^4$ | $R^5$ | (m/e) (M + H) |
|---|---|---|---|---|---|---|
| 256 | 7-Cl | i-propyl | S,R | 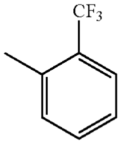 | 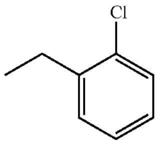 | 642.1 M − Boc + H |

The following in vitro and in vivo assays were used in assessing the biological activity of the instant compounds.

Compound Evaluation (In Vitro Assay):

The identification of inhibitors of the sodium channel is based on the ability of sodium channels to cause cell depolarization when sodium ions permeate through agonist-modified channels. In the absence of inhibitors, exposure of an agonist-modified channel to sodium ions will cause cell depolarization. Sodium channel inhibitors will prevent cell depolarization caused by sodium ion movement through agonist-modified sodium channels. Changes in membrane potential can be determined with voltage-sensitive fluorescence resonance energy transfer (FRET) dye pairs that use two components, a donor coumarin ($CC_2$-DMPE) and an acceptor oxanol (DiSBAC$_2$(3)). Oxanol is a lipophilic anion and distributes across the membrane according to membrane potential. In the presence of a sodium channel agonist, but in the absence of sodium, the inside of the cell is negative with respect to the outside, oxanol is accumulated at the outer leaflet of the membrane and excitation of coumarin will cause FRET to occur. Addition of sodium will cause membrane depolarization leading to redistribution of oxanol to the inside of the cell, and, as a consequence, to a decrease in FRET. Thus, the ratio change (donor/acceptor) increases after membrane depolarization. In the presence of a sodium channel inhibitor, cell depolarization will not occur, and therefore the distribution of oxanol and FRET will remain unchanged.

Cells stably transfected with the PN1 sodium channel (HEK-PN1) were grown in polylysine-coated 96-well plates at a density of ca. 140,000 cells/well. The media was aspirated, and the cells were washed with PBS buffer, and incubated with 100 μL of 10 μm $CC_2$-DMPE in 0.02% pluronic acid. After incubation at 25° C. for 45 min, media was removed and cells were washed 2× with buffer. Cells were incubated with 100 μL of DiSBAC$_2$(3) in TMA buffer containing 20 μM veratridine, 20 nM brevetoxin-3, and test sample. After incubation at 25° C. for 45 min in the dark, plates were placed in the VIPR instrument, and the fluorescence emission of both $CC_2$-DMPE and DiSBAC$_2$(3) recorded for 10 s. At this point, 100 μL of saline buffer was added to the wells to determine the extent of sodium-dependent cell depolarization, and the fluorescence emission of both dyes recorded for an additional 20 s. The ratio $CC_2$-DMPE/DiSBAC$_2$(3), before addition of saline buffer equals 1. In the absence of inhibitors, the ratio after addition of saline buffer is >1.5. When the sodium channel has been completely inhibited by either a known standard or test compound, this ratio remains at 1. It is possible, therefore, to titrate the activity of a sodium channel inhibitor by monitoring the concentration-dependent change in fluorescence ratio.

Electrophysiological Assays (In Vitro Assays):

Cell preparation: A HEK-293 cell line stably expressing the PN1 sodium channel subtype was established in-house. The cells were cultured in MEM growth media (Gibco) with 0.5 mg/mL G418, 50 units/mL Pen/Strep and 1 mL heat-inactivated fetal bovine serum at 37° C. and 10% $CO_2$. For electrophysiological recordings, cells were plated on 35 mm dishes coated with poly-D-lysine.

Whole-cell recordings: HEK-293 cells stably expressing the PN1 sodium channel subtype were examined by whole cell voltage clamp (Hamill et al. Pfluegers Archives 391:85-100 (1981)) using an EPC-9 amplifier and Pulse software (HEKA Electronics, Lamprecht, Germany). Experiments were performed at room temperature. Electrodes were fire-polished to resistances of 2-4 MΩ. Voltage errors were minimized by series resistance compensation, and the capacitance transient was canceled using the EPC-9's built-in circuitry. Data were acquired at 50 kHz and filtered at 7-10 kHz. The bath solution consisted of 40 mM NaCl, 120 mM NMDG Cl, 1 mM KCl, 2.7 mM $CaCl_2$, 0.5 mM $MgCl_2$, 10 mM NMDG HEPES, pH 7.4, and the internal (pipet) solution contained 110 mM Cs-methanesulfonate, 5 mM NaCl, 20 mM CsCl, 10 mM CsF, 10 mM BAPTA (tetra Cs salt), 10 mM Cs HEPES, pH 7.4.

The following protocols were used to estimate the steady-state affinity of compounds for the resting and inactivated state of the channel ($K_r$ and $K_i$, respectively):

1. 8 ms test-pulses to depolarizing voltages from −60 Mv to +50 Mv from a holding potential of −90 Mv were used to construct current-voltage relationships (IV-curves). A voltage near the peak of the IV-curve (typically −10 or 0 Mv) was used as the test-pulse voltage throughout the remainder of the experiment.

2. Steady-state inactivation (availability) curves were constructed by measuring the current activated during an 8 ms test-pulse following 10 s conditioning pulses to potentials ranging from −120 Mv to −10 Mv.

3. Compounds were applied at a holding potential at which 20-50% of the channels was inactivated and sodium channel blockage was monitored during 8 ms test pulses at 2 s intervals.

4. After the compounds equilibrated, the voltage-dependence of steady-state inactivation in the presence of compound was determined according to protocol 2) above. Compounds that block the resting state of the channel decrease the current elicited during test-pulses from all holding potentials, whereas compounds that primarily block the inactivated state shift the mid-point of the steady-state inactivation curve. The maximum current at negative holding potentials ($I_{max}$) and the difference in the mid-points of the steady-state inactivation curves ($\Delta V$) in control and in the presence of a compound were used to calculate $K_r$ and $K_i$ using the following equations:

$$K_r = \frac{[\text{Drug}] * I_{Max,Drug}}{I_{Max,Control} - I_{Max,Drug}}$$

$$K_i = \frac{[\text{Drug}]}{\left(1 + \frac{[\text{Drug}]}{K_r}\right) * e^{\frac{-\Delta V}{k}} - 1}$$

In cases where the compound did not affect the resting state, $K_i$ was calculated using the following equation:

$$K_i = \frac{[\text{Drug}]}{e^{\frac{-\Delta V}{k}} - 1}$$

Rat Formalin Paw Test (In Vivo Assay):

Compounds were assessed for their ability to inhibit the behavioral response evoked by a 50 mL injection of formalin (5%). A metal band was affixed to the left hind paw of male Sprague-Dawley rats (Charles River, 200-250 g) and each rat was conditioned to the band for 60 min within a plastic cylinder (15 cm diameter). Rats were dosed with either vehicle or a test compound either before (local) or after (systemic) formalin challenge. For local administration, compounds were prepared in a 1:4:5 vehicle of ethanol, PEG400 and saline (EPEGS) and injected subcutaneously into the dorsal surface of the left hind paw 5 min prior to formalin. For systemic administration, compounds were prepared in either a EPEGS vehicle or a Tween80 (10%)/sterile water (90%) vehicle and were injected i.v. (via the lateral tail vein 15 min after formalin) or p.o. (60 min before formalin). The number of flinches was counted continuously for 60 min using an automated nociception analyzer (UCSD Anesthesiology Research, San Diego, Calif.). Statistical significance was determined by comparing the total flinches detected in the early (0-10 min) and late (11-60 min) phase with an unpaired t-test.

In Vivo Assay Using Rat CFA Model:

Unilateral inflammation was induced with a 0.2 mL injection of complete Freund's adjuvant (CFA: *Mycobacterium tuberculosis*, Sigma; suspended in an oil/saline (1:1) emulsion; 0.5 mg *Mycobacterium*/Ml) in the plantar surface of the left hindpaw. This dose of CFA produced significant hind paw swelling but the animals exhibited normal grooming behavior and weight gain over the course of the experiment. Mechanical hyperalgesia was assessed 3 days after tissue injury using a Randall-Selitto test. Repeated Measures ANOVA, followed by Dunnett's Post Hoc test.

SNL: Mechanical Allodynia (In Vivo Assay):

Tactile allodynia was assessed with calibrated von Frey filaments using an up-down paradigm before and two weeks following nerve injury. Animals were placed in plastic cages with a wire mesh floor and allowed to acclimate for 15 min before each test session. To determine the 50% response threshold, the von Frey filaments (over a range of intensities from 0.4 to 28.8 g) were applied to the mid-plantar surface for 8 s, or until a withdrawal response occurred. Following a positive response, an incrementally weaker stimulus was tested. If there was no response to a stimulus, then an incrementally stronger stimulus was presented. After the initial threshold crossing, this procedure was repeated for four stimulus presentations per animal per test session. Mechanical sensitivity was assessed 1 and 2 hr post oral administration of the test compound.

The compounds described in this invention displayed sodium channel blocking activity of from about <0.1 μM to about <50 μM in the in vitro assays described above. It is advantageous that the compounds display sodium channel blocking activity of <5 μM in the in vitro assays. It is more advantageous that the compounds display sodium channel blocking activity of <1 μM in the in vitro assays. It is even more advantageous that the compounds display sodium channel blocking activity of <0.5 μM in the in vitro assays. It is still more advantageous that the compounds display sodium channel blocking activity of <0.1 μM in the in vitro assays.

What is claimed is:

1. A compound represented by Formula (I):

(I)

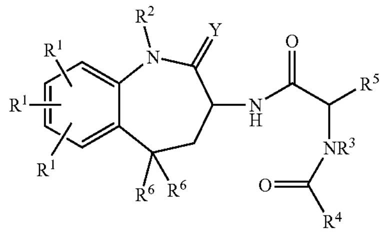

or a pharmaceutically acceptable salts or individual stereoisomer thereof, wherein $R^1$ is selected from the group consisting of
- hydrogen,
- halogen,
- cyano,
- $C_{1-6}$ alkyl, unsubstituted or substituted with one to five halogens, and
- —O—$C_{1-6}$ alkyl, unsubstituted or substituted with one to five halogens;

Y is O or $H_2$;

$R^2$ is selected from the group consisting of
- hydrogen,
- $C_{1-6}$ alkyl, unsubstituted or substituted with one to six halogens,
- $C_{1-6}$ alkenyl,
- $C_{1-6}$ alkynyl,
- $C_{1-6}$ alkoxy-$C_{1-6}$ alkyl, unsubstituted or substituted with one to six halogens, and
- $C_{3-6}$ cycloalkyl-$C_{0-6}$alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens;

$R^3$ is selected from the group consisting of

Hydrogen, and $C_{1-6}$ alkyl, unsubstituted or substituted with one to six halogens;

$R^4$ is selected from the group consisting of $C_{1-10}$ alkyl, unsubstituted or substituted with one to six halogens, —O—$C_{1-10}$ alkyl, unsubstituted or substituted with one to six halogens, $C_{3-10}$ cycloalkyl-$C_{0-6}$ alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens, $(CH_2)_n$—$C_{6-10}$aryl, wherein aryl is unsubstituted or substituted with one to five substituents independently selected from halogen, cyano, $C_{1-6}$ alkyl and $C_{1-6}$ alkoxy, wherein alkyl and alkoxy are unsubstituted or substituted with one to six halogens, and $(CH_2)_n$—$C_{5-10}$heteroaryl, wherein heteroaryl is unsubstituted or substituted with one to five substituents independently selected from halogen, $C_{1-6}$ alkyl and $C_{1-6}$ alkoxy, wherein alkyl and alkoxy are unsubstituted or substituted with one to six halogens;

$R^5$ is selected from the group consisting of $(CH_2)_n$—$C_{6-10}$aryl, wherein aryl is unsubstituted or substituted with one to five substituents independently selected from hydroxy, halogen, cyano, $C_{1-6}$ alkyl and $C_{1-6}$ alkoxy, wherein alkyl and alkoxy are unsubstituted or substituted with one to six halogens, and $(CH_2)_n$—$C_{5-10}$heteroaryl, wherein heteroaryl is unsubstituted or substituted with one to five substituents independently selected from halogen, $C_{1-6}$ alkyl and $C_{1-6}$ alkoxy, wherein alkyl and alkoxy are unsubstituted or substituted with one to six halogens;

$R^6$ is selected from the group consisting of

Hydrogen, and halogen; and n is 0, 1 or 2, provided that $R^5$ is not $(CH_2)$phenyl when R2 is hydrogen.

2. The compound according to claim 1 represented by Formula (Ia):

(Ia)

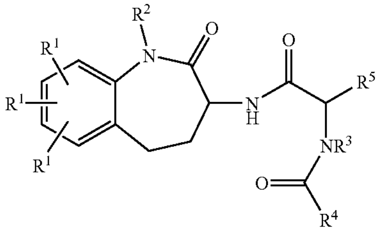

or a pharmaceutically acceptable salts or individual stereoisomer thereof.

3. The compound according to claim 1 represented by Formula (Ib):

(Ib)

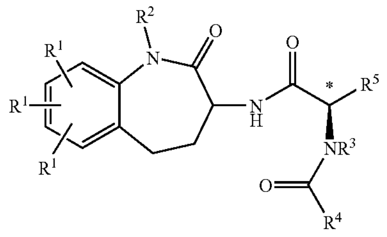

or a pharmaceutically acceptable salts or individual stereoisomer thereof.

4. The compound according to claim 1 represented by Formula (Ic):

(Ic)

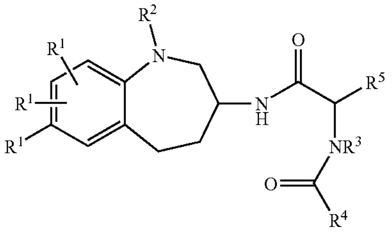

or a pharmaceutically acceptable salts or individual stereoisomers thereof.

5. The compound according to claim 1 represented by Formula (Id):

(Id)

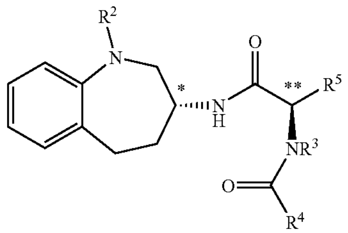

or a pharmaceutically acceptable salts or individual stereoisomers thereof.

6. The compound according to claim 1 represented by Formula (Ie):

(Ie)

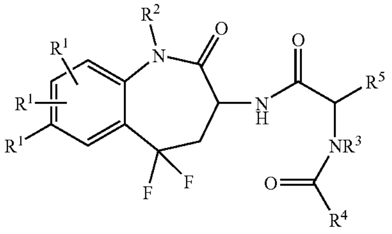

or a pharmaceutically acceptable salts or individual stereoisomers thereof.

7. The compound according to claim 1 represented by Formula (If):

(If)

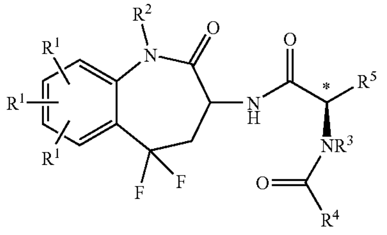

or a pharmaceutically acceptable salts or individual stereoisomers thereof.

8. The compound according to claim 1 represented by Formula (Ig):

(Ig)

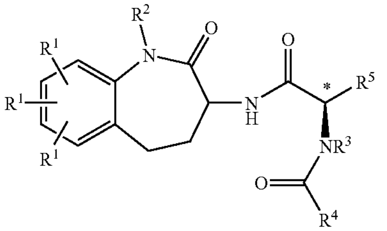

or a pharmaceutically acceptable salts or individual stereoisomer thereof, wherein $R^2$ is selected from the group consisting of:

$C_{1-6}$ alkyl, unsubstituted or substituted with one to six halogens, and $C_{3-6}$ cycloalkyl-$C_{0-6}$alkyl, wherein said cycloalkyl is unsubstituted or substituted with one to six substituents independently selected from halogen, cyano, $C_{1-6}$ alkyl and $C_{1-6}$ alkoxy, wherein alkyl and alkoxyl are unsubstituted or substituted with one to six halogens.

9. The compound according to claim 1 represented by Formula (Ih):

(Ih)

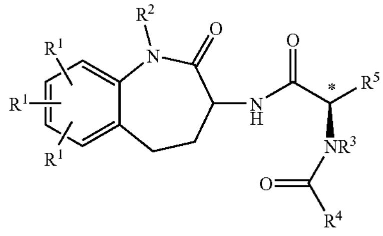

or a pharmaceutically acceptable salts or individual stereoisomer thereof, wherein $R^5$ is $(CH_2)_n$—$C_{6-10}$aryl, wherein aryl is unsubstituted or substituted with one to five substituents independently selected from hydroxy, halogen, cyano, $C_{1-6}$ alkyl and $C_{1-6}$ alkoxy, wherein alkyl and alkoxy are unsubstituted or substituted with one to six halogens.

10. The compound according to claim 1 represented by Formula (II):

(Ii)

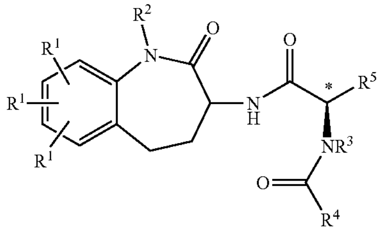

or a pharmaceutically acceptable salts or individual stereoisomer thereof, wherein $R^4$ is —O—$C_{1-10}$alkyl, unsubstituted or substituted with one to six halogens, or $(CH_2)_n$—$C_{6-10}$aryl, wherein aryl is unsubstituted or substituted with one to five substituents independently selected from halogen, cyano, $C_{1-6}$ alkyl and $C_{1-6}$ alkoxy, wherein alkyl and alkoxy are unsubstituted or substituted with one to six halogens.

11. The compound according to claim 1 represented by

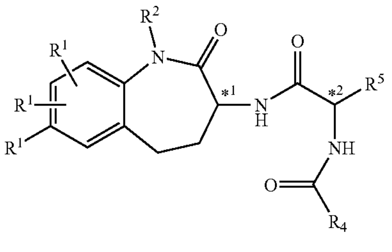

| $R^1$ | $R^2$ | *1, *2 | $R^4$ | $R^5$ |
|---|---|---|---|---|
| H | $CH_3$ | R,R | OtBu | 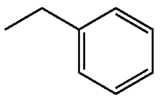 |

-continued
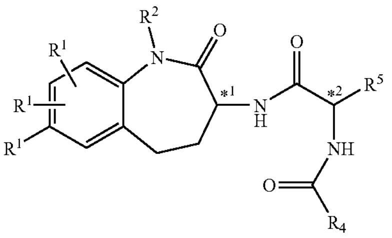
| $R^1$ | $R^2$ | *1, *2 | $R^4$ | $R^5$ |
|---|---|---|---|---|
| H | $CH_3$ | RS,R | OtBu | 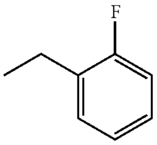 |
| H | $CH_3$ | R,R | OtBu | 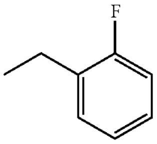 |
| H | cyclopropyl-methyl | R,R | OtBu | 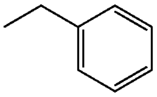 |
| H | cyclopropyl-methyl | R,R | OtBu | 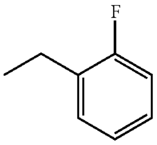 |
| H | $CF_3CH_2$— | R,R | OtBu | 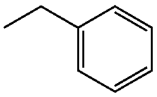 |
| H | $CF_3CH_2$— | R,R | OtBu | 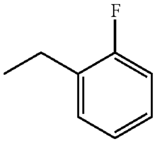 |
| H | $CF_3CH_2$— | R,R | OtBu | 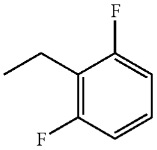 |
| H | n-propyl | R,R | OtBu | 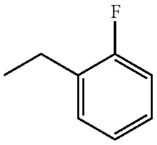 |
| H | i-propyl | R,R | OtBu | 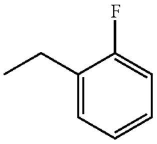 |

-continued
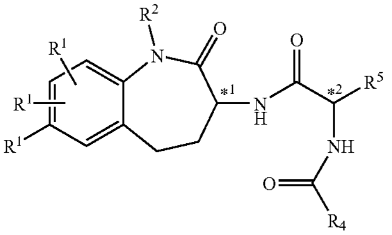
| $R^1$ | $R^2$ | *1, *2 | $R^4$ | $R^5$ |
|---|---|---|---|---|
| H | allyl | R,R | OtBu | 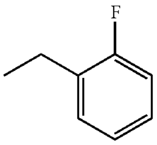 |
| H | $—CH_2CONH_2$ | R,R | OtBu | 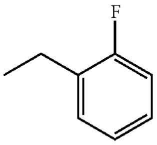 |
| H | i-propyl | R,R | OtBu | 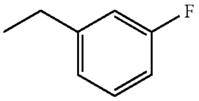 |
| H | i-propyl | R,R | OtBu | 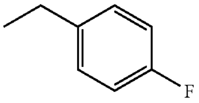 |
| H | i-propyl | R,R | OtBu | 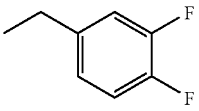 |
| H | i-propyl | R,R | OtBu | 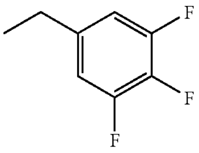 |
| H | i-propyl | R,R | OtBu | 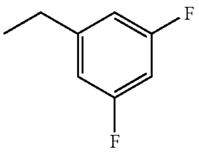 |
| H | i-propyl | R,R | OtBu | 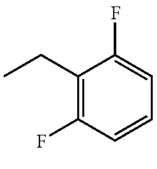 |

-continued
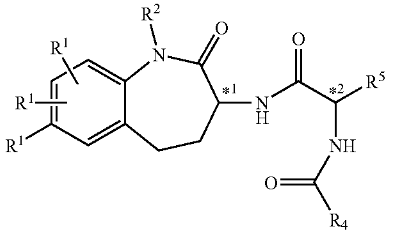
| $R^1$ | $R^2$ | *1, *2 | $R^4$ | $R^5$ |
| --- | --- | --- | --- | --- |
| H | i-propyl | R,R | OtBu | 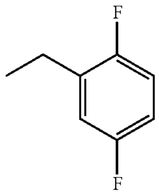 |
| H | i-propyl | R,R | OtBu | 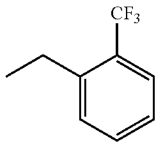 |
| H | i-propyl | R,R | OtBu | 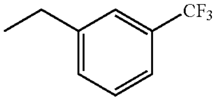 |
| H | i-propyl | R,R | OtBu | 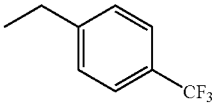 |
| H | i-propyl | R,R | OtBu | 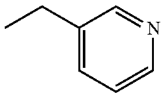 |
| H | i-propyl | R,R | OtBu | 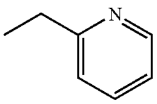 |
| H | i-propyl | R,R | OtBu | 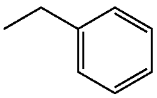 |
| H | i-propyl | R,R | OtBu | 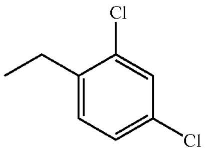 |
| H | i-propyl | R,R | OtBu | 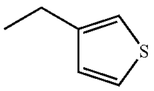 |

-continued
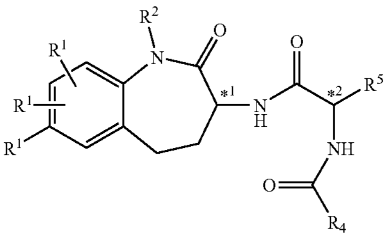
| $R^1$ | $R^2$ | *1, *2 | $R^4$ | $R^5$ |
|---|---|---|---|---|
| H | i-propyl | R,R | OtBu | 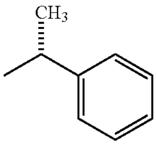 |
| H | i-propyl | R,R | OtBu | 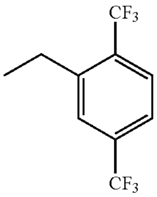 |
| H | i-propyl | R,R | OtBu | 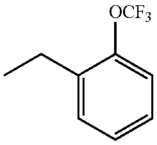 |
| H | i-propyl | R,R | OtBu | 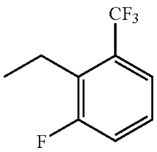 |
| H | i-propyl | R,R | OtBu | 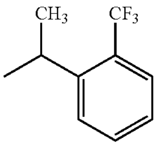 |
| H | i-propyl | R,R | OtBu | 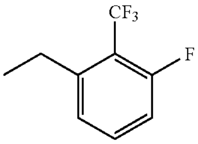 |
| H | i-propyl | R,R | OtBu | 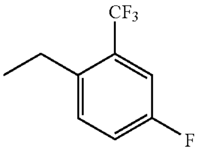 |
| H | i-propyl | R,R | OtBu | 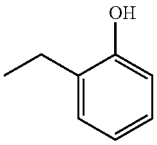 |

-continued
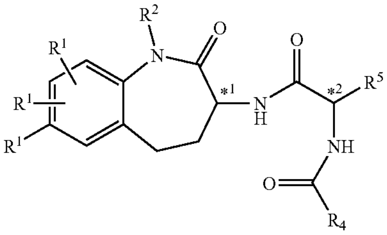
| $R^1$ | $R^2$ | *1, *2 | $R^4$ | $R^5$ |
|---|---|---|---|---|
| H | i-propyl | R,R | OtBu | 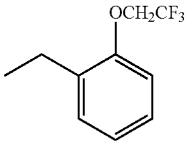 |
| H | i-propyl | R,R | -t-butyl | 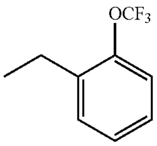 |
| H | $CF_3CH_2$— | R,R | -t-butyl | 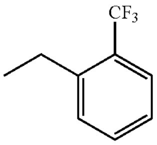 |
| H | H | R,R | OtBu | 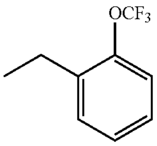 |
| H | H | S,R | OtBu | 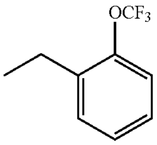 |
| H | i-propyl | S,R | OtBu | 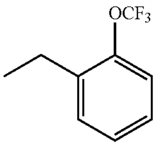 |
| H | i-propyl | R,R | 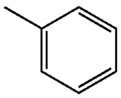 | 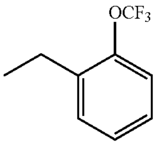 |
| H | i-propyl | R,R | 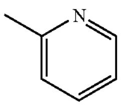 | 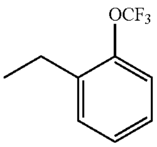 |

-continued
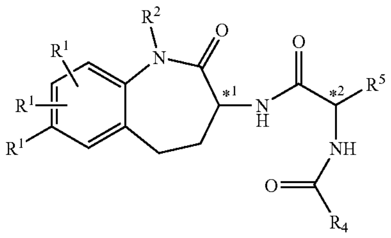
| $R^1$ | $R^2$ | *1, *2 | $R^4$ | $R^5$ |
|---|---|---|---|---|
| H | i-propyl | R,R | 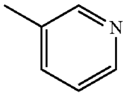 | 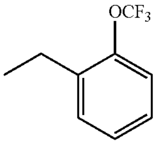 |
| H | i-propyl | R,R | 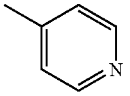 | 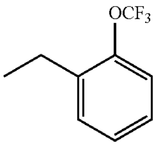 |
| H | i-propyl | R,R | 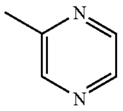 | 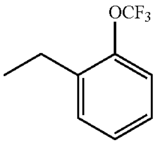 |
| H | i-propyl | R,R | 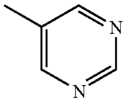 | 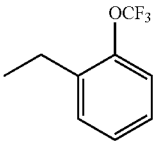 |
| H | i-propyl | R,R | 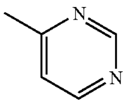 | 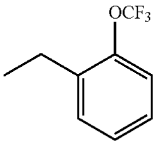 |
| H | i-propyl | R,R | 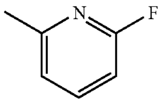 | 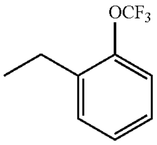 |
| H | i-propyl | R,R | 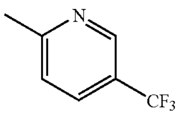 | 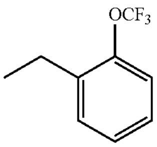 |
| H | i-propyl | R,R | 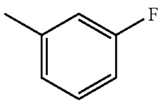 | 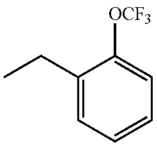 |

-continued
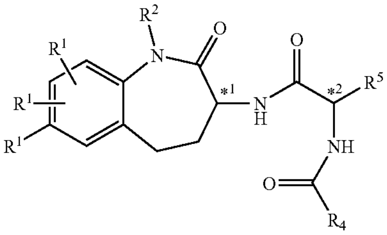
| R¹ | R² | *1, *2 | R⁴ | R⁵ |
|---|---|---|---|---|
| H | i-propyl | R,R | 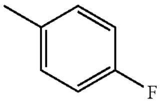 | 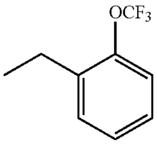 |
| H | i-propyl | R,R | 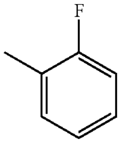 | 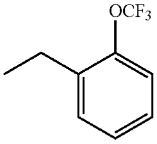 |
| H | i-propyl | R,R | 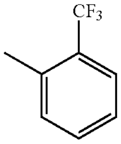 | 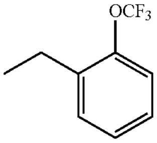 |
| H | i-propyl | R,R | 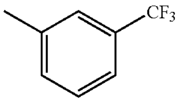 | 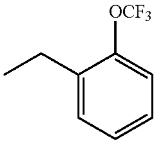 |
| H | i-propyl | R,R | 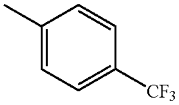 | 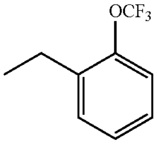 |
| H | i-propyl | R,R | 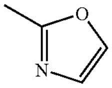 | 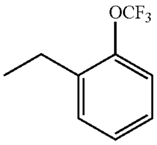 |
| H | i-propyl | R,R | 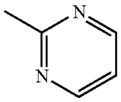 | 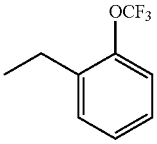 |
| H | i-propyl | R,R | 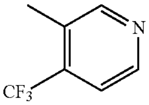 | 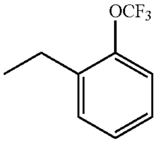 |

-continued
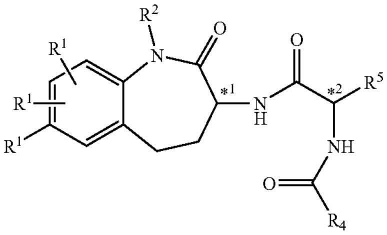
| R¹ | R² | *1, *2 | R⁴ | R⁵ |
|---|---|---|---|---|
| H | i-propyl | R,R | 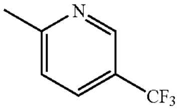 | 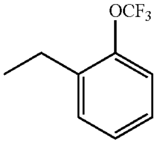 |
| H | i-propyl | R,R | 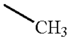 | 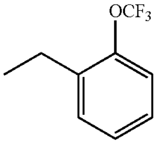 |
| H | i-propyl | R,R | 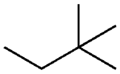 | 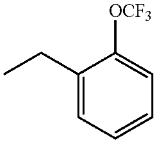 |
| H | i-propyl | R,R | 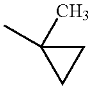 | 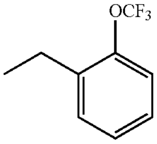 |
| H | i-propyl | R,R | 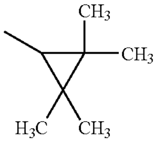 | 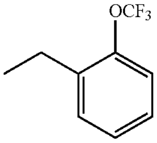 |
| H | i-propyl | R,R | 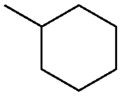 | 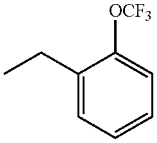 |
| H | i-propyl | R,R | 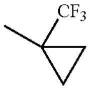 | 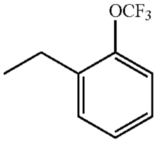 |
| H | i-propyl | R,R | 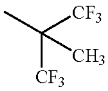 | 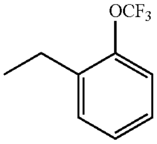 |

-continued
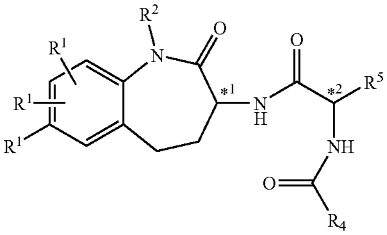
| $R^1$ | $R^2$ | *1, *2 | $R^4$ | $R^5$ |
|---|---|---|---|---|
| H | i-propyl | R,R | 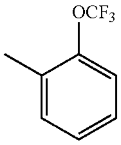 | 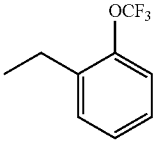 |
| H | i-propyl | R,R | 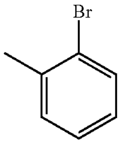 | 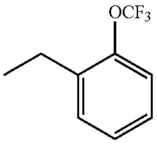 |
| H | i-propyl | R,R | 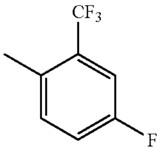 | 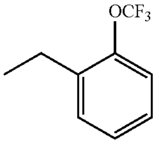 |
or a pharmaceutically acceptable salts or individual stereoisomer thereof.
12. The compound according to claim 1 represented by
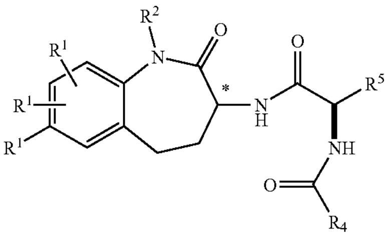
| $R^1$ | $R^2$ | * | $R^4$ | $R^5$ |
|---|---|---|---|---|
| 7-CF3 | i-propyl | RS | OtBu | 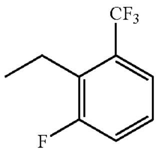 |
| 7,9-di-F | i-propyl | R | OtBu | 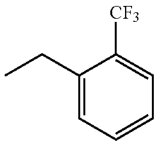 |
-continued
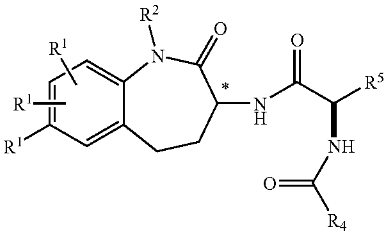
| $R^1$ | $R^2$ | * | $R^4$ | $R^5$ |
|---|---|---|---|---|
| 7,9-di-F | i-propyl | S | OtBu | 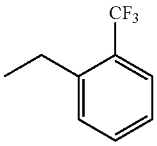 |
| 7,9-di-F | i-propyl | RS | OtBu | 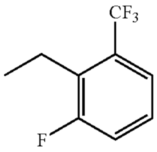 |

-continued
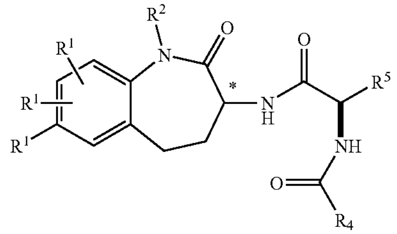
| $R^1$ | $R^2$ | * | $R^4$ | $R^5$ |
|---|---|---|---|---|
| 7,9-di-F | i-propyl | R | OtBu | 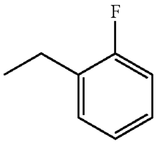 |
| 7,9-di-F | i-propyl | S | OtBu | 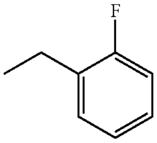 |
| 7,9-di-F | i-propyl | R | OtBu | 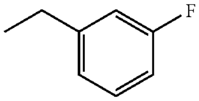 |
| 7,9-di-F | i-propyl | S | OtBu | 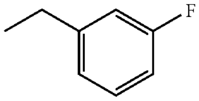 |
| 7,9-di-F | i-propyl | R | OtBu | 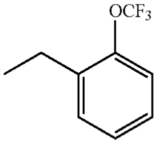 |
| 7,9-di-F | i-propyl | S | OtBu | 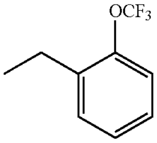 |
| 7-F | i-propyl | R | OtBu | 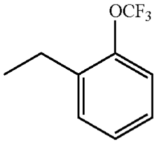 |
| 7-F | i-propyl | S | OtBu | 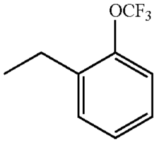 |
| 7-F | i-propyl | R | OtBu | 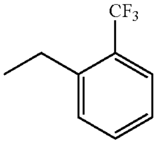 |
-continued
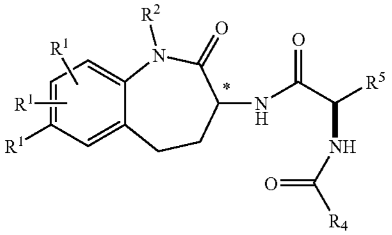
| $R^1$ | $R^2$ | * | $R^4$ | $R^5$ |
|---|---|---|---|---|
| 7-F | i-propyl | S | OtBu | 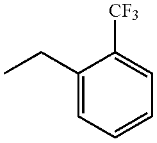 |
| 7-F | i-propyl | R | OtBu | 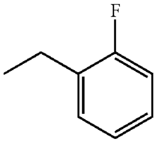 |
| 7-F | i-propyl | S | OtBu | 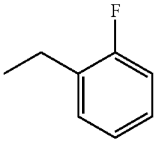 |
| 8-F | i-propyl | R | OtBu | 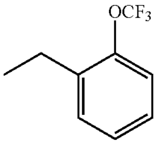 |
| 8-F | i-propyl | S | OtBu | 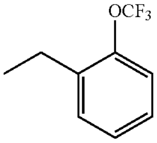 |
| 8-F | i-propyl | R | OtBu | 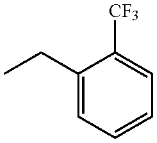 |
| 8-F | i-propyl | S | OtBu | 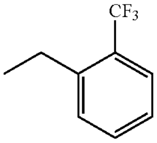 |
| 9-F | i-propyl | R | OtBu | 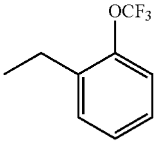 |

-continued
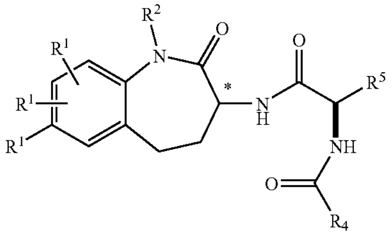
| $R^1$ | $R^2$ | * | $R^4$ | $R^5$ |
|---|---|---|---|---|
| 9-F | i-propyl | S | OtBu | 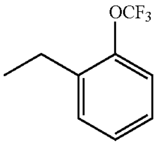 |
| 9-F | i-propyl | R | OtBu | 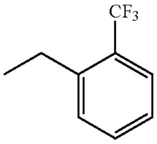 |
| 9-F | i-propyl | S | OtBu | 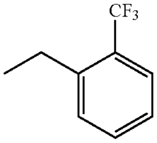 |
| 8-$CF_3$ | i-propyl | R | OtBu | 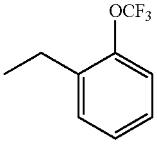 |
| 8-$CF_3$ | i-propyl | R | OtBu | 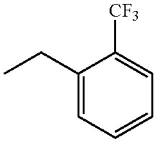 |
| 8-$CF_3$ | i-propyl | S | OtBu | 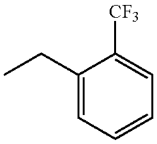 |
| 7-Br | i-propyl | R | OtBu | 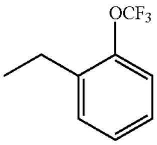 |
| 7,9-di-F | i-propyl | R | 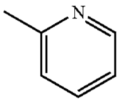 | 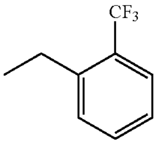 |
-continued
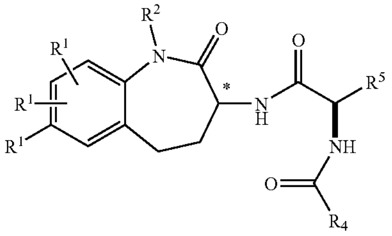
| $R^1$ | $R^2$ | * | $R^4$ | $R^5$ |
|---|---|---|---|---|
| 7,9-di-F | i-propyl | S | 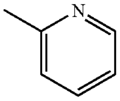 | 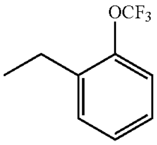 |
| 7-F | i-propyl | R | 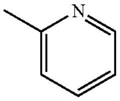 | 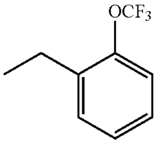 |
| 7-F | i-propyl | S | 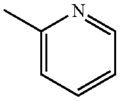 | 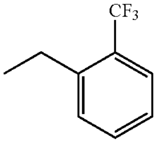 |
| 7-Cl | i-propyl | R | OtBu | 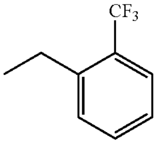 |
| 7-Cl | i-propyl | S | OtBu | 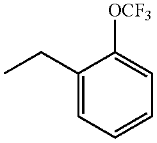 |
| 8-Cl | i-propyl | R | OtBu | 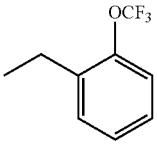 |
| 8-Cl | i-propyl | S | OtBu | 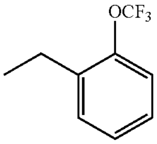 |
| 8-F | i-propyl | R | 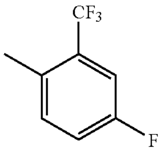 | 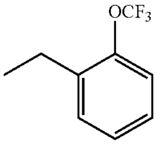 |

-continued
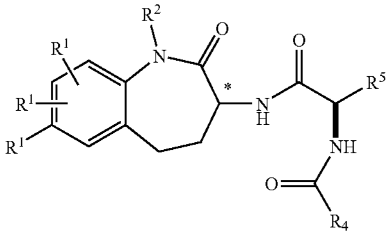
| $R^1$ | $R^2$ | * | $R^4$ | $R^5$ |
|---|---|---|---|---|
| 7-Cl | i-propyl | R | OtBu | 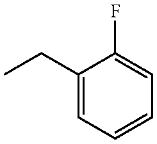 |
| 7-Cl | i-propyl | R | OtBu | 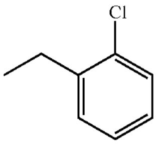 |
| 7-Cl | i-propyl | R | OtBu | 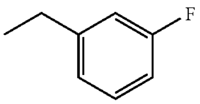 |
| 7-Cl | i-propyl | R | 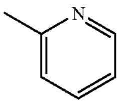 | 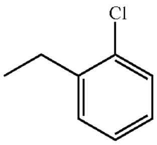 |
| 7-Cl | i-propyl | R | 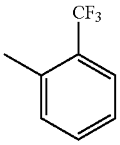 | 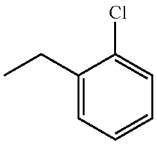 |
| 7-Cl | i-propyl | R | 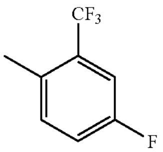 | 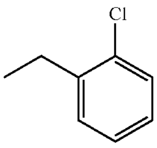 |
| 7-Cl | i-propyl | R | 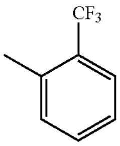 | 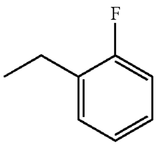 |
| 7-Cl | i-propyl | R | 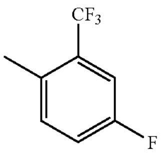 | 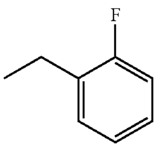 |
-continued
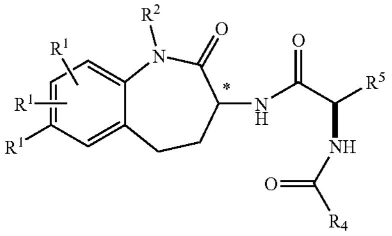
| $R^1$ | $R^2$ | * | $R^4$ | $R^5$ |
|---|---|---|---|---|
| 7-Cl | i-propyl | R | 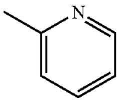 | 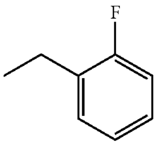 |
| 7-Cl | i-propyl | R | 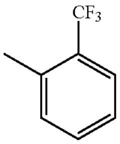 | 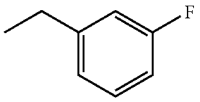 |
| 7-Cl | i-propyl | R | 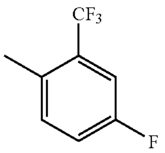 | 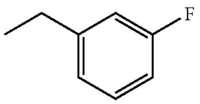 |
| 7-Cl | i-propyl | R | 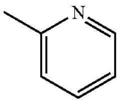 | 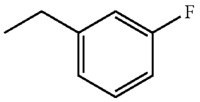 |
| 7-Cl | i-propyl | R | 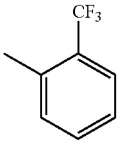 | 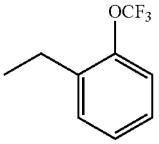 |
| 7-Cl | i-propyl | R | 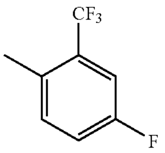 | 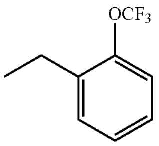 |
| 7-Cl | i-propyl | R | 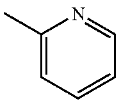 | 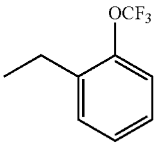 |
| 7-$CF_3$ | i-propyl | R | OtBu | 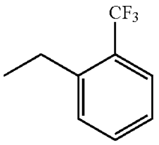 |

-continued
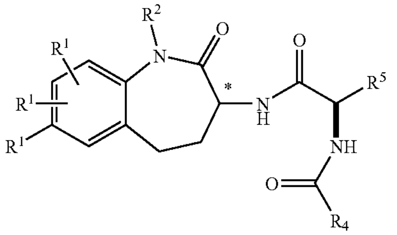
| $R^1$ | $R^2$ | * | $R^4$ | $R^5$ |
|---|---|---|---|---|
| 7-$CF_3$ | i-propyl | S | OtBu | 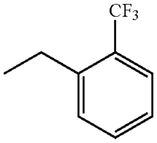 |
| 7-$CF_3$ | i-propyl | R | OtBu | 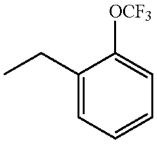 |
| 7-$CF_3$ | i-propyl | S | OtBu | 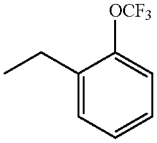 |
| 7-$CF_3$ | i-propyl | R | OtBu | 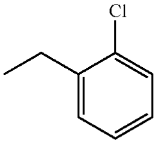 |
| 7-$CF_3$ | i-propyl | S | OtBu | 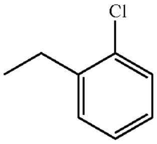 |
| 7-$CF_3$ | i-propyl | R | OtBu | 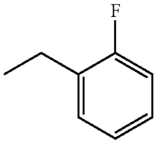 |
| 7-$CF_3$ | i-propyl | S | OtBu | 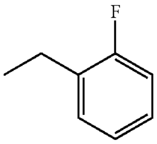 |
| 7-$CF_3$ | i-propyl | R | 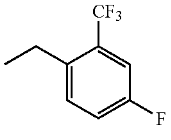 | 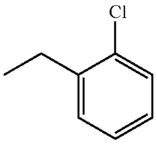 |
-continued
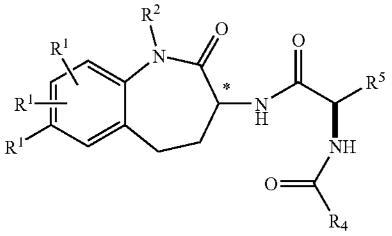
| $R^1$ | $R^2$ | * | $R^4$ | $R^5$ |
|---|---|---|---|---|
| 7-$CF_3$ | i-propyl | R | 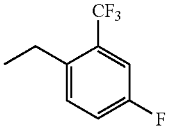 | 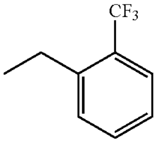 |
| 7-$CF_3$ | i-propyl | R | 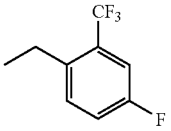 | 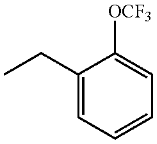 |
| 7-$CF_3$ | i-propyl | R | OtBu | 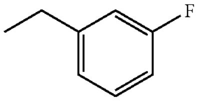 |
| 7-F | i-propyl | R | 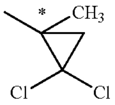 isomer 1 | 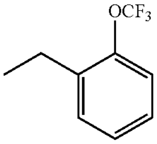 |
| 7-F | i-propyl | R | 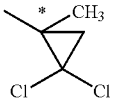 isomer 2 | 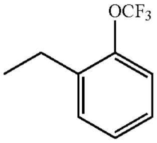 |
| 7-F | i-propyl | R | 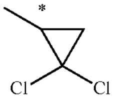 isomer 1 | 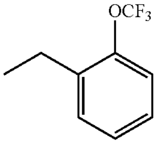 |
| 7-F | i-propyl | R | 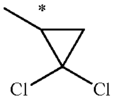 isomer 2 | 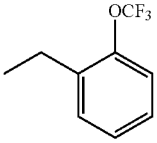 |
| 7-F | i-propyl | R | 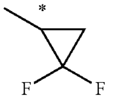 isomer 1 | 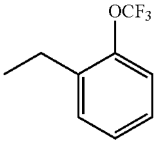 |

-continued
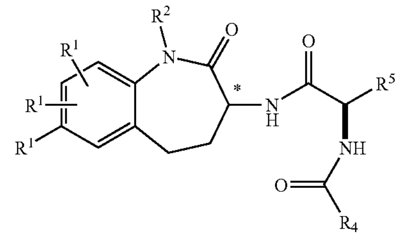
| $R^1$ | $R^2$ | * | $R^4$ | $R^5$ |
|---|---|---|---|---|
| 7-F | i-propyl | R | 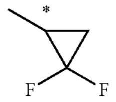 isomer 2 | 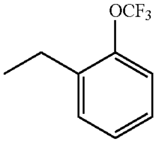 |
| 7-F | i-propyl | R | 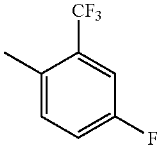 | 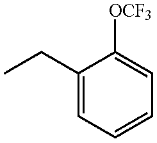 |
| 7-F | i-propyl | R | 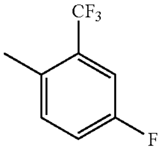 | 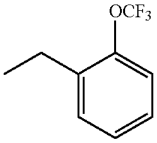 |
| 7-F | i-propyl | R | 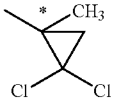 stereoisomeric mixture | 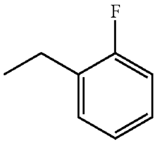 |
| 7-F | i-propyl | R | 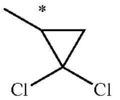 isomer 1 | 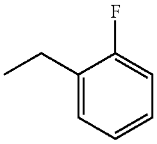 |
| 7-F | i-propyl | R | 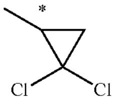 isomer 2 | 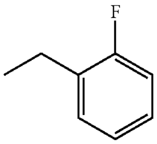 |
| 7-F | i-propyl | R | 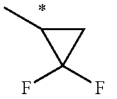 isomer 1 | 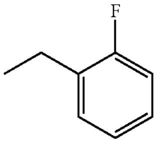 |
| 7-F | i-propyl | R | 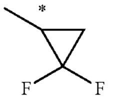 isomer 2 | 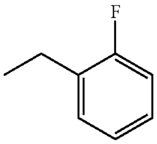 |
-continued
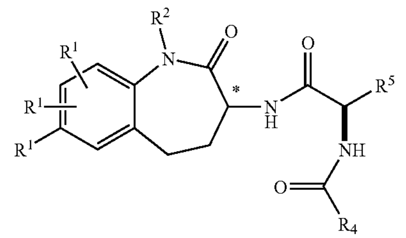
| $R^1$ | $R^2$ | * | $R^4$ | $R^5$ |
|---|---|---|---|---|
| 7-F | i-propyl | R | 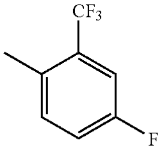 | 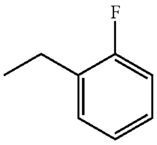 |
| 7-F | i-propyl | R | 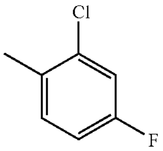 | 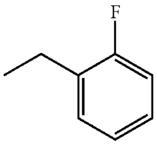 |
| 7-F | i-propyl | R | 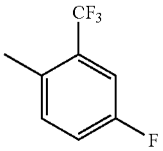 | 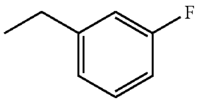 |
| 7-F | i-propyl | R | 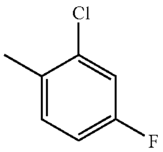 | 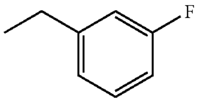 |
| 7-$CF_3$ | i-propyl | R | 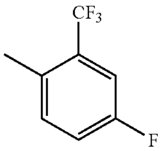 | 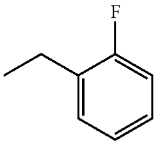 |
| 7-$CF_3$ | i-propyl | S | 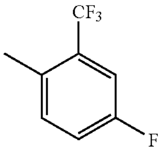 | 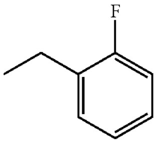 |
| 7-$OCF_3$ | i-propyl | R | 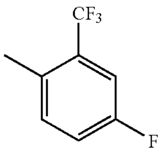 | 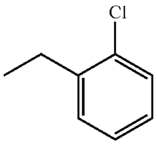 |
| 7-$OCF_3$ | i-propyl | S | 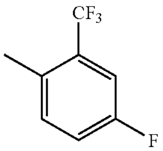 | 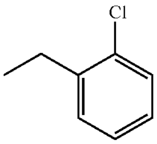 |

-continued

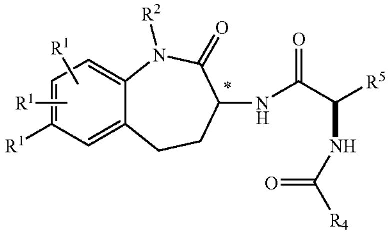

| $R^1$ | $R^2$ | * | $R^4$ | $R^5$ |
|---|---|---|---|---|
| 7-$OCF_3$ | i-propyl | R | OtBu | 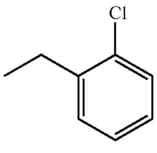 |
| 7-$OCF_3$ | i-propyl | S | OtBu | 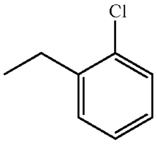 |
| 7-$CF_3$ | i-propyl | R | 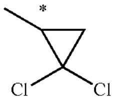 stereoisomeric mixture | 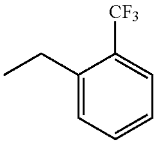 |
| 7-$CF_3$ | i-propyl | S | 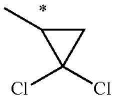 stereoisomeric mixture | 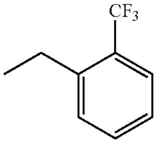 |
| 7-$OCF_3$ | i-propyl | R | OtBu | 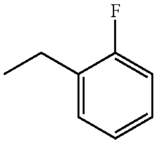 |
| 7-$OCF_3$ | i-propyl | S | OtBu | 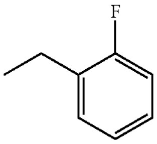 |
| 7-$CF_3$ | i-propyl | R | 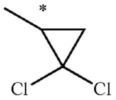 stereoisomeric mixture | 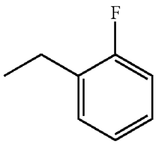 |
| 7-$CF_3$ | i-propyl | S | 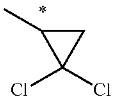 stereoisomeric mixture | 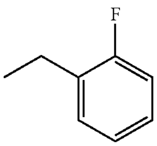 |

-continued

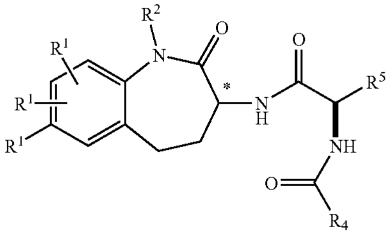

| $R^1$ | $R^2$ | * | $R^4$ | $R^5$ |
|---|---|---|---|---|
| 7-$CF_3$ | i-propyl | R | 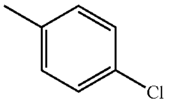 | 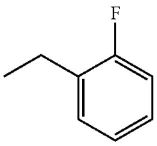 |
| 7-$CF_3$ | i-propyl | S | 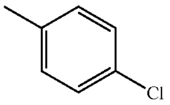 | 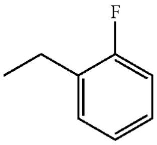 |
| 7-$OCF_3$ | i-propyl | R | 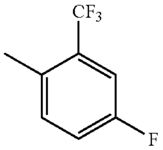 | 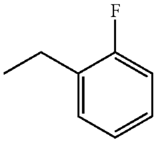 |
| 7-$OCF_3$ | i-propyl | S | 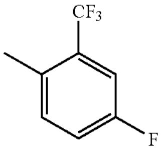 | 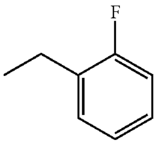 |
| 7-$CF_3$ | i-propyl | R | 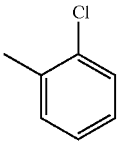 | 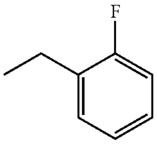 |
| 7-$CF_3$ | i-propyl | S | 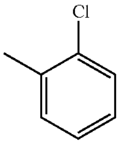 | 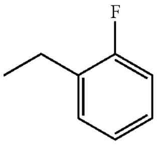 |
| 6,7,9-tri-F | i-propyl | R | OtBu | 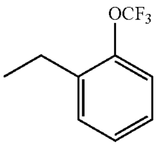 |
| 6,7,9-tri-F | i-propyl | S | OtBu | 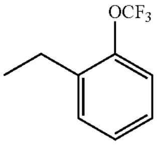 |

-continued
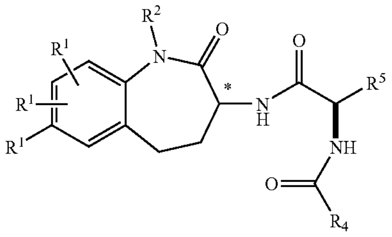
| $R^1$ | $R^2$ | * | $R^4$ | $R^5$ |
|---|---|---|---|---|
| 6,7,9-tri-F | i-propyl | R | OtBu | 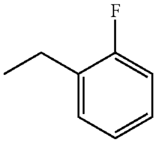 |
| 6,7,9-tri-F | i-propyl | S | OtBu | 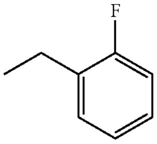 |
| 6,7,9-tri-F | i-propyl | R | OtBu | 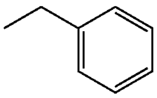 |
| 6,7,9-tri-F | i-propyl | S | OtBu | 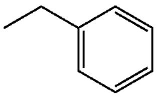 |
| 6,7,9-tri-F | i-propyl | R | 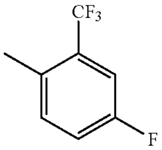 | 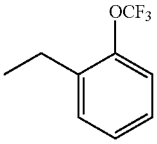 |
| 6,7,9-tri-F | i-propyl | R | 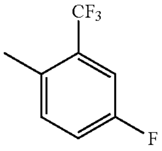 | 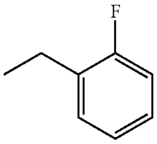 |
| 6,7,9-tri-F | i-propyl | R | 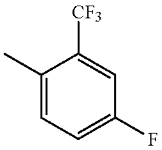 | 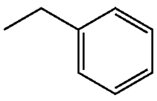 |
| 6,7,9-tri-F | i-propyl | R | 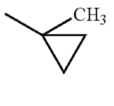 | 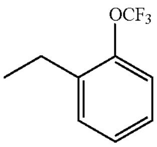 |
-continued
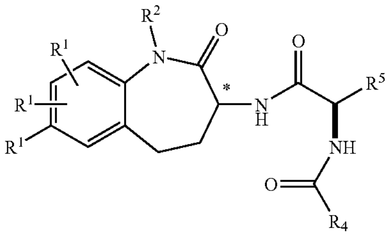
| $R^1$ | $R^2$ | * | $R^4$ | $R^5$ |
|---|---|---|---|---|
| 6,7,9-tri-F | i-propyl | R | 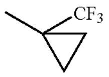 | 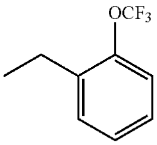 |
| 6,7,9-tri-F | i-propyl | R | 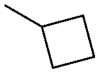 | 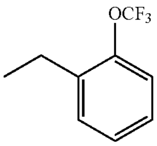 |
| 6,7,9-tri-F | i-propyl | R | 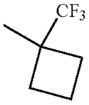 | 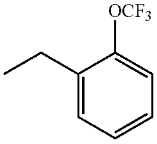 |
| 6,7,9-tri-F | i-propyl | R | 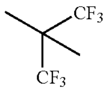 | 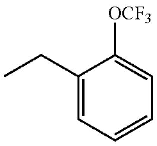 |
| 6,7,9-tri-F | i-propyl | R | 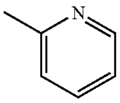 | 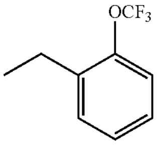 |
| 6,7,9-tri-F | i-propyl | R | 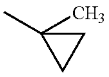 | 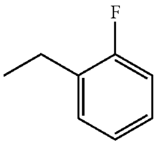 |
| 6,7,9-tri-F | i-propyl | R | 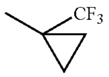 | 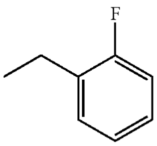 |
| 6,7,9-tri-F | i-propyl | R | 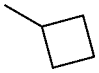 | 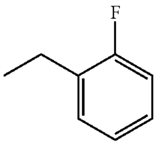 |

-continued
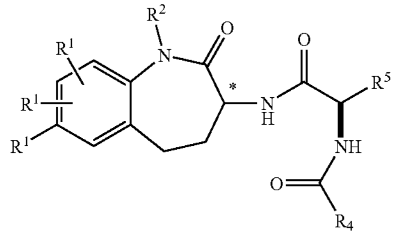
| $R^1$ | $R^2$ | * | $R^4$ | $R^5$ |
|---|---|---|---|---|
| 6,7,9-tri-F | i-propyl | R | 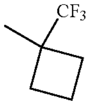 | 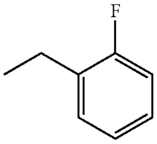 |
| 6,7,9-tri-F | i-propyl | R | 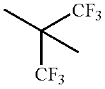 | 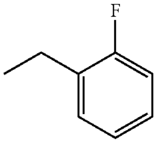 |
| 6,7,9-tri-F | i-propyl | R | 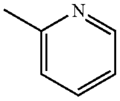 | 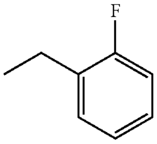 |
| 6,7,9-tri-F | i-propyl | S | 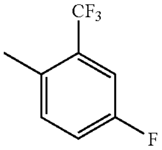 | 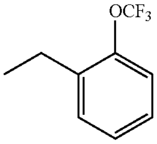 |
| 6,7,9-tri-F | i-propyl | S | 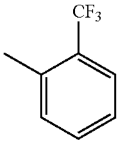 | 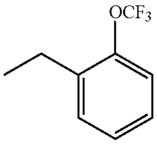 |
| 6,7,9-tri-F | i-propyl | S | 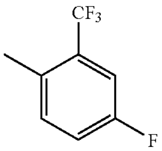 | 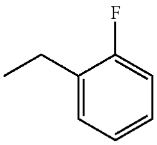 |
| 6,7,9-tri-F | i-propyl | S | 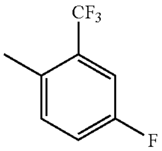 | 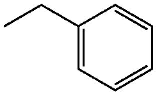 |
| 6,7,9-tri-F | i-propyl | R | 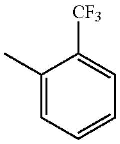 | 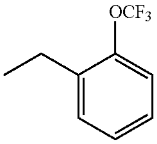 |
-continued
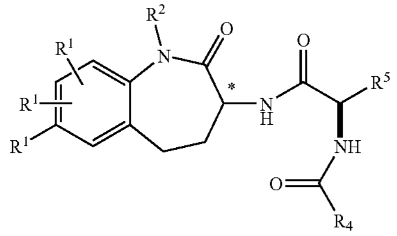
| $R^1$ | $R^2$ | * | $R^4$ | $R^5$ |
|---|---|---|---|---|
| 6,7,9-tri-F | i-propyl | R | 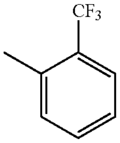 | 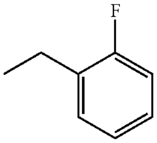 |
| 7,9-di-F | i-propyl | R | 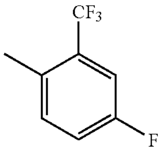 | 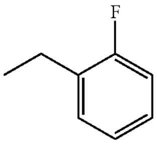 |
| 7,9-di-F | i-propyl | R | 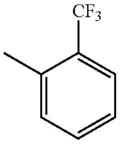 | 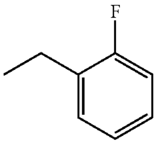 |
| 7,9-di-F | i-propyl | R | 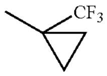 | 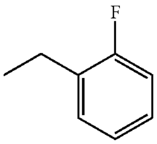 |
| 7,9-di-F | i-propyl | R | 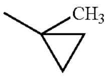 | 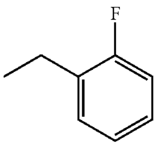 |
| 7,9-di-F | i-propyl | R | 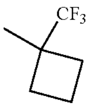 | 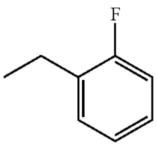 |
| 7,9-di-F | i-propyl | R | 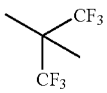 | 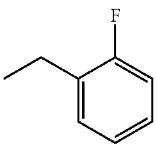 |
| 7-$OCF_3$ | i-propyl | R | 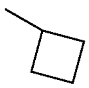 | 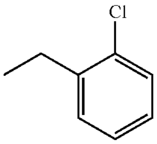 |

-continued
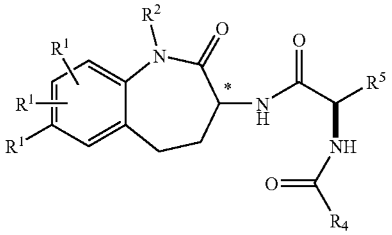
| R¹ | R² | * | R⁴ | R⁵ |
|---|---|---|---|---|
| 7,9-di-F | i-propyl | R | 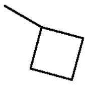 | 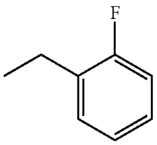 |
| 7-Cl | i-propyl | R | 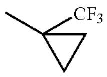 | 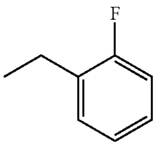 |
| 7-Cl | i-propyl | R | 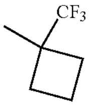 | 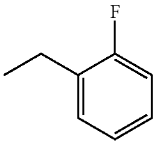 |
| 7-Cl | i-propyl | R | 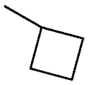 | 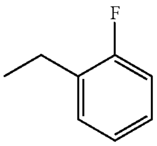 |
| 7-Cl | i-propyl | R | 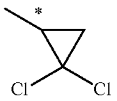 stereoisomeric mixture | 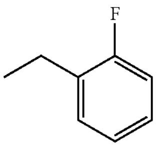 |
| 7-$CF_3$ | i-propyl | S | 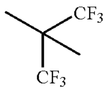 | 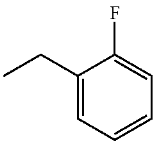 |
| 7-$OCF_3$ | i-propyl | R | 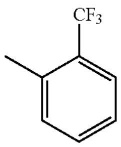 | 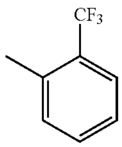 |
| 7-$CF_3$ | i-propyl | R | 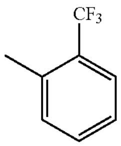 | 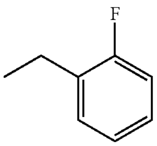 |
-continued
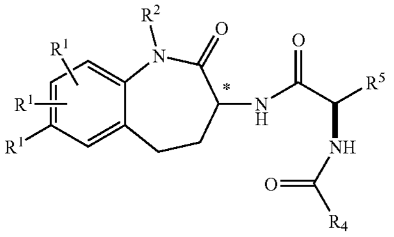
| R¹ | R² | * | R⁴ | R⁵ |
|---|---|---|---|---|
| 7-$CF_3$ | i-propyl | R | OtBu | 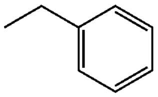 |
| 7-$CF_3$ | i-propyl | S | OtBu | 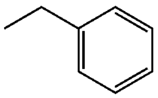 |
| 7-$OCF_3$ | i-propyl | R | 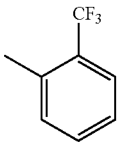 | 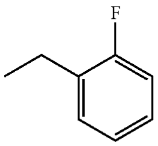 |
| 7-$OCF_3$ | i-propyl | S | 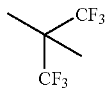 | 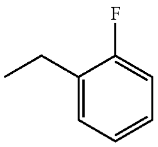 |
| 7-$OCF_3$ | i-propyl | R | 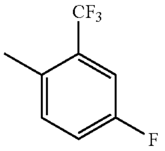 | 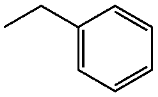 |
| 7-$OCF_3$ | i-propyl | R | OtBu | 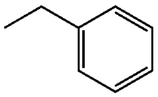 |
| 7,9-di-Ci | i-propyl | R | 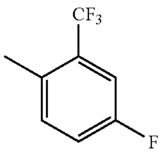 | 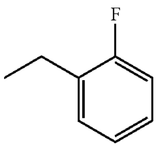 |
| 7-Cl, 9-F | i-propyl | R | OtBu | 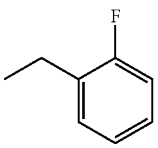 |
| 7-Cl, 9-F | i-propyl | R | 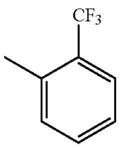 | 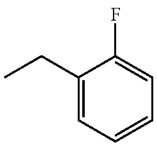 |

-continued
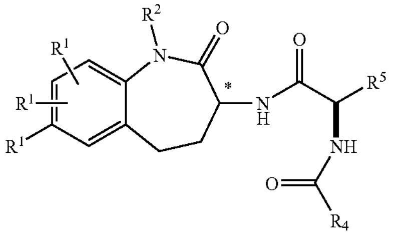
| $R^1$ | $R^2$ | * | $R^4$ | $R^5$ |
|---|---|---|---|---|
| 7-Cl, 9-F | i-propyl | R | 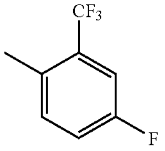 | 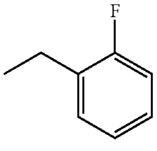 |
| 7-Cl, 9-F | i-propyl | R | 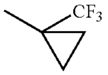 | 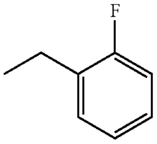 |
| 7-Cl | i-propyl | R | 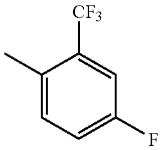 | 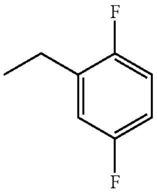 |
| 7-Cl, 9-F | i-propyl | R | 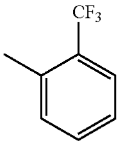 | 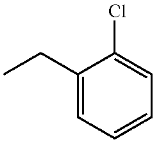 |
| 7-Cl, 9-F | i-propyl | R | 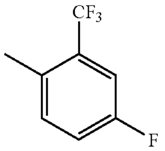 | 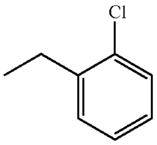 |
| 7-Cl, 9-F | i-propyl | R | 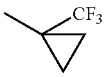 | 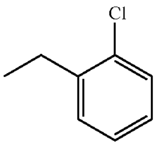 |
| 7-Cl, 9-F | i-propyl | R | 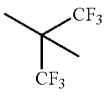 | 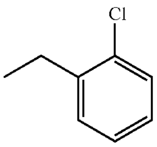 |
| 6,7,9-tri-F | 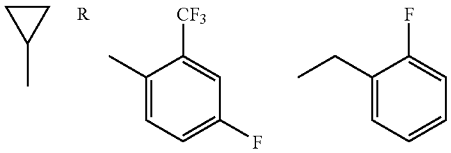 | R | | |
-continued
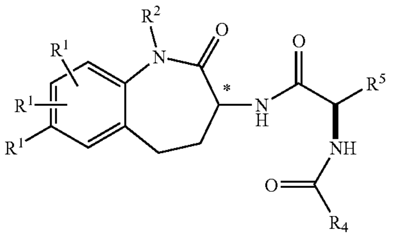
| $R^1$ | $R^2$ | * | $R^4$ | $R^5$ |
|---|---|---|---|---|
| 6,7,9-tri-F | 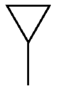 | R | 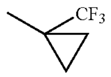 | 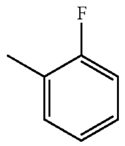 |
| 6,7,9-tri-F | 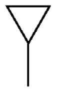 | R | 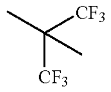 | 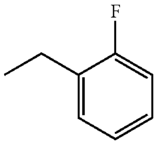 |
| 6,7,9-tri-F | 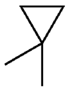 | R | 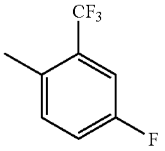 | 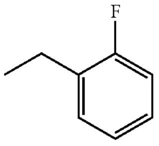 |
| 6,7,9-tri-F | 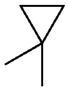 | R | 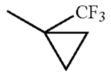 | 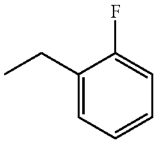 |
| 6,7,9-tri-F | 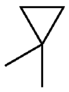 | R | 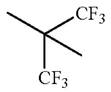 | 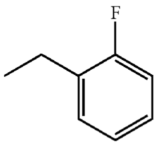 |
| 6,7,9-tri-F | 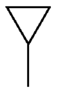 | R | 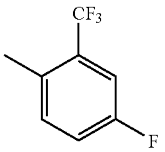 | 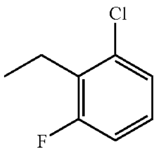 |
| 6,7,9-tri-F | 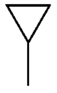 | R | 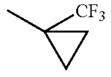 | 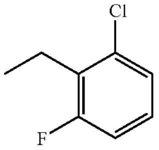 |
| 6,7,9-tri-F | 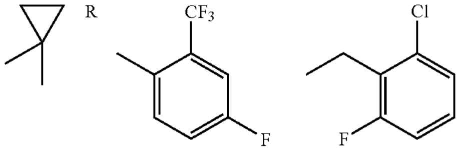 | R | | |

-continued

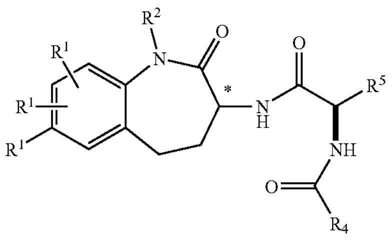

| $R^1$ | $R^2$ | * | $R^4$ | $R^5$ |
|---|---|---|---|---|
| 6,7,9-tri-F | 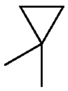 | R | 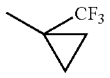 | 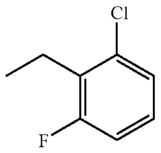 |

or a pharmaceutically acceptable salts or individual stereoisomer thereof.

13. The compound according to claim 1 represented by

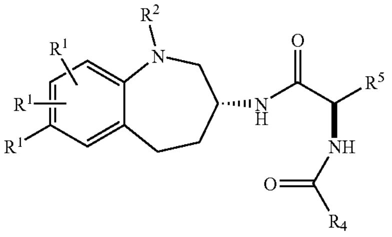

| $R^1$ | $R^2$ | $R^4$ | $R^5$ |
|---|---|---|---|
| H | Me | OtBu | 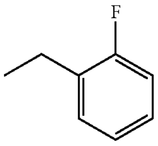 |
| H | $CH_2CF_3$ | OtBu | 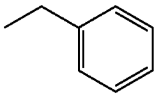 |
| H | $CH_2CF_3$ | OtBu | 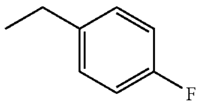 |
| H | $CH_2CF_3$ | OtBu | 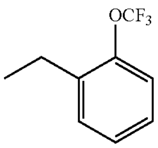 |
| H | H | OtBu | 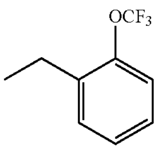 |

-continued

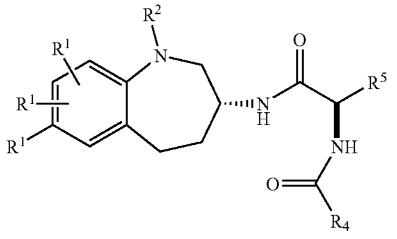

| $R^1$ | $R^2$ | $R^4$ | $R^5$ |
|---|---|---|---|
| H | $CH_2CF_3$ | OtBu | 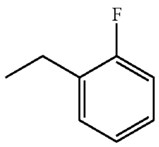 |

or a pharmaceutically acceptable salts or individual stereoisomers thereof.

14. The compound according to claim 1 represented by

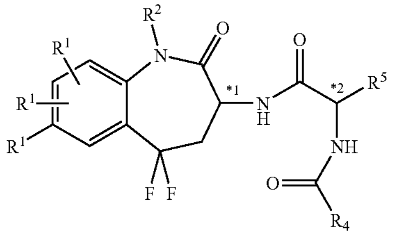

| $R^1$ | $R^2$ | *1, *2 | $R^4$ | $R^5$ |
|---|---|---|---|---|
| H | $CH_3$ | RS,R | OtBu | 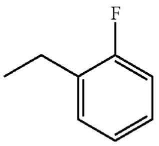 |
| H | i-propyl | RS,R | OtBu | 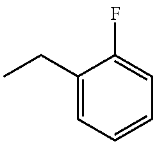 |
| H | i-propyl | RS,R | OtBu | 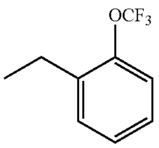 |
| 7-Cl | i-propyl | R,R | OtBu | 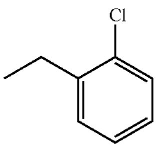 |

-continued

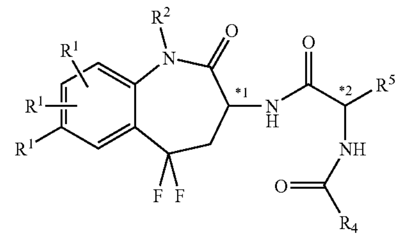

| $R^1$ | $R^2$ | *1, *2 | $R^4$ | $R^5$ |
|---|---|---|---|---|
| 7-Cl | i-propyl | S,R | OtBu | 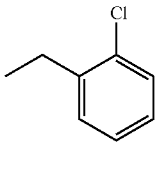 |
| 7-Cl | i-propyl | S,R | 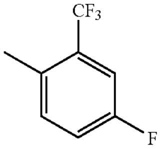 | 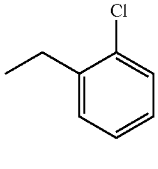 |
| 7-Cl | i-propyl | R,R | 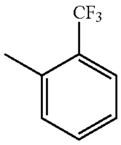 | 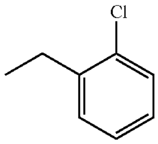 |
| 7-Cl | i-propyl | S,R | 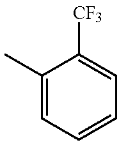 | 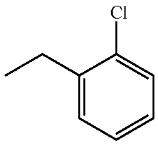 |

or a pharmaceutically acceptable salts or individual stereoisomer thereof.

15. A pharmaceutical composition comprising a therapeutically effective amount of a compound according to claim 1, or a pharmaceutically acceptable salt or individual stereoisomer thereof, and a pharmaceutically acceptable carrier.

16. A method of treatment of pain comprising the step of administering to a patient in need thereof a therapeutically effective amount of a compound according to claim 1, or a pharmaceutically acceptable salt or individual stereoisomer thereof.

17. A method of treatment of chronic, visceral, inflammatory and/or neuropathic pain syndromes comprising the step of administering to a patient in need thereof a therapeutically effective amount, or a prophylactically effective amount, of a compound according to claim 1, or a pharmaceutically acceptable salt or individual stereoisomer thereof.

18. A method of treatment of pain resulting from, or associated with, traumatic nerve injury, nerve compression or entrapment, postherpetic neuralgia, trigeminal neuralgia, diabetic neuropathy, cancer and/or chemotherapy, comprising the step of administering to a patient in need thereof a therapeutically effective amount, or a prophylactically effective amount, of a compound according to claim 1, or a pharmaceutically acceptable salt or individual stereoisomer thereof.

19. A method of treatment of chronic lower back pain comprising the step of administering to a patient in need thereof a therapeutically effective amount, or a prophylactically effective amount, of a compound according to claim 1, or a pharmaceutically acceptable salt or individual stereoisomer thereof.

20. A method of treatment of phantom limb pain comprising the step of administering to a patient in need thereof a therapeutically effective amount, or a prophylactically effective amount, of a compound according to claim 1, or a pharmaceutically acceptable salt or individual stereoisomer thereof.

21. A method of treatment of HIV- and HIV treatment-induced neuropathy, chronic pelvic pain, neuroma pain, complex regional pain syndrome, chronic arthritic pain and/or related neuralgias comprising the step of administering to a patient in need thereof a therapeutically effective amount, or a prophylactically effective amount, of a compound according to claim 1, or a pharmaceutically acceptable salt or individual stereoisomer thereof.

* * * * *